(12) United States Patent
Hotez et al.

(10) Patent No.: US 8,211,438 B2
(45) Date of Patent: Jul. 3, 2012

(54) HUMAN HOOKWORM VACCINE

(75) Inventors: Peter Hotez, Bethesda, MD (US);
Alexander Loukas, Herston (AU); Bin Zhan, North Potomac, MD (US);
Gaddam Goud, Gaithersburg, MD (US);
Jeffrey Bethony, Washington, DC (US);
Maria Elena Bottazzi, Washington, DC (US); Aaron Miles, Washington, DC (US)

(73) Assignee: The George Washington University, Washington, DC (US)

( * ) Notice: Subject to any disclaimer, the term of this patent is extended or adjusted under 35 U.S.C. 154(b) by 250 days.

(21) Appl. No.: 12/492,734

(22) Filed: Jun. 26, 2009

(65) Prior Publication Data
US 2010/0003285 A1  Jan. 7, 2010

Related U.S. Application Data

(63) Continuation of application No. 11/863,912, filed on Sep. 28, 2007, now abandoned.

(60) Provisional application No. 60/862,916, filed on Oct. 25, 2006.

(51) Int. Cl.
*A61K 39/00* (2006.01)
*A61K 39/002* (2006.01)

(52) U.S. Cl. ............... 424/191.1; 424/184.1; 424/185.1; 530/350

(58) Field of Classification Search ........................ None
See application file for complete search history.

(56) References Cited

U.S. PATENT DOCUMENTS
7,488,490 B2 *  2/2009  Davis et al. ................ 424/278.1

FOREIGN PATENT DOCUMENTS
WO      WO 01/62802 A1 *  8/2001

OTHER PUBLICATIONS

Brophy et al. Acta Tropica, 59 (1995) 259-263.*
Palmer et al. (Bull World Health Organ. 1996; 74 (4):381-386).*
Loukas et al (FEMs Immunology and Medical Microbiology, vol. 43, issue 2 p. 115-124, 2005.*
Loukas et al. Hookworm vaccines:past, present and future. The Lancet, 6 (11): 733-741, Nov. 2006 published online Oct. 23, 2006.*
Greenspan et al. (Nature Biotechnology 7: 936-937, 1999).
Abbas et al. Cellular and Molecular Immunology 2000 Chapter 15 p. 360-362.
Weeratna et al Vaccine 18:1755-1762, 2000.
Ellis, R.W. Chapter 29 of "Vaccines" Plotkin, S.A. et al. (eds) published by W. B. Saunders company (Philadelphia) in 1988.
Score search resullts- 2 pages alignment of SEQ ID No: 6 and AAG63965 (geneseq database, Nov. 13, 2001).
Fujiwara et al Human Vaccines 1:3, 123-128 May/Jun. 2005, Published online May 20, 2005.

* cited by examiner

*Primary Examiner* — Oluwatosin Ogunbiyi
(74) *Attorney, Agent, or Firm* — Whitham Curtis Christofferson & Cook, P.C.

(57) ABSTRACT

A vaccine for human hookworm is provided. The vaccine comprises at least one L3 larval stage antigen (e.g. Na-ASP-2 or Na-SAA-2) and at least one adult stage human hookworm antigen (e.g. Na-APR-1, Na-CP-2, Na-CP-3, Na-CP-4, Na-CP-5, or Na-GST-1) and adjuvants.

1 Claim, 21 Drawing Sheets

A.

gaaaatcaca atgatgtctt ctatcacatg tttggttctt ctctcgattg cagcgtactc caaagccggt tgtcctgaca
atggaatgtc agaggaagca cggcaaaaat tccttgaatt gcacaattcg ttgagaagtt cggttgcatt gggacaggcc
aaggatggag ctggtggaaa tgccccgaaa gctgctaaga tgaagacgat ggcatacgat tgcgaagttg
aaaagactgc aatgaataac gcgaaacaat gtgtattcaa gcactcgcaa cctaaccaaa ggaaaggatt
gggagagaat atatttatgt cttcggatag cggtatggac aaagcaaagg ctgctgagca ggctagcaaa gcttggttcg
gcgaacttgc agaaaaagga gttggacaga atcttaagct tacaggaggc ttgttcagca gaggagtcgg gcactataca
cagatggtat ggcaagaaac cgttaagctt ggatgctatg tggaagcgtg ctcaaatatg tgttatgtgg tgtgccagta
cggtcctgct ggaaatatga tgggcaagga tatctacgag aaaggagaac cgtgttcgaa atgtgagaat
tgcgacaagg agaagggact ctgcagtgct tgattagttg tgttcagtga agctcattac gctcacatac tttaacaaat
cgtagtgatc tgtagttgct ttaatattca aataaacatg atgccagcaa aaaaaaaaaa aaa
(SEQ ID NO: 1)

B.

Met Ser Ser Ile Thr Cys Leu Val Leu Leu Ser Ile Ala Ala Tyr Ser Lys Ala Gly Cys Pro
Asp Asn Gly Met Ser Glu Glu Ala Arg Gln Lys Phe Leu Glu Leu His Asn Ser Leu Arg
Ser Ser Val Ala Leu Gly Gln Ala Lys Asp Gly Ala Gly Gly Asn Ala Pro Lys Ala Ala Lys
Met Lys Thr Met Ala Tyr Asp Cys Glu Val Glu Lys Thr Ala Met Asn Asn Ala Lys Gln
Cys Val Phe Lys His Ser Gln Pro Asn Gln Arg Lys Gly Leu Gly Glu Asn Ile Phe Met Ser
Ser Asp Ser Gly Lys Ala Lys Ala Ala Glu Gln Ala Ser Lys Ala Trp Phe Gly Glu Leu Ala
Glu Lys Gly Val Gly Gln Asn Leu Lys Leu Thr Gly Gly Leu Phe Ser Arg Gly Val Gly
His Tyr Thr Gln Met Val Trp Gln Glu Thr Val Lys Leu Gly Cys Tyr Val Glu Ala Cys Ser
Asn Met Cys Tyr Val Val Cys Gln Tyr Gly Pro Ala Gly Asn Met Met Gly Lys Asp Ile
Tyr Glu Lys Gly Glu Pro Cys Ser Lys Cys Glu Asn Cys Asp Lys Glu Lys Gly Leu Cys
Ser Ala
(SEQ ID NO: 2)

Figure 1 A and B

A.

```
AGCGTTCATCGACGACTCTTTCATCAAGCTCGTCGTCATGTGACATCGGTATCGCTTTC
GCGTCAGCCAACACTTCGTGAACGACTGATCGCAAGTGGCAGTTGGGAGGATTACCAGA
AACAACGCTACCATTATCAAAAGAAAATTCTAGCAAAATATGCTGCTAACAAAGCGTCA
AAGTTACAATCTGCAAACGAGATCGATGAATTGCTCCGGAACTATATGGATGCACAATA
CTATGGTGTCATCCAAATTGGGACTCCAGCTCAGAATTTCACTGTGATCTTCGACACGG
GTTCCTCAAATCTATGGGTACCGTCAAGAAAGTGTCCATTCTATGACATTGCATGTATG
CTTCATCATCGTTATGACTCCGGAGCCTCGTCAACCTGCAAGGAAGATGGGCGCAAGAT
GGCTATTCAGTATGGAACTGGATCTATGAAAGGATTCATTTCTAAGGATATTGTTTGTA
TTGCTGGAATTTGCGCTGAAGAACAACCTTTCGCGGAGGCTACAAGTGAACCTGGTCTT
ACATTTATCGCTGCTAAGTTTGATGGAATCCTTGGAATGGCATTCCCGGAAATTGCTGT
TCTCGGTGTAACTCCTGTCTTCCATACGTTCATTGAACAGAAGAAAGTTCCTAGCCCTG
TGTTTGCTTTCTGGCCGAATAGGAATCCAGAGTCGGAAATTGGAGGAGAGATTACCTTT
GGTGGTGTGGATACCCGACGTTATGTTGAACCAATTACATGGACACCAGTGACACGTCG
TGGATATTGGCAATTCAAAATGGATATGGTACAAGGTGGTTCATCGTCCATTGCGTGTC
CGAATGGATGCCAAGCTATCGCTGATACTGGCACTTCTCTTATTGCTGGACCGAAGGCA
CAGGTTGAGGCAATCCAGAAATATATCGGAGCAGAGCCGCTTATGAAAGGAGAATACAT
GATTCCTTGCGACAAAGTACCATCCCTTCCTGATGTTTCGTTCATCATCGATGGCAAGA
CGTTTACACTCAAAGGGGAAGATTACGTTCTAACCGTGAAAGCCGCTGGTAAATCAATC
TGTTTGTCTGGCTTCATGGGAATGGACTTCCCAGAGAAGATCGGCGAATTGTGGATCCT
TGGAGATGTTTTCATTGGAAAATACTACACCGTCTTCGATGTTGGTCAGGCACGTGTTG
GATTTGCTCAAGCAAAGTCAGAAGATGGATTCCCTGTTGGGACCCCCGTTCGAACATTC
AGACAGCTTCAGGAAGACAGCGATAGCGACGAGGACGATGTATTTACTTTTTAA
(SEQ ID NO: 3)
```

B.

```
SVHRRLFHQARRHVTSVSLSRQPTLRERLIASGSWEDYQKQRYHYQKKILAKYAANKAS
KLQSANEIDELLRNYMDAQYYGVIQIGTPAQNFTVIFDTGSSNLWVPSRKCPFYDIACM
LHHRYDSGASSTCKEDGRKMAIQYGTGSMKGFISKDIVCIAGICAEEQPFAEATSEPGL
TFIAAKFDGILGMAFPEIAVLGVTPVFHTFIEQKKVPSPVFAFWPNRNPESEIGGEITF
GGVDTRRYVEPITWTPVTRRGYWQFKMDMVQGGSSSIACPNGCQAIADTGTSLIAGPKA
QVEAIQKYIGAEPLMKGEYMIPCDKVPSLPDVSFIIDGKTFTLKGEDYVLTVKAAGKSI
CLSGFMGMDFPEKIGELWILGDVFIGKYYTVFDVGQARVGFAQAKSEDGPPVGTPVRTF
RQLQEDSDSDEDDVFTF
(SEQ ID NO: 4)
```

Figure 2A and B

A.
GGCACGAGGGGAGATGGCTCGACTTGTATTCCTACTCGTACTATGTACTCTGGCTGCAC
AAGCGTTCATCGACGACTCTTTCATCAAGCTCGTCGTCATGTGACATCGGTATCGCTTT
CGCGTCAGCCAACACTTCGTGAACGACTGATCGCAAGTGGCAGTTGGGAGGATTACCAG
AAACAACGCTACCATTATCGAAAGAAAATTCTAGCAAATATGCTGCTAACAAAGCGTC
AAAGTTACAATCTGCAAACGAGATCGATGAATTGCTCCGGAACTATATGGATGCACAAT
ACTATGGTGTCATCCAAATTGGGACTCCAGCTCAGAATTTCACTGTGATCTTCGACACG
GGTCCTCAAATCTATGGGTACCGTCAAGAAAGTGTCCATTCTATGACATTGCATGTAT
GCTTCATCATCGTTATGACTCCGGAGCCTCGTCAACCTACAAGGAAGATGGGCGCAAGA
TGGCTATTCAGTATGGAACTGGATCTATGAAAGGATTCATTTCTAAGGATATTGTTTGT
ATTGCTGGAATTTGCGCTGAAGAACAACCTTTCGCGGAGGCTACAAGTGAACCTGGTCT
TACATTTATCGCTGCTAAGTTTGATGGAATCCTTGGAATGGCATTCCCGGAAATTGCTG
TTCTCGGTGTAACTCCTGTCTTCCATACGTTCATTGAACAGAAGAAAGTTCCTAGCCCT
GTGTTTGCTTTCTGGCTGAATAGGAATCCAGAGTCGGAAATTGGAGGAGAGATTACCTT
TGGTGGTGTGGATACCCGACGTTATGTTGAACCAATTACATGGACACCAGTGACACGTC
GTGGATATTGGCAATTCAAAATGGATATGGTACAAGGTGGTTCATCGTCCATTGCGTGT
CCGAATGGATGCCAAGCTATCGCTGATACTGGCACTTCTCTTATTGCTGGACCGAAGGC
ACAGGTTGAGGCAATCCAGAAATATATCGGAGCAGAGCCGCTTATGAAAGGAGAATACA
TGATTCCTTGCGACAAAGTACCATCCCTTCCTGATGTTTCGTTCATCATCGATGGCAAG
ACGTTTACACTCAAAGGGGAAGATTACGTTCTAACCGTGAAAGCCGCTGGTAAATCAAT
CTGTTTGTCTGGCTTCATGGGAATGGACTTCCCAGAGAAGATCGGCGAATTGTGGATCC
TTGGAGATGTTTTCATTGGAAAATACTACACCGTCTTCGATGTTGGTCAGGCACGTGTT
GGATTTGCTCAAGCAAAGTCAGAAGATGGATTCCCTGTTGGCACCCCCGTTCGAACATT
CAGACAGCTTCAGGAAGACAGCGATAGCGACGAGGACGATGTATTTACTTTTTAAGTAG
TGTTAACATCTCCAACGTGCTCTGTTACTTCTACGTGTACCATGTTTCACGTGTTTGCT
CATTTGATAAATTATTATCTTCCCT
(SEQ ID NO: 5)

B.
MARLVFLLVLCTLAAASVHRRLFHQARRHVTSVSLSRQPTLRERLIASGSWEDYQKQRY
HYRKKILAKYAANKASKLQSANEIDELLRNYMDAQYYGVIQIGTPAQNFTVIFDTGSSN
LWVPSRKCPFYDIACMLHHRYDSGASSTYKEDGRKMAIQYGTGSMKGFISKDIVCIAGI
CAEEQPPAEATSEPGLTFIAAKFDGILGMAFPEIAVLGVTPVFHTFIEQKKVPSPVFAF
WLNRNPESEIGGEITFGGVDTRRYVEPITWTPVTRGYWQFKMDMVQGGSSSIACPNGC
QAIADTGTSLIAGPKAQVEAIQKYIGAEPLMKGEYMIPCDKVPSLPDVSFIIDGKTFTL
KGEDYVLTVKAAGKSICLSGPMGMDFPEKIGELWILGDVFIGKYYTVPDVGQARVGFAQ
AKSEDGFPVGTPVRTFRQLQEDSDSDEDDVFTF*
(SEQ ID NO: 6)

Figure 3 A and B

TCTGTTCACAGAAGATTGTTTCATCAAGCTAGAAGACACGTTACTTCAGTTTCC
TTGTCCAGACAACCAACTTTGAGAGAGAGATTGATTGCTTCAGGTTCATGGAAGACTAC
CAAAAACAAAGATATCATTACAGAAAGAAGATTTTGGCTAAGTACGCTGCTAATAAGGCT
TCTAAGTTGCAATCTGCTAACGAGATTGATGAATTGTTGAGAAATTATATGGATGCTCAA
TATTATGGAGTTATTCAAATTGGAACACCAGCTCAAAATTTTACTGTTATTTTCGACACT
GGATCCTCAAACTTGTGGGTTCCTTCAAGAAAATGTCCTTTCTATGACATTGCTTGTATG
TTGCACCACAGATACGACTCTGGAGCTTCCTCCACATACAAAGAAGATGGAAGAAAGATG
GCTATTCAATATGGTACAGGATCCATGAAAGGTTTCATTTCCAAAGACATTGTTTGTATT
GCTGGAATTTGTGCTGAGGAACAACCTTTTGCTGAGGCTACTTCAGAGCCAGGATTGACT
TTCATTGCTGCTAAGTTTGATGGAATTTTGGGAATGGCTTTCCCTGAAATTGCTGTTTTG
GGAGTTACACCTGTTTTCCACACTTTTATTGAGCAAAAGAAGGTTCCATCACCAGTTTTT
GCTTTTTGGTTGAATAGAAATCCTGAGTCTGAGATTGGAGGAGAAATTACTTTTGGTGGA
GTTGATACTAGAAGATATGTTGAACCTATTACTTGGACACCTGTTACAAGAAGACGTTAT
TGGCAATTCAAAATGGATATGGTTCAAGGTGGATCTTCTTCTATTGCTTGTCCTAACGGT
TGTCAAGCTATTGCTGACACTGGAACTTCCTTGATTGCTGGTCCAAAGGCTCAAGTTGAA
GCTATTCAAAAGTATATTGGTGCTGAGCCATTGATGAAAGGTGAATACATGATTCCATGT
GATAAAGTTCCTTCTTTGCCAGACGTTTCCTTTATTATTGACGGAAAAACTTTTACTTTG
AAAGGAGAGGACTACGTTTTGACTGTTAAAGCTGCTGGAAAGTCTATTTGTTTGTCTGGT
TTTATGGGTATGGATTTTCCAGAAAAGATTGGAGAATTGTGGATTTTGGGAGATGTTTTC
ATTGGTAAATACTATACTGTTTTTGATGTTGGTCAAGCTAGAGTTGGTTTCGCTCAAGCT
AAATCTGAGGATGGTTTCCCAGTTGGAACTCCAGTTAGAACTTTTAGACAATTGCAAGAA
GATTCTGATTCAGACGAAGATGACGTTTTTACTTTT
(SEQ ID NO: 9)

B.

SVHRRLFHQARRHVTSVSLSRQPTLRERLIASGSWEDYQKQRYHYRKKILAKYAANKAS
KLQSANEIDELLRNYMDAQYYGVIQIGTPAQNFTVIFDTGSSNLWVPSRKCPFYDIACM
LHHRYDSGASSTYKEDGRKMAIQYGTGSMKGFISKDIVCIAGICAEEQPFAEATSEPGL
TFIAAKFDGILGMAFPEIAVLGVTPVFHTFIEQKKVPSPVFAFWLNRNPESEIGGEITF
GGVDTRRYVEPITWTPVIRRGYWQFKMDMVQGGSSSIACPNGCQAIADTGTSLIAGPKA
QVEAIQKYIGAEPLMKGEYMIPCDKVPSLPDVSFIIDGKTFTLKGEDYVLTVKAAGKSI
CLSGFMGMDFPEKIGELWILGDVFIGKYYTVFDVGQARVGFAQAKSEDGFPVGTPVRTF
RQLQEDSDSDEDDVFT
(SEQ ID NO: 10)

Figure 5 A and B

A.
TCTGTTCACAGAAGATTGTTTCATCAAGCTAGAAGACACGTTACTTCAGTTTCC
TTGTCCAGACAACCAACTTTGAGAGAGAGATTGATTGCTTCAGGTTCATGGGAAGACTAC
CAAAAACAAAGATATCATTACAGAAAGAAGATTTTGGCTAAGTACGCTGCTAATAAGGCT
TCTAAGTTGCAATCTGCTAACGAGATTGATGAATTGTTGAGAAATTATATGGATGCTCAA
TATTATGGAGTTATTCAAATTGGAACACCAGCTCAAAATTTTACTGTTATTTTCGCCACT
GGATCCTCAAACTTGTGGGTTCCTTCAAGAAAATGTCCTTTCTATGACATTGCTTGTATG
TTGCACCACAGATACGACTCTGGAGCTTCCTCCACATACAAAGAAGATGGAAGAAAGATG
GCTATTCAATATGGTACAGGATCCATGAAAGGTTTCATTTCCAAAGACATTGTTTGTATT
GCTGGAATTTGTGCTGAGGAACAACCTTTTGCTGAGGCTACTTCAGAGCCAGGATTGACT
TTCATTGCTGCTAAGTTTGATGGAATTTTGGGAATGGCTTTCCCTGAAATTGCTGTTTTG
GGAGTTACACCTGTTTTCCACACTTTTATTGAGCAAAAGAAGGTTCCATCACCAGTTTTT
GCTTTTTGGTTGAATAGAAATCCTGAGTCTGAGATTGGAGGAGAAATTACTTTTGGTGGA
GTTGATACTAGAAGATATGTTGAACCTATTACTTGGACACCTGTTACAAGAAGAGGTTAT
TGGCAATTCAAAATGGATATGGTTCAAGGTGGATCTTCTTCTATTGCTTGTCCTAACGGT
TGTCAAGCTATTGCTGACACTGGAACTTCCTTGATTGCTGGTCCAAAGGCTCAAGTTGAA
GCTATTCAAAAGTATATTGGTGCTGAGCCATTGATGAAAGGTGAATACATGATTCCATGT
GATAAAGTTCCTTCTTTGCCAGACGTTTCCTTTATTATTGACGGAAAAACTTTTACTTTG
AAAGGAGAGGACTACGTTTTGACTGTTAAAGCTGCTGGAAAGTCTATTTGTTTGTCTGGT
TTTATGGGTATGGATTTTCCAGAAAAGATTGGAGAATTGTGGATTTTGGGAGATGTTTTC
ATTGGTAAATACTATACTGTTTTTGATGTTGGTCAAGCTAGAGTTGGTTTCGCTCAAGCT
AAATCTGAGGATGGTTTCCCAGTTGGAACTCCAGTTAGAACTTTTAGACAATTGCAAGAA
GATTCTGATTCAGACGAAGATGACGTTTTTACTTTT
(SEQ ID NO: 11)

B.
SVHRRLFHQARRHVTSVSLSKQPTLRERLIASGSWEDYQKQRYHYRKKILAKYAANKAS
KLQSANEIDELLRNYMDAQYYGVIQIGTPAQNFTVIFATGSSNLWVPSRKCPFYDIACL
HHRYDSGASSTYKEDGRKMAIQYGTGSMKGFISKDIVCIAGICAEEQPFAEATSEPGLT
FIAAKFDGILGMAFPEIAVLGVTPVFHTFIEQKKVPSPVFAFWLNRNPESEIGGEITFG
GVDTRRYVEPITWTPVIRRGYWQFKMDMVQGGSSSIACPNGCQAIADTGTSLIAGPKAQ
VEAIQKYIGAEPLMKGEYMIPCDKVPSLPDVSFIIDGKTFTLKGEDYVLTVKAAGKSIC
LSGFMGMDFPEKIGELWILGDVFIGKYYTVFDVGQARVGFAQAKSEDGFPVGTPVRTFR
QLQEDSDSDEDDVFT
(SEQ ID NO: 12)

Figure 6A and B

A.

```
TCTGTTCACAGAAGATTGTTTCATCAAGCTAGAAGACACGTTACTTCAGTTTCC
TTGTCCAGACAACCAACTTTGAGAGAGAGATTGATTGCTTCAGGTTCATGGGAAGACTAC
CAAAAACAAAGATATCATTACAGAAAGAAGATTTTGGCTAAGTACGCTGCTAATAAGGCT
TCTAAGTTGCAATCTGCTAACGAGATTGATGAATTGTTGAGAAATTATATGGATGCTCAA
TATTATGGAGTTATTCAAATTGGAACACCAGCTCAAAATTTTACTGTTATTTTCGACACT
GGATCCTCAAACTTGTGGGTTCCTTCAAGAAAATGTCCTTTCTATGACATTGCTTGTATG
TTGCACCACAGATACGACTCTGGAGCTTCCTCCACATACAAAGAAGATGGAAGAAAGATG
GCTATTCAATATGGTACAGGATCCATGAAAGGTTTCATTTCCAAAGACATTGTTTGTATT
GCTGGAATTTGTGCTGAGGAACAACCTTTTGCTGAGGCTACTTCAGAGCCAGGATTGACT
TTCATTGCTGCTAAGTTTGATGGAATTTTGGGAATGGCTTTCCCTGAAATTGCTGTTTTG
GGAGTTACACCTGTTTTCCACACTTTTATTGAGCAAAAGAAGGTTCCATCACCAGTTTTT
GCTTTTTGGTTGAATAGAAATCCTGAGTCTGAGATTGGAGGAGAAATTACTTTTGGTGGA
GTTGATACTAGAAGATATGTTGAACCTATTACTTGGACACCTGTTACAAGAAGAGGTTAT
TGGCAATTCAAAATGGATATGGTTCAAGGTGGATCTTCTTCTATTGCTTGTCCTAACGGT
TGTCAAGCTATTGCTGCCACTGGAACTTCCTTGATTGCTGGTCCAAAGGCTCAAGTTGAA
GCTATTCAAAAGTATATTGGTGCTGAGCCATTGATGAAAGGTGAATACATGATTCCATGT
GATAAAGTTCCTTCTTTGCCAGACGTTTCCTTTATTATTGACGGAAAAACTTTTACTTTG
AAAGGAGAGGACTACGTTTTGACTGTTAAAGCTGCTGGAAAGTCTATTTGTTTGTCTGGT
TTTATGGGTATGGATTTTCCAGAAAAGATTGGAGAATTGTGGATTTTGGGAGATGTTTTC
ATTGGTAAATACTATACTGTTTTTGATGTTGGTCAAGCTAGAGTTGGTTTCGCTCAAGCT
AAATCTGAGGATGGTTTCCCAGTTGGAACTCCAGTTAGAACTTTTAGACAATTGCAAGAA
GATTCGATTCAGACGAAGATGACGTTTTTACTTTT
```
(SEQ ID NO: 13)

B.

```
SVHRRLFHQARRHVTSVSLSRQPTLRERLIASGSWEDYQKQRYHYRKKILAKYAANKAS
KLQSANEIDELLRNYMDAQYYGVIQIGTPAQNFTVIFDTGSSNLWVPSRKCPFYDIACM
LHHRYDSGASSTYKEDGRKMAIQYGTGSMKGPISKDIVCIAGICAEEQPFAEATSEPGL
TFIAAKFDGILGMAFPEIAVLGVTPVFHTFIEQKKVPSPVFAFWLNRNPESEIGGEITF
GGVDTRRYVEPITWTPVTRRGYWQFKMDMVQGGSSSIACPNGCQAIAATGTSLIAGPKA
QVEAIQKYIGAEPLMKGEYMIPCDKVPSLPDVSFIIDGKTFTLKGEDYVLTVKAAGKSI
CLSGFMGMDFPEKIGELWILGDVFIGKYYTVFDVGQARVGFAQAKSEDGFPVGTPVRTF
RQLQEDSDSDEDDVFT
```
(SEQ ID NO: 14)

Figure 7A and B

A.
TCTGTTCACAGAAGATTGTTTCATCAAGCTAGAAGACACGTTACTTCAGTTTCC
TTGTCCAGACAACCAACTTTGAGAGAGAGATTGATTGCTTCAGGTTCATGGAAGACTAC
CAAAAACAAAGATATCATTACAGAAAGAAGATTTTGGCTAAGTACGCTGCTAATAAGGCT
TCTAAGTTGCAATCTGCTAACGAGATTGATGAATTGTTGAGAAATTATATGGATGCTCAA
TATTATGGAGTTATTCAAATTGGAACACCAGCTCAAAATTTTACTGTTATTTTCGCCACT
GGATCCTCAAACTTGTGGGTTCCTTCAAGAAAATGTCCTTTCTATGACATTGCTTGTATG
TTGCACCACAGATACGACTCTGGAGCTTCCTCCACATACAAAGAAGATGGAAGAAAGATG
GCTATTCAATATGGTACAGGATCCATGAAAGGTTTCATTTCCAAAGACATTGTTTGTATT
GCTGGAATTTGTGCTGAGGAACAACCTTTTGCTGAGGCTACTTCAGAGCCAGGATTGACT
TTCATTGCTGCTAAGTTTGATGGAATTTTGGGAATGGCTTTCCCTGAAATTGCTGTTTTG
GGAGTTACACCTGTTTTCCACACTTTTATTGAGCAAAAGAAGGTTCCATCACCAGTTTTT
GCTTTTTGGTTGAATAGAAATCCTGAGTCTGAGATTGGAGGAGAAATTACTTTTGGTGGA
GTTGATACTAGAAGATATGTTGAACCTATTACTTGGACACCTGTTACAAGAAGAGGTTAT
TGGCAATTCAAAATGGATATGGTTCAAGGTGGATCTTCTTCTATTGCTTGTCCTAACGGT
TGTCAAGCTATTGCTGCCACTGGAACTTCCTTGATTGCTGGTCCAAAGGCTCAAGTTGAA
GCTATTCAAAAGTATATTGGTGCTGAGCCATTGATGAAAGGTGAATACATGATTCCATGT
GATAAAGTTCCTTCTTTGCCAGACGTTTCCTTTATTATTGACGGAAAAACTTTTACTTTG
AAAGGAGAGGACTACGTTTTGACTGTTAAAGCTGCTGGAAAGTCTATTTGTTTGTCTGGT
TTTATGGGTATGGATTTTCCAGAAAAGATTGGAGAATTGTGGATTTTGGGAGATGTTTTC
ATTGGTAAATACTATACTGTTTTTGATGTTGGTCAAGCTAGAGTTGGTTTCGCTCAAGCT
AAATCTGAGGATGGTTTCCCAGTTGGAACTCCAGTTAGAACTTTTAGACAATTGCAAGAA
GATTCTGATTCAGACGAAGATGACGTTTTTACTTTT
(SEQ ID NO: 15)

B.

SVHRRLFHQARRHVTSVSLSRQPTLRERLIASGSWEDYQKQRYHYRKKILAKYAANKAS
KLQSANEIDELLRNYMDAQYYGVIQIGTPAQNFTVIFATGSSNLWVPSRKCPFYDIACM
LHHRYDSGASSTYKEDGRKMAIQYGTGSMKGFISKDIVCIAGICAEEQPFAEATSEPGL
TFIAAKFDGILGMAFPEIAVLGVTPVFHTFIEQKKVPSPVFAFWLNRNPESEIGGEITF
GGVDTRRYVEPITWTPVTRRGYWQFKMDMVQGGSSSIACPNGCQAIAATGTSLIAGPKA
QVEAIQKYIGAEPLMKGEYMIPCDKVPSLPDVSFIIDGKTFTLKGEDYVLTVKAAGKSI
CLSGFMGMDFPEKIGELWILGDVFIGKYYTVPDVGQARVGFAQAKSEDGFPVGTPVRTF
RQLQEDSDSDEDDVFT
(SEQ ID NO: 16)

Figure 8A and B

A.

AAGTGATGGTTCATTACAAGTTAACCTACTTCGCTATACGTGGAGCCGGAGAATGTGCA
AGACAGATCTTCGCACTTGCCGATCAGGAATTCGAGGATGTCCGTTTAGACAAAGAGCA
GTTCGCAAAAGTGAAGCCTGATTTGCCTTTCGGACAGGTTCCAGTCCTTGAAGTCGATG
GCAAGCAACTGGCTCAATCCCTTGCGATTTGCCGCTATCTGGCCAGGCAGTTCGGTTTC
GCAGGCAAATCAACGTTCGATGAAGCCGTAGTCGACTCTTTAGCAGACCAGTATTCTGA
CTATCGCGTCGAGATCAAGTCGTTCTTCTACACTGTCATTGGAATGCGAGAAGGTGATG
TGGAGCAACTCAAAAAAGAAGTGTTACTTCCTGCTCGCGATAAATTCTTCGGATTCATC
ACTAAATTCCTTAAGAAAAGCCCTTCTGGTTTCCTTGTCGGTGACTCACTGACGTGGGT
GGACCTCTTGGTCTCGGAGCACAATGCTACAATGCTTACGTTTGTACCAGAGTTCCTTG
AAGGCTATCCTGAAGTAAAAGAGCACATGGAAAAGATACGAGCGATTCCGAAACTGAAG
AAATGGATCGAAACCCGACCAGAGACATTGTTCTAATTTGTAGTGATGTTATCCTACTT
GTTCTGATCTATTTGAGTTATCTTCATTGTCAACAGAAATTCATTATTGGCTTGCAGTA
ATAACCGTTATTCAGGCACTTGAAATCCACTAGTTATTTCTTTCCATAAGCTACATTCT
CAGATGTATGTATGAGGATAAA
(SEQ ID NO: 17)

B.

MVHYKLTYFAIRGAGECARQIFALADQEPEDVRLDKEQFAKVKPDLPFGQVPVLEVDGK
QLAQSLAICRYLARQFGPAGKSTFDEAVVDSLADQYSDYRVEIKSFFYTVIGMREGDVE
QLKKEVLLPARDKFPGFITKFLKKSPSGFLVGDSLTWVDLLVSEHNATMLTFVPEFLEG
YPEVKEHMEKIRAIPKLKKWIETRPETLF*
(SEQ ID NO: 18)

Figure 9A and B

A.

GATGGTCCATTACAAGCTCACTTACTTCGCAGGCCGTGGACTTGCTGAACCTATTCGCC
AGATTTTCGCCCTTGCTGGTCAAAAATATGAAGATGTTCGTTATACCTTTCAGGAATGG
CCCAAACACAAGGATGAAATGCCATTTGGTCAAATACCAGTGTTGGAAGAGGATGGTAA
ACAACTAGCGCAATCATTCGCTATCGCTCGTTACCTTTCCAGAAAATTCGGTTTTGCCG
GAAAAACTCCTTTCGAAGAAGCCTTAGTCGACTCGGTTGCTGACCAATACAAGGACTAC
ATCAATGAGATCCGTCCATACCTCAGGGTCGTTGCAGGAGTCGATCAGGGAGATCCGGA
GAAGCTTTTCAAGGAACTGCTCCTTCCAGCTCGTGAGAAATTCTTCGGTTTCATGAAAA
AATTCCTTGAAGAGCAAATCTGGTTACCTCGTTGGTGATTCGGTGACATACGCTGAC
TTGTGCTTAGCCGAGCACACATCTGGTATCGCTGCGAAGTTCCCCAGTATCTATGATGG
TTTCCCTGAGATCAAAGCTCATGCCCAAAAGGTTCGATCGATACCGGCTCTGAAAAAAT
GGATTGAAACTCGACCTGAGACTAAATTCTAATTTTTCCCGAGTTGTTTACATATCAGT
TCAAGAGGGTATAAAATAAAGGTGTTTTTCTTTTAAAAAAAAATGGTCCTTCTCTCGAT
TGCAGCGTACTTCAAAGCCGGTTGT
(SEQ ID NO: 19)

B.

MVHYKLTYFAGRGLAEPIRQIFALAGQKYEDVRYTFQEWPKHKDEMPFGQIPVLEEDGK
QLAQSFAIARYLSRKFGFAGKTPFEEALVDSVADQYKDYINEIRPYLRVVAGVDQGDPE
KLFKELLLPAREKFFGFMKKFLEKSKSGYLVGDSVTYADLCLAEHTSGIAAKFPSIYDG
PPEIKAHAEKVRSIPALKKWIETRPETKF*
(SEQ ID NO: 20)

Figure 10A and B

A.

```
GAAAGGTTTAATTACCCAAGTTTGAGAATGGTTCACTACAAGCTAACCTACTTCGACGG
ACGCGGTGCCGCTGAAATTATTCGTCAGATTTTTGTCCTTGCTGGTCAAGAATACGAGG
ATATCCGTCTTAGTCACGACGAATGGCCCAAGTACAAGAACGAAATGCCATTCGGTCAA
TTGCCAGTGTTGGAAGTCGACGGCAAAAAGCTTGCACAATCTTTCGCTATCGCCCGCTT
CGTGGCCAAAAAATTCGGGTTTGCTGGAAAGTGTCCGTTTGAAGAGGCTCTGGTTGACT
CGATCACCGATCAATACAAGGACTTCATCAATGAGATCCGCCCATTCTTACGAGTTGCT
ATGGGTTTCGCAGAGGGAGATCTGGAGAAGCTCAGCAACGAAGTCTTCTTGCCAGCTCG
TGAAAAGTTCTTCGGATTCATGACAAACTTCCTCAAGGAGAGCAAGTCTGGTTATCTCG
TTGGTGATTCATTGACGTTCGCAGACCTGTACCTAGCTGAATGCGCATCTGAATTCGCT
AAGAAAACTCCGACAATCTTCGACGGATTCCCAGAAATCAAAGCCCATGCCGAAAAAGT
TCGCTCGAACCCAGCTCTCAAGAAATGGATTGAAACCCGACCAGAAACTAAATTCTAAA
TCCTCGCAACTACTTGGTTATTTCCATCGATTCCCGTGAATAAAATTATTGCTCTCAAA
AAAAAAAAAAAAAAAA
```
(SEQ ID NO: 21)

B.

```
MVHYKLTYFDGRGAAEIIRQIFVLAGQEYEDIRLSHDEWPKYKNEMPFGQLPVLEVDGK
KLAQSFAIAREVAKKFGFAGKCPFEEALVDSITDQYKDFINEIRPFLRVAMGFAEGDLE
KLSNEVPLPAREKFFGFMTNFLKESKSGYLVGDSLTFADLYLAECASEFAKKTPTIFDG
FPEIKAHAEKVRSNPALKKWIETRPETKF*
```
(SEQ ID NO: 22)

Figure 11A and B

A.

```
GTTAAAGCCGTGTAAGCAACAGGGTTCTTTGTGATGTTAACTCTCGCTGCACTTCTGAT
TTCTGTTTCGCTGGTTGAGCCGACAGGCATAGGTGAGTTTCTTGCTCAACCAGCACCTG
CATATGCTAGAAGACTCACAGGGCAGGCCCTTGTTGACTACGTCAATTCGCACCACTCA
TTGTACAAGGCCAAATATTCACCAGATGCTCAAGAACGCATGAAATCTAGAATTATGGA
TTTGAGTTTCATGGTTGATGCGGAAGTCATGATGGAAGAAATGGACCAGCAGGAGGATA
TAGATCTCGCTGTTTCTTTACCTGAAAGTTTCGACGCTCGTGAAAAATGGCCAGAATGT
CCTTCAATAGGATTAATCCGTGATCAGTCCGCCGGTGGAGGATGTTGGGCAGTATCCTC
AGCAGAGGTGATGACCGACAGGATCTGTATACAATCAAATGGAACAAAGCAGGTGTATG
TTCCGAAACGGATATCTTATCATGCTGTGGACAACGTTGCGGTAGCGGGTGTACCTCA
GGTGTGCCACGTCAAGCTTTCAACTATGCAATTCGTAAAGGTGTTTGCAGTGGAGGACC
ATATGGAACGAAGGGTGTTTGCAAACCCTATCCTTTCTATCCATGCGGCTATCATGCTC
ATCTGCCATATTATGGACCATGTCCAGATGGTATGTGGCCTACGCCAACATGCGAAAAG
GCATGTCAATCCGACTATACTGTTCCGTACAACGATGACAGGATCTTCGGCAGCAAAAC
TATTGTCTTGACGGGAGAGGAAAAAATTAAGCGAGAGATTTTCAATAACGGACCATTGG
TAGCCACGTATACAGTTTACGAAGATTTCGCTTATTACAAGAATGGAATTTACATGACT
GGTCTCGGTAGAGCGACAGGCGCACATGCAGTCAAAATTATTGGCTGGGGTGAAGAAAA
TGGAGTCAAGTATTGGTTGATTGCAAACTCGTGGAACACTGATTGGGGAGAGAATGGCT
TCTTCCGCATGCTTCGTGGAACAAACCTTTGCGATATTGAACTAAGCGCGACTGGAGGA
ACGTTCAAGGTGTGAACGTGATCGAAAAGAACGATTTTGAACAAAATCTTCCCGTATT
GTCATCAAAAAAA
```
(SEQ ID NO: 23)

B.

```
MLTLAALLISVSLVEPTGIGEFLAQPAFAYARRLTGQALVDYVNSHHSLYKAKYSPDAQ
ERMKSRIMDLSFMVDAEVMMEEMDQQEDIDLAVSLPESFDAREKWPECPSIGLIRDQSA
GGGCWAVSSAEVMTDRICIQSNGTKQVYVSETDILSCCGQRCGSGCTSGVPEQAFNYAI
RKGVCSGGPYGTKGVCKPYPFYPCGYHAHLPYYGPCPDGMWPTPTCEKACQSDYTVPYN
DDRIFGSKTIVLTGEEKIKREIFNNGPLVATYTVYEDFAYYKNGIYMTGLGRATGAHAV
KIIGWGEENGVKYWLIANSWNTDWGENGFFRMLRGTNLCDIELSATGGTFKV*
```
(SEQ ID NO: 24)

Figure 12A and B

A.

```
ttaattctta ttgctctggt ggtgacggcg ttggctcaac agccgctttc
actaaaggag tatctggaac agccgatacc agaggaggca gagaatcttt
ccggagaagc gtttgcggag tttctgaaca aacgacaatc gttttcacg
gctaagtaca cgccaaatgc tttaaacatt cttaaaatgc gtgtgatgga
atcgagattc ctggacaatg aagaaggtga atgctaaaa gaggaggaca
tggatttcag tgaagaaatt cctgttagtt tgatgctcg agacaaatgg
cccaaatgca cctccatagg atttatccgt gatcaatcac actgtggttc
atgctgggca gtatcgtcag cagaaacgat gtcagatcga ctctgcgtgc
aatcaaacgg tacaattaag gtacttctat ccgatacgga catccttgcc
tgttgcccga attgtggtgc tggatgtgga ggaggcaca caattcgagc
gtgggaatat tttaagaaca caggcgtttg cactggcgga ctatatggaa
caaaggattc ctgcaaacca tacgctttct atccatgtaa agacgaaagt
tacggaaagt gccccaagga ttctttcca acaccaaaat gtcgaaaaat
ttgtcagtat aaatacagta agaagtacgc cgacgacaaa tactacgcga
attccgcata tcgaattcca cagaatgaga cgtggatcaa attggagatc
atgagaaacg ggcctgtgac agcatcattc aggatttatc cggatttgg
gttttacgaa aaaggagttt atgtgacttc aggcggaagg gaactaggtg
ggcacgcgat taaaatcatt ggatggggaa cggaaaaagt aaacggaact
gacctacctt actggttgat tgctaactct tggggtactg actggggaga
gaataacggc tatttccgca tacttcgcgg acaaaatcac tgccaaatag
aacagaaagt tatcgccggt atgataaaag taccacaacc gaaatccgcc
ggtccaccac ttcaacccaa tccttcaagc tgaaccaagt tgtagtattg
tccccatcaa tccaagcatt tcttggggtg atacttttac gaataaaaac
tacattataa aaaaaaaaa aaaaaaa
```
(SEQ ID NO: 25)

B.

```
LILIALVVTA LAQQFLSLKE YLEQPIPEEA ENLSGEAFAE FLNKRQSFPT AKYTPNALNI
LKMRVMESRF LDNEEGEMLK EEDMDFSEEI PVSFDARDKW PKCTSIGFIR DQSHCGSCWA
VSSAETMSDR LCVQSNGTIK VLLSDTDILA CCPNCGAGCG GGHTIRAWEY FKNTGVCTGG
LYGTKDSCKP YAFYPCKDES YGECPKDSFP TPKCRKICQY KYSKKYADDK YYANSAYRIP
QNETWIKLEI MRNGPVTASF RIYPDFGFYE KGVYVTSGGR ELGGHAIKII GWGTEKVNGT
DLPYWLIANS WGTDWGENNG YFRILRGQNH CQIEQKVIAG MIKVPQPKSA GPPLQPNPSS
```
(SEQ ID NO: 26)

Figure 13A and B

A.

```
tcgttgaggc gttatttcaa gcttctctcg cctcgatttc agattctcca
attgtttcag tgaatcgtgg aacagtcaat ctcacttttg tgagatccaa
tgaaagctaa ttttgcgttg gtcgtcgtcc ttctggcaat aaaccagtta
tatgcagatg agctgcttca caaacaagag tccgaacacg gacttagtgg
ccaagcgctc gttgactacg ttaattcgca ccaatcactt tcaaaacag
aatattcgcc aaccaatgaa caattcgtta agcccgtat aatggacata
aagtatatga ctgaggctag ccacaaatat ccagaaagg gcattaatct
gaacgttgaa ctccctgaaa ggtttgacgc acgtgaaaaa tggccacatt
gcgcctccat cggtctcatt cgcgatcact ctgcttgcgg atcgtgttgg
gctgtatcgg cagcgtcggt tatgtcagat cgactctgta tccagacgaa
cggcacaaac cagaagatcc tttcgtcggc ggacatcctt gcgtgttgtg
gagaagactg tggctcagga tgcgaaggcg gttatccgat tcaggcgtac
ttctacctgg aaaatactgg agtatgtagt ggaggagagt atcgagaaaa
gaatgtatgc aaaccatatc cctttatcc gtgtgacgga aactatggac
catgccccaa ggagggtgcg ttcgacactc caaagtgtcg gaaaatatgt
cagttccgat atcctgttcc atacgaagaa gataaagtgt ttggaaaaaa
ttcacacatc cttctgcaag acaacgaggc aagaatcaga caggaaattt
tcataaacgg accagtggga gctaattttt acgttttcga agactttata
cactacaagg aagggattta taagcagaca tatgggaaat ggataggagt
acatgcaatc aaacttattg gttgggcac agaaaatgga acagattatt
ggttggttgc taactcgtac aactacgact ggggagagaa tggcaccttc
cgcattcttc gtggaactaa tcactgtttg atagaatcac aagtgatcgc
aacggagatg attgtatgaa tgtctaatga acgattggtc gcatgccgat
ctctgaagta aaatgtgtta atcaaaaaaa a
```
(SEQ ID NO: 27)

B.

```
MKANFALVVVLLAINQLYADELLHKQESEHGLSGQALVDYVNSH
QSLFKTEYSPTNEQFVKARIMDIKYMTEASHKYPRKGINLNVELPERFDAREKWPHCA
SIGLIRDHSACGSCWAVSAASVMSDRLCIQTNGTNQFILSSADILACCGEDCGSGCEG
GYPIQAYFYLENTGVCSGGEYREKNVCKPYPFYPCDGNYGPCPKEGAFDTPKCRKICQ
FRYPVPYEEDKVFGKNSHILLQDNEARIREQEIFINGPVGANFYVFEDFIHYKEGIYKQ
TYGKWIGVHAIKLIGWGTENGTDYWLVANSYNYDWGENGTFRILRGTNHCLIESQVIA
TEMIV
```
(SEQ ID NO: 28)

Figure 14A and B

A.

```
tagataataa tcttttgca cgtcagagaa tttctttgat aaaaccacaa
ttaaacaatc tcagcgctgt aaacacgtgc aaaactactc gttcatttct
cttcactttc cctccaaaac caaacattca agagaagcat gataaccatc
attaccctat tgcttatcgc ttctacagtg aagtcactaa cagtggagga
gtacttggcc cgaccagtgc cggaatatgc cacaaactg acaggacaag
cctacgttga ctatgttaat cagcatcaat cattctacaa ggctgaatat
tccccgctgg ttgaacagta tgccaaagct gtgatgagat ctgagtttat
gacgaagccg aaccaaaatt atgtggtgaa ggacgtagat ctaaacatca
atcttccaga aaccttcgac gcaagggaaa aatggccaaa ctgcacatca
ataaggacaa ttcgcgatca gtccaattgt ggatcatgtt gggcagtatc
agcggcgtcg gtaatgtcag atcgtttatg catacagtcg aacggcacaa
tacagtcatg ggcttctgat acggatattc tatcatgttg ctggaattgc
ggaatgggat gcgatggagg tagaccgttt gcggcgttct ttttcgcgat
agacaatggt gtatgcactg gaggaccttt cagagagcca aacgtgtgca
aaccatacgc tttctatcca tgcggtcgcc accaaaacca gaatacttc
ggaccttgtc caaaagagct ctggcccact ccaaaatgtc ggaaaatgtg
tcaactaaaa tataatgtgg cctacaaaga cgataaaatt tacgggaatg
atgcatacag tctccctaac aatgagacac gaatcatgca agaaattttc
acaaatggac ctgtagtggg atcattcagc gtgtttgctg actttgcaat
ttataagaaa ggagtatatg tgagtaatgg aattcagcag aatggggctc
atgcagtcaa aattattggt tggggtgtgc aggatggact aaaatattgg
ttgattgcta attcctggaa caatgactgg ggagacgaag gctatgtccg
gttccttcgt ggagataacc actgtggaat tgaatcaagg gtggtgacag
gaactatgaa agtgtaaaac aataattagt cttttcctga cgatttcaaa
taaaatcttt gccactaaaa aaaaaaaaaa aaaaaa
```
(SEQ ID NO: 29)

B.

MITIITLLLIASTVKSLTVEEYLARPVPEYATKLTGQAYVDYVN
QHQSFYKAEYSPLVEQYAKAVMRSEFMTKPNQNYVVKDVDLNINLPETFDAREKWPNC
TSIRTIRDQSNCGSCWAVSAASVMSDRLCIQSNGTIQSWASDTDILSCCWNCGMGCDG
GRPFAAFFFAIDNGVCTGGPFREPNVCKPYAFYPCGRHQNQKYFGPCPKELWPTPKCR
KMCQLKYNVAYKDDKIYGNDAYSLPNNETRIMQEIFTNGPVVGSFSVFADFAIYKKGV
YVSNGIQQNGAHAVKIIGWGVQDGLKYWLIANSWNNDWGDEGYVRFLRGDNHCGIESR
VVTGTMKV
(SEQ ID NO: 30)

Figure 15A and B

A.

```
acttcaagcg atgttccgtc ctgctactgc cgtccttcta ttgttggccg
cgtccagcac atttgctgga ttttcgatg atgttggagg cttacccagt
ggtgtgggag attttttcac aaagcagttc aacaatgtga aggatctttt
tgctaaagat caagatactc ttgagaagaa tatcaatctg gtaaaggatc
tattgattgc cattaaggag aaggctaaga tgctggaacc gatggccaac
gaggctcaga agaagacatt agggcaggtg gacaactatc tcaatgaagt
tcaacagttc ggcgatcagg tagccaagga gggttctacg aaatttgagg
agaacaaagg gaaatggcag caaatgttga acgatatctt cgagaaaggt
ggactggaca gcgtgatgaa gttgctcaat ctgaagtccg gcggtcgctg
cacgttagcc gctgcactcg tcgctcccgt tgtgctcgcg ctcatccgct
aattcacttc taccgccgcc gactactgta gttaccctg tgcctgtgtg
tgatatgtgg atttgtgcat gatgtgtatc tatgatttgt gatttatttt
tctcttgtac ttccatgaat tcagctctgg tattctgaga cggaccaaca
tctccgcagt acttttttgt attgttatca tcaccgtaat cctgtgactg
gcgtaaaatg tttagttttc cgataaaata catttcgaaa aaaaaaaaa
aaaaaaaaa
```
(SEQ ID NO: 31)

B.

MFRPATAVLLLLAASSTFAGFFDDVGGLPSGVGDFFTKQFNNVK
DLFAKDQDTLEKNINLVKDLLIAIKEKAKMLEPMANEAQKKTLGQVDNYLNEVQQFGD
QVAKEGSTKFEENKGKWQQMLNDIFEKGGLDSVMKLLNLKSGGRCTLAAALVAPVVLA
LIR
(SEQ ID NO: 32)

Figure 16A and B

A.

AAAAGCCTCCATAGTCATGCTCAAGCTCGTTGCACTCGTTTGCCTGGTTGCAATCTGCT
TCGCTCAGGGACCACAAGGACCCCCTCCGTTCCTGCAAAGTGCTCCAGCGGCTGTTCAA
CAAGACTTCGACAAGCTCTTCGTCAATGCTGGCTCCAAGACTGATGCAGAAATCGACAA
AATGGTCCAAGATTGGGTTGGCAAACAAGATGCATCCATCAAGACCGCATTCGATGCGT
TCGTGAAGGAAGTGAAAGCCGCTCAAGCGCAAGGTGAAGCTGCCCATCAGGCTGCTATC
GCCAAGTTCAGCGCAGAGGCCAAAGCGGCTGATGCCAAGCTGAGCGCAATTGCGAACGA
CAGGTCGAAGACAAACGCGCAAAAGGGAGCTGAGATCGACTCGGTACTCAAGGGACTTC
CTCCAAATGTCCGCACAGAGATCGAAAACGCCATGAAAGGATAAGAAGTCTCTATTTTG
TATATATGAACCGATAAATATGCACAATAAAAAAAAAAAAAAAAAAAAAAAAAAAA
(SEQ ID NO: 33)

B.

MLKLVALVCLVAICFAQGPQGPPPFLQSAPAAVQQDFDKLFVNAGSKTDAEIDKMVQDW
VGKQDASIKTAFDAFVKEVKAAQAQGEAAHQAAIAKFSAEAKAADAKLSAIANDRSKTN
AQKGAEIDSVLKGLPPNVRTEIENAMKG*
(SEQ ID NO: 34)

Figure 17A and B

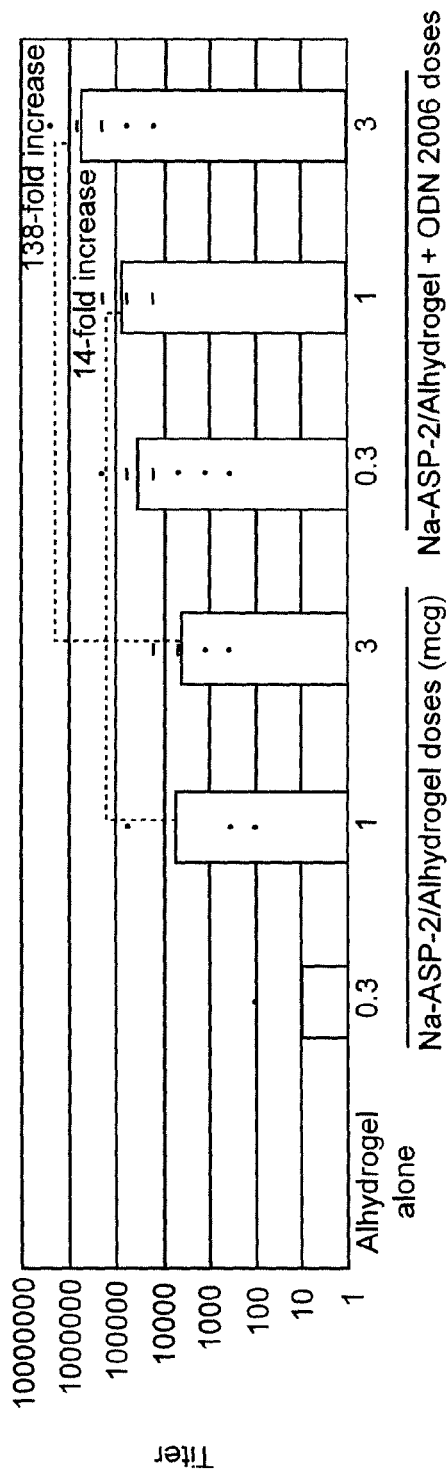
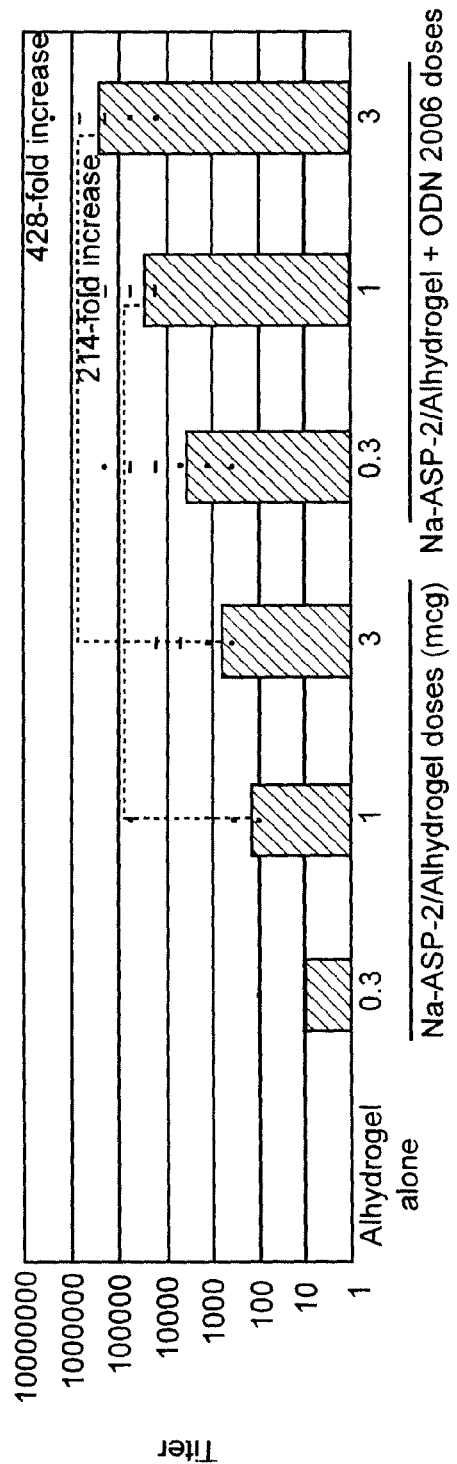
Figure 18A
Figure 18B

| Antigen | In vitro larval inhibition (0=2) | Worm burden reduction (0-2) | Fecal egg reduction (0-2) | Blood loss reduction (0-2) | Orthologous protective antigens (0-1) | Feasibility of expresson (0-2) | Immunoepidemiology (0-2) | Total Score (x10) |
|---|---|---|---|---|---|---|---|---|
| Lead Candidates | | | | | | | | |
| ASP-2 | 2 | 1 | 2 | 1 | 1 | 2 | TBD | 90 |
| SAA-2 | 1 | 1 | 2 | 2 | 1 | 2 | TBD | 90 |
| Back-up Candidates | | | | | | | | |
| SAA-1 | 1 | ND | ND | ND | 0 | 2 | TBD | ND |
| TMP-2 | ND | ND | ND | ND | 0 | 2 | TBD | ND |
| ASP-1 | ND | 0 | 0 | 0 | 1 | 1 | TBD | 20 |
| MTP-1 | 1 | 1 | 1 | 0 | 0 | 1 | TBD | 40 |

Figure 20

| Antigen | Known mechanism (0-2) | Worm Burden Reduction (0-2) | Fecal egg count reduction (0-2) | Blood loss reduction (0-2) | Orthologous protective antigens (0-1) | Feasibility of expresson (0-2) | Immunoepidemiology (0-2) | Total Score (x10) |
|---|---|---|---|---|---|---|---|---|
| Lead Candidates | | | | | | | | |
| APR-1 | 2 | 1 | 2 | 2 | 1 | 1 | TBD | 90 |
| GST-1 | 2 | 2 | 1 | 1 | 1 | 2 | TBD | 90 |
| Back-up Candidates | | | | | | | | |
| CP-2/3 | 2 | 0 | 2 | 1 | 1 | 1 | TBD | ND |
| Cys | 1 | 1 | 1 | 0 | 1 | 2 | TBD | 60 |
| MEP-1 | 2 | 0 | 1 | 0 | 1 | 1 | TBD | 50 |
| TMP-1 | 1 | 0 | 1 | 0 | 0 | 2 | TBD | 40 |
| FAA-1 | 1 | 0 | 0 | 0 | 0 | 2 | | 30 |
| ASP-4-6 | 1 | 0 | 0 | 0 | 0 | 1 | | 20 |
| C-Lectin | 1 | 0 | 0 | 0 | 0 | 1 | | 20 |
| AP-1 | 1 | 0 | 0 | 0 | 0 | 1 | | 20 |

Figure 21

HUMAN HOOKWORM VACCINE

CROSS-REFERENCE TO RELATED APPLICATIONS

This application claims benefit of and is a continuation of U.S. patent application Ser. No. 11/863,912 filed Sep. 28, 2007 now abandoned, the complete contents of which is hereby incorporated by reference. This application also claims benefit of U.S. patent application Ser. No. 10/825,692, filed Apr. 16, 2004, now issued U.S. Pat. No. 7,303,752 and to U.S. provisional patent application 60/862,916, filed Oct. 25, 2006, the complete contents of both of which are hereby incorporated by reference.

BACKGROUND OF THE INVENTION

1. Field of the Invention

The invention generally relates to a vaccine for human hookworm. In particular, the invention provides a human hookworm vaccine comprising an L3 larval stage antigen (e.g. Na-ASP-2 or Na-SAA-2) and at least one adult stage human hookworm antigen (e.g. Na-APR-1, Na-CP-2, Na-CP-3, Na-CP-4, Na-CP-5, or Na-GST-1) and two or more adjuvants, one of which is an aluminum-based adjuvant such as Alhydrogel®.

2. Background of the Invention

Hookworms are gastrointestinal nematodes that infect approximately 600 million people in developing countries (Hotez et al, 2006a). Adult hookworms bury their heads beneath the mucosa of the human intestine and feed on blood. Moderate to heavy infections result in iron deficiency anaemia, the major pathologic sequella of hookworm disease, as well as protein malnutrition. The resulting hookworm disease and anemia has a serious deleterious impact on many aspects of the health of infected individuals, including childhood growth retardation and cognitive development, and impaired fetal development during pregnancy (Hotez et al, 2004). The global disease burden resulting from chronic hookworm infection in childhood and pregnancy is enormous, possibly as high as 22 million disability-adjusted life years annually (Chan, 1997), making hookworm the second most important parasitic infection of humans after malaria (Hotez et al, 2005). In addition, the chronic immune suppression induced by hookworms and other helminths also has enormous impact on the ability of people to respond in a competent fashion to other infections (including malaria and HIV/AIDS and vaccines (Elliott et al, 2005; Su et al. 2005; Cooper et al., 2001; Cooper et al., 1999; Hotez et al, 2006b).

Unlike many other human helminthiases, clear-cut immunity against hookworms does not develop in the majority of infected individuals (Loukas et al., 2005). Indeed, the oldest people living in an endemic community sometimes have the heaviest worm burdens (Bethony et al., 2002). While anthelminthic drugs of the benzimidazole class are highly effective at eliminating existing hookworm infections, they do not protect against rapid re-infection (Hotez et al, 2006a). In areas of high transmission, hookworm re-infection will occur within 4-12 months (Albonico et al, 1995), leading to concerns about the long-term sustainability of such practices (Kremer 2004). In addition, newer data indicates that the efficacy of benzimidazole drugs decreases with frequent use (Albonico et al, 2003), leading to concerns about the possibility that anthelminthic drug resistance has developed (Albonico et al, 2004; Bethony et al, 2006). These observations have led to calls by the World Health Organization and other international agencies to develop new tools for the control of hookworm, including a hookworm vaccine (WHO, 2005). Therefore, an anthelminthic vaccine that induces immunological protection to minimize pathology and interrupt hookworm transmission is a highly desirable goal.

While regional economic growth (and with it, improvements in sanitation and clean water) in some parts of North America, Japan, South Korea, and China have translated into substantial reductions in endemic hookworm (Hotez et al, 2006a), estimated prevalence rates for the world's poorest and least developed regions remain high. For example, infection rates in sub-Saharan Africa (SSA) are equivalent to those first estimated more than 60 years ago (DeSilver et al., 2003), where an estimated 198 million cases occur (DeSilva et al, 2003). High hookworm infestation rates are principally in poverty-stricken rural areas where access to medical care is severely limited. Widespread use of a hookworm vaccine would lead to significant improvement in global health and in economic development (Hotez et al, 2006a; Hotez and Ferris, 2006). Therefore, an ideal vaccine hookworm vaccine would also be relatively easy and inexpensive to produce, and would be effective without the need for constant boosting.

The prior art has thus far failed to provide such a vaccine against human hookworm.

SUMMARY OF THE INVENTION

It is an object of this invention to provide a bivalent human hookworm vaccine. The vaccine is effective at inducing an immune response in individuals to whom it is administered, and administration results in a reduction in symptoms of hookworm disease.

The vaccine comprises: one or more L3 larval stage antigen (e.g. Na-ASP-2 and/or Na-SAA-2) and at least one adult stage human hookworm antigen (e.g. Na-APR-1, Na-CP-2, Na-CP-3, Na-CP-4, Na-CP-5, or Na-GST-1) and one or more adjuvants. In some embodiments, the vaccine composition includes two or more adjuvants, one of which is an aluminum-based adjuvant such as Alhydrogel®.

The present invention provides a hookworm vaccine comprising a hookworm larval stage antigen, a hookworm adult stage antigen, and one or more adjuvants. In one embodiment of the invention, the vaccine includes at least one larval-stage hookworm antigen, at least one adult-stage hookworm antigen, an aluminum-based adjuvant, and a second adjuvant. In one embodiment of the invention, the larval-stage hookworm antigen is Na-ASP-2 or Na-SAA-2, or both. Further, the larval-stage hookworm antigen may be antigenic fragments of Na-ASP-2 or Na-SAA-2, or both. In one embodiment of the invention, the adult-stage hookworm antigen is Na-APR-1, Na-GST, Na-CP-2, Na-CP-3, Na-CP-4, Na-CP-5, or antigenic fragments thereof, or a combination of several of these antigens. In one embodiment of the invention, the Na-APR-1 that is utilized is *Pichia* optimized Na-APR-1, or an antigenic fragment thereof. In some embodiments, the aluminum-based adjuvant is Alhydrogel® and the second adjuvant is CpG or Synthetic lipid A. In some embodiments of the invention, the aluminum-based adjuvant and the second adjuvant are combined together.

The invention also includes a method for vaccinating a patient in need thereof against hookworm infections. The method comprises the step of administering to the patient a hookworm vaccine comprising a hookworm larval stage antigen, a hookworm adult stage antigen, and one or more adjuvants. In one embodiment of the invention, the vaccine includes at least one larval-stage hookworm antigen, at least one adult-stage hookworm antigen, an aluminum-based adjuvant, and a second adjuvant. In one embodiment of the invention, the larval-stage hookworm antigen is Na-ASP-2 or Na-SAA-2, or both. Further, the larval-stage hookworm antigen may be antigenic fragments of Na-ASP-2 or Na-SAA-2, or both. In one embodiment of the invention, the adult-stage hookworm antigen is Na-APR-1, Na-GST, Na-CP-2, Na-CP-3, Na-CP-4, Na-CP-5, or antigenic fragments thereof, or a combination of several of these antigens. In one embodiment of the invention, the Na-APR-1 that is utilized is *Pichia* optimized Na-APR-1, or an antigenic fragment thereof. In some embodiments, the aluminum-based adjuvant is Alhydrogel® and the second adjuvant is CpG or Synthetic lipid A. In some embodiments of the invention, the aluminum-based adjuvant and the second adjuvant are combined together. In one embodiment, the method further comprises the step of administering a deworming agent to said patient.

BRIEF DESCRIPTION OF THE DRAWINGS

FIG. 1A and B. A, nucleotide sequence (SEQ ID NO: 1); and B, amino acid sequence (SEQ ID NO: 2) encoded by nucleotide sequence for Na-ASP-2.

FIG. 2A and B. A, cDNA nucleotide sequence (SEQ ID NO: 3, partial sequence 62-1351bp); and B, amino acid sequence (SEQ ID NO: 4) of Na-APR-1, Shanghai strain.

FIG. 3A and B. A, cDNA nucleotide sequence (SEQ ID NO: 5); and B, amino acid sequence (SEQ ID NO: 6) of Na-APR-1, Australian strain.

Figure 4:
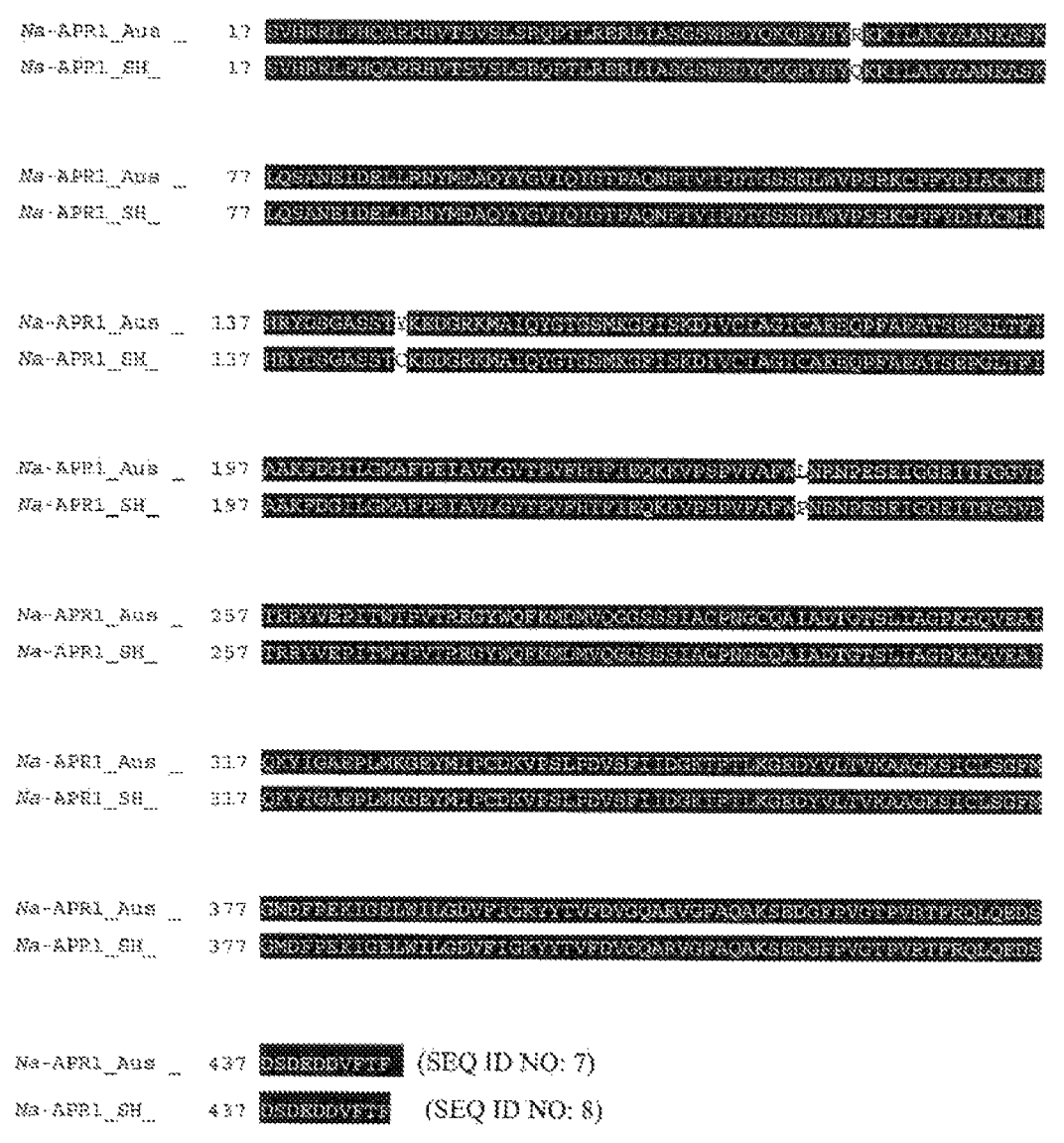

FIG. 4. Amino acid sequence (without signal sequence) alignment between Shanghai (SEQ ID NO: 7) and Australian (SEQ ID NO: 8) strains of Na-APR-1.

FIG. 5A and B. A, cDNA nucleotide sequence (SEQ ID NO: 9); and B, amino acid sequence (SEQ ID NO: 10) of *Pichia* optimized Na-APR-1 (Na-APR-1-O), based on Australian strain; the sequence is identical to residues 17-446 of Na-APR-1 Australian strain.

FIG. 6A and.B. A, cDNA nucleotide sequence (SEQ ID NO: 11); and B, amino acid sequence (SEQ ID NO: 12) encoded by nucleotide sequence for *Pichia* optimized Na-APR-1 (Australian strain) with Asp97 mutated to Ala97 (shown in bold and underlined).

FIG. 7A and B. A, cDNA nucleotide sequence (SEQ ID NO: 13); and B, amino acid sequence (SEQ ID NQ: 14) encoded by nucleotide sequence for *Pichia* optimized Na-APR-1 (Australian strain) with Asp284 mutated to Ala284.

FIG. 8A. and B. A, cDNA nucleotide sequence (SEQ ID NO: 15); and B, amino acid sequence (SEQ ID NO: 16) encoded by nucleotide sequence for *Pichia* optimized Na-APR-1 (Australian strain) with both Asp97 mutated to Ala97 and Asp284 mutated to Ala284.

FIG. 9A. and B. A, cDNA nucleotide sequence (SEQ ID NO: 17); and. B, amino acid sequence (SEQ ID NO: 18) encoded by nucleotide sequence for Na-GST-1.

FIG. 10A and B. A, cDNA nucleotide sequence (SEQ ID NO: 19); and B, amino acid sequence (SEQ ID NO: 20) encoded by nucleotide sequence for Na-GST-2.

FIG. 11A and B. A, cDNA nucleotide sequence (SEQ ID NO: 21); and B, amino acid sequence (SEQ ID NO: 22) encoded by nucleotide sequence for Na-GST-3.

FIG. 12A and B. A, cDNA nucleotide. sequence (SEQ ID NO: 23); and B, amino acid sequence (SEQ ID: NO 24) encoded by nucleotide sequence for Na-CP-2.

FIG. 13A and B. A, nucleotide sequence (SEQ ID NO: 25); and B, amino acid sequence (SEQ ID NO: 26) encoded by nucleotide sequence for Na-CP-3.

FIG. 14A and B. A, nucleotide sequence (SEQ ID NO: 27); and B, amino acid sequence (SEQ ID NO: 28) encoded by nucleotide sequence for Na-CP-4.

FIG. 15A and B. A, nucleotide sequence (SEQ ID NO: 29); and B, amino acid sequence (SEQ ID NO: 30) encoded by nucleotide sequence for Na-CP-5.

FIG. 16A and B. A, nucleotide sequence (SEQ ID NO: 31); and B, amino acid sequence (SEQ ID NO: 32) encoded by nucleotide sequence for Na-SAA-1.

FIG. 17A and B. A, nucleotide sequence (SEQ ID NO: 33); and B, amino acid sequence (SEQ ID NO: 34) encoded by nucleotide sequence for Na-SAA-2.

FIG. 18A and B. Individual titers of BALB/c mice given the indictaed doses of Na-ASP-2/Alhydrogel® (80 mcg Alhydrogel®) with and without 5 mcg ODN 2006 in 50 mcL i.m. at days 0 and 20, with terminal bleeds at day 30 (log scale). A, arithmetic mean; B, geometric mean.

FIG. 20. Ranking criteria for larval antigens for the human hookworm vaccine.

FIG. 21. Ranking criteria for adult antigens for the human hookworm vaccine.

DETAILED DESCRIPTION OF THE PREFERRED EMBODIMENTS OF THE INVENTION

Figure 19A:
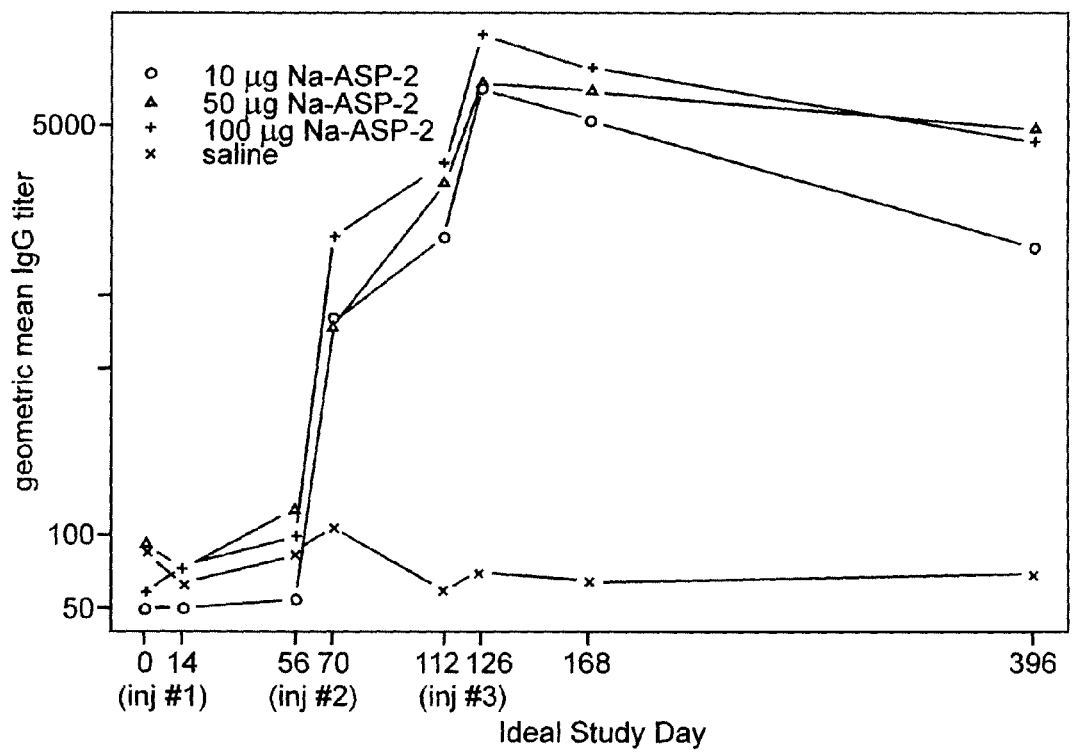
FIG. 19A and B. A, Anti-Na-ASP-2 Specific IgG antibody responses in humans immunized with Na-ASP-2, as determined by ELISA (undetectable titers were arbitrarily assigned a titer of 50); B, proliferative response of peripheral blood mononuclear cells from humans immunized with Na-ASP-2, after in vitro stimulation with Na-ASP-2.
Figure 19B:
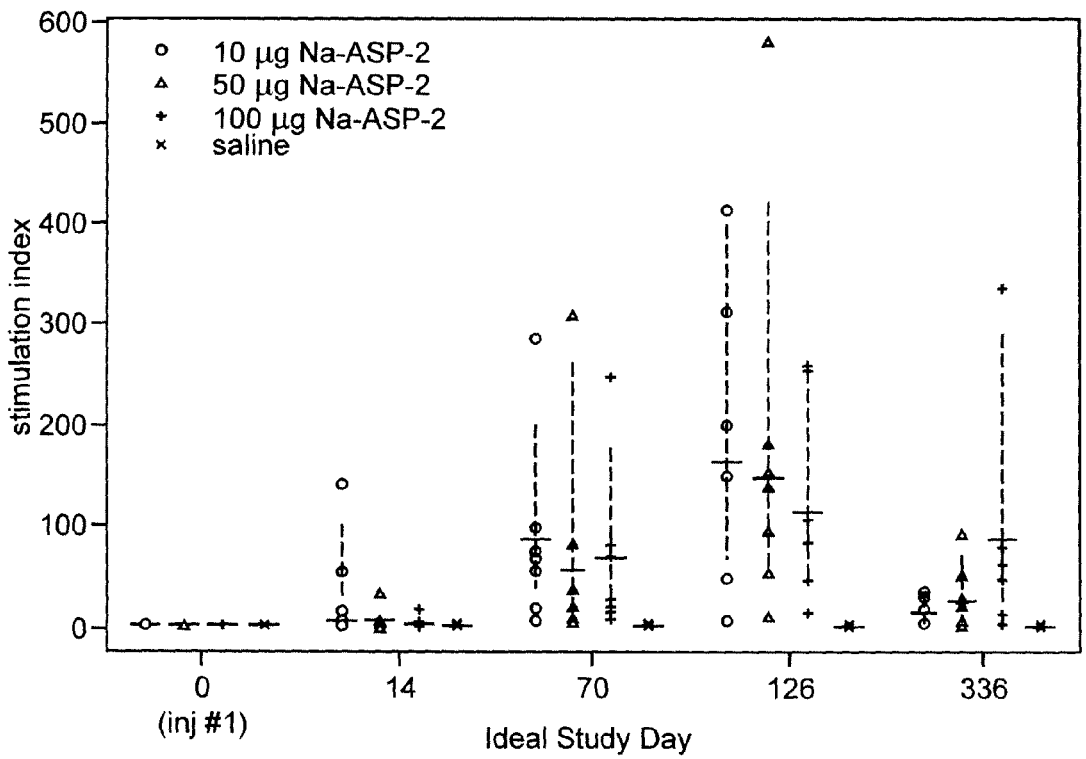

It is an object of this invention to provide a bivalent human hookworm vaccine. The vaccine is effective at inducing an immune response in individuals to whom it is administered, and administration results in a reduction in symptoms of hookworm disease, e.g. worm burden, blood loss, etc.

The vaccine comprises: one or more L3 larval stage antigen and at least one adult stage human hookworm antigen [e.g. Na-APR-1 (exemplary sequences for which include SEQ ID NO: 4, SEQ ID NO: 6, SEQ ID NO: 12, SEQ ID NO: 14, and SEQ ID NO: 16), Na-CP-2 (SEQ ID NO: 24), Na-CP-3 (SEQ ID NO: 26), Na-CP-4 (SEQ ID NO: 28), Na -CP-5 (SEQ ID NO: 30), or Na-GST-1 (SEQ ID NO: 18)] and one or more adjuvants. In some embodiments, the vaccine composition includes two or more adjuvants, one of which may be an aluminum-based adjuvant such as Alhydrogel®.

In a preferred embodiment of the invention, the antigens are *Necator americanus* antigens.

With respect to the one or more larval stage antigens that are used in the vaccine, exemplary antigens are Na-ASP-2 SEQ ID NO: 2), Na-SAA-1 (SEQ ID NO: 32), and Na-SAA-2 (SEQ ID NO: 34), the sequences of which are found in FIGS. 1, 16 and 17, respectively.

With respect to the one or more adult stage antigens that may be used in the vaccine composition, the following exemplary sequences are contemplated: Na-APR-1 Shanghai strain (SEQ ID NO: 4, partial sequence 62-1351bp) as depicted in FIG. 2; Na-APR-1 Australia strain (SEQ ID NO: 6) as depicted in FIG. 3; Na-APR-1 amino acid sequence (without signal) alignment between Shanghai (SEQ ID NO: 7) and Australia (SEQ ID NO: 8) strains as depicted in FIG. 4; *Pichia* Optimized Na-APR-1 (Na-APR-1-O, (SEQ ID NO: 10)) Sequence (based on. Australia strain) as depicted in FIG. 5; *Pichia* Optimized Na-APR-1 (Na-APR-1-O) with Asp97 mutated to Ala97 (SEQ ID NO: 12) as depicted in FIG. 6; *Pichia* Optimized Na-APR-1 (Na-APR-1-O) with Asp284 mutated to Ala284 (SEQ ID NO: 14) as depicted in FIG. 7; *Pichia* Optimized Na-APR-1 (Na-APR-1-O) with both Asp97 /Asp284 mutated to Asp97/Ala284 (SEQ ID NO: 16) as depicted in FIG. 8; Na-GST-1 as depicted in FIG. 9; Na- GST-2 (SEQ ID NO: 20) as depicted in FIG. 10; Na-GST-3 (SEQ ID NO: 22) as depicted in FIG. 11; Na-CP-2 (SEQ ID NO: 24) as depicted in FIG. 12; Na-CP-3 (SEQ ID NO: 26) as depicted in FIG. 13; Na-CP-4 (SEQ ID NO: 28) as depicted in FIG. 14; and. Na-CP-5 (SEQ ID NO: 30) as depicted in FIG. 15.

"Larval stage antigen" or "L3 larval stage antigen" refers to antigens that are expressed during the L3 larval stage of the hookworm life cycle. In some cases, such antigens may also be expressed during other stages of the life cycle, i.e. the antigen may not be expressed exclusively in the larval stage. However, a "larval stage antigen" is expressed at least in the L3 larval stage.

In preferred embodiments, *Pichia* optimized Na-APR-1 sequences are used, as described in numbers 4-7 above. Codon optimization enhances the efficiency of DNA expression vectors used in DNA vaccination by increasing protein expression. The codon frequency of the foreign (i.e. hookworm) DNA embedded into the yeast expression vector may not be optimal for adequate protein expression in the host resulting in low level protein expression. A potential solution for the codon bias is to optimize the codon sequences of a gene to suit the requirements of the host without altering the original amino acid sequence of the protein See, for example, Jareborg N, Durbin R, 'Alfresco—a workbench for comparative genomic sequence analysis', Genome Res 2000 August; 10(8):1148-57, 16; and Kim C H, Oh Y, Lee T H: Codon optimization for high level expression of human erythropoietin (EPO) in mammalian cells. Gene 199:293-301 (1997).

With respect to the adult stage GST antigen, three exemplary Na-GST amino acid sequences, Na-GST-1, Na-GST-2, and Na-GST-3, are represented in FIGS. 9B, 10B and 11B, respectively, and nucleotide sequences that encode these antigens are represented in FIGS. 9A, 10A and 10B, respectively.

With respect to the adult stage Na-CP antigens that are used in the vaccine, exemplary amino acid sequences of this antigen are represented in FIGS. 12B (Na-CP-2), 13B (Na-CP-3), 14B (Na-CP-4), and 15B (Na-CP-5) and exemplary nucleotide sequences that encode these antigens are represented in FIGS. 12A, 13A, 14A and 15A, respectively.

With respect to the larval stage SAA antigens, exemplary nucleic acid sequences and encoded amino acid sequences of Na-SAA-1 and Na-SAA-2 are given in FIGS. 17 and 18, respectively.

Examples of antigens, their amino acid primary sequences, and nucleic acid sequences which encode them are given herein, and any combination of the antigens depicted herein may be used in the practice of the invention. However, those of skill in the art will recognize that many variants of the sequences presented herein may exist or be constructed which would also function as antigens in the practice of the present invention. For example, with respect to amino acid sequences, variants may exist or be constructed which display: conservative amino acid substitutions; non-conservative amino acid substitutions; truncation by, for example, deletion of amino acids at the amino or carboxy terminus, or internally within the molecule; or by addition of amino acids at the amino or carboxy terminus, or internally within the molecule (e.g. the addition of a histidine tag for purposes of facilitating protein isolation, the substitution of residues to alter solubility properties, the replacement of residues which comprise protease cleavage sites to eliminate cleavage and increase stability, the addition or elimination of glycosylation sites, and the like, or for any other reason). Such variants may be naturally occurring (e.g. as a result of natural variations between species or between individuals); or they may be purposefully introduced (e.g. in a laboratory setting using genetic engineering techniques). All such variants of the sequences disclosed herein are intended to be encompassed by the teaching of the present invention, provided the variant antigen displays sufficient identity to the described sequences. Preferably, identity will be in the range of about 50 to 100%, or in the range of about 75 to 100%, or in the range of about 80 to 100%, or 85% to 100%, or 90% to 100%, or about 95% to 100% of the disclosed sequences. The identity is with reference to the portion of the amino acid sequence that corresponds to the original antigen sequence, i.e. not including additional elements that might be added, such as those described below for chimeric antigens.

The invention also encompasses chimeric antigens, for example, antigens comprised of the presently described amino acid sequences plus additional sequences which were not necessarily associated with the disclosed sequences when isolated but the addition of which conveys some additional benefit. For example, such benefit may be utility in isolation and purification of the protein, (e.g. histidine tag, GST, and maltose binding protein); in directing the protein to a particular intracellular location (e.g. yeast secretory protein); in increasing the antigenicity of the protein (e.g. KHL, haptens). All such chimeric constructs are intended to be encompassed by the present invention, provided the portion of the construct that is based on the sequences disclosed herein is present in at least the indicated level of homology.

Those of skill in the art will recognize that it may not be necessary to utilize the entire primary sequence of a protein or polypeptide in order to elicit an adequate antigenic response to the parasite from which the antigen originates. In some cases, a fragment of the protein is adequate to confer immunization. Thus, the present invention also encompasses antigenic fragments of the sequences disclosed herein, and their use in vaccine preparations. In general, such a fragment will be at least about 10-13 amino acids in length. Those of skill in the art will recognize that suitable sequences are often hydrophilic in nature, and are frequently surface accessible.

Likewise, with respect to the nucleic acid sequences disclosed herein, those of skill in the art will recognize that many variants of the sequences may exist or be constructed which would still function to provide the encoded antigens or desired portions thereof. For example, due to the redundancy of the genetic code, more than one codon may be used to code for an amino acid. Further, as described above, changes in the primary sequence of the antigen may be desired, and this would necessitate changes in the encoding nucleic acid sequences. In addition, those of skill in the art will recognize that many variations of the nucleic acid sequences may be constructed for purposes related to cloning strategy, (e.g. for ease of manipulation of a sequence for insertion into a vector, such as the introduction of restriction enzyme cleavage sites, etc.), for purposes of modifying transcription (e.g. the introduction of promoter or enhancer sequences, and the like), or for any other suitable purpose. All such variants of the nucleic acid sequences disclosed herein are intended to be encompassed by the present invention, provided the sequences display about 50 to 100% identity to the original sequence and preferably, about 75 to 100% identity, and most preferably about 80 to 100% identity. The identity is with reference to the portion of the nucleic acid sequence that corresponds to the original sequence, and is not intended to cover additional elements such as promoters, vector-derived sequences, restriction enzyme cleavage sites, etc. derived from other sources.

In a preferred embodiment, the vaccine of the present invention includes an aluminum-based adjuvant such as the aluminum hydroxide adjuvant Alhydrogel® (available from Superfos and Brenntag Biosector) or the aluminum-containing adjuvant AS04 (available from GlaxoSmithKline). In addition, at least one additional adjuvant is also a component of the vaccine. Exemplary additional or second adjuvants include but are not limited to the following:

1) AS03, a proprietary formulation manufactured by Glaxo Smith Kline that contains an oil-in-water emulsion;
2) AS02A, a proprietary formulation manufactured by Glaxo Smith Kline that contains the same oil-in-water emulsion as in ASO3, plus two immunostimulants "3D-MPL" and "QS-21".

AS03 and AS02A are described (under their original designations SBAS3 and SBAS2, respectively) is Stoute et al NEJM 1997 336:86-91. It is noted that, AS02A and AS03 are designed to be used with the aluminum based adjuvant AS04, also available from GlaxoSmithKline.

3) A synthetic oligodeoxynucleotide adjuvant containing cytosine-guanine dinucleotides in particular base contexts or CpG motifs, (CpG ODN). This adjuvant is an immunomodulatory molecule and is available from Coley.
4) Various lipid A derivatives. Lipid A is the portion of lipopolysaccharide that is known to be the primary component with regard to adjuvanticity and toxicity. Derivatives of lipid A have been produced in an attempt to retain the immunostimulatory activity of Lipid A yet reduce the toxicity. One such derivative, monophosphoryl lipid A (MPL, available from Chiron), has been shown to exhibit strong Th1 adjuvant activity but with a considerably reduced toxicity compared to LPS. MPL has adjuvant activity whether used alone, or in combination with other immunostimulants, such as CpG ODN, or aluminum hydroxide. Another synthetic lipid A derivative that is very similar to the lipopolysaccharide derivative lipid A monophosphoryl (MPL) by Chiron is available from the Infectious Disease Research Institute, Seattle, Wash.
5) A publication by McCluskie and Weeratna (Infectious Disorders, 2001, 1, 263-271) gives examples of several different adjuvant systems, each of which may be employed in the practice of the present invention.

Examples of other suitable adjuvants include but are not limited to Seppic, Quil A, etc. Preferred adjuvants combinations are: Alhydrogel®+CpG 10103 and Alhydrogel®+synthetic lipid A.

The present invention provides compositions for use in eliciting an immune response against hookworm. The compositions may be utilized as a vaccine against hookworm. By "eliciting an immune response" we mean that an antigen stimulates synthesis of specific antibodies at a titer of about >1 to about 1×10$^6$ or greater. Preferably, the titer is from about 10,000 to about 1×10$^6$ or more, as measured by enzyme Linked Immunosorbent Assay (ELISA) or greater than 1,000 antibody units as defined previously (Malkin et al., 2005a; 2005b). By "vaccine" we mean an antigen or antigen preparation that elicits an immune response that results in a decrease in hookworm burden of a least about 30% in an organism in relation to a non-vaccinated (e.g. adjuvant alone) control organism. This work burden reduction has been calculated to restore a child's daily iron requirements that would otherwise be lost from a moderate (i.e. infections with between 2,000 and 4,000 hookworm eggs per gram of feces) infection with hookworm Preferably, however, the level of the decrease in hookworm burden would approach 50%, or more.

The present invention provides compositions for use in eliciting an immune response which may be utilized as a vaccine against hookworm. The compositions include a substantially purified recombinant hookworm antigen or variant thereof as described herein, and a pharmacologically suitable carrier. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of hookworm antigen in the formulations may vary. However, in general, the amount in the formulations will be from about 1-99%.

The present invention also provides methods of eliciting an immune response to hookworm and methods of vaccinating a mammal against hookworm. The methods generally involve identifying a suitable vaccine recipient, and administering a composition comprising the hookworm antigens and adjuvants described herein in a pharmacologically acceptable carrier to the recipient. The vaccine preparations of the present invention may be administered by any of the many suitable means which are well known to those of skill in the art, including but not limited to by injection, orally, intranasally, by ingestion of a food product containing the antigens, etc. In preferred embodiments, the mode of administration is subcutaneous or intramuscular. Patients with an existing worm burden may be treated with a de-worming agent such as benzimazole, and then be provided with the vaccine.

The present invention provides methods to elicit an immune response to hook worm and to vaccinate against hookworm in mammals. In one embodiment, the mammal is a human.

Those of skill in the art will recognize that, in general, in order to vaccinate (or elicit an immune response in) a species of interest (e.g. humans) against hookworm, the antigen which is utilized will be derived from a species of hookworm which parasitizes the species of interest. For example, in general, antigens from *Necator americanus* may be preferred for the immunization of humans, and antigens from *Ancylostoma canium* may be preferred for the immunization of dogs. However, this may not always be the case. For example, *Ancylostoma canium* is known to parasitize humans as well as its primary canine host. Further, cross-species hookworm antigens may sometimes be highly effective in eliciting an immune response in a non-host animal, i.e. in an animal that does not typically serve as host for the parasite from which the antigen is derived. Rather, the measure of an antigen's suitability for use in an immune-stimulating or vaccine preparation is dependent on its ability to confer protection against invasion and parasitization by the parasite as evidenced by, for example, hookworm burden reduction or inhibition of hookworm associated blood loss (e.g. as measured by hematocrit and/or hemoglobin concentration. For example, for use in a vaccine preparation, an antigen upon administration results in a reduction in worm burden of at least about 30%, preferably at least about 50%, and most preferably about 60 to about 70%.

EXAMPLES

Example 1

Scoring System for Determining an Efficacious Human Hookworm Vaccine

A scoring system that incorporates essential criteria for determining an efficacious human hookworm vaccine has been developed (Table 1). The criteria include endpoints that focus on pathology (blood loss, worm burdens), transmission (faecal egg counts), ease of process development (known function/structure of protein) and immunoepidemiology (associations between immune responses and infection intensities in naturally exposed/infected cohorts). Once produced in soluble form, recombinant versions of the major L3 ES products were tested for vaccine efficacy in the canine and hamster models of infection.

TABLE 1

Ranking of candidate hookworm antigens based on seven major criteria, and grading of each criterion to allow a final score of vaccine efficacy to be tallied.

| | Antigen | | | | | | | |
|---|---|---|---|---|---|---|---|---|
| | 1<br>Adult worm reduction (dog) | 2<br>Adult worm reduction (hamster)$^\S$ | 3<br>Reduced host blood loss | 4<br>EPG* reduction | 5<br>Known function/ structure | 6<br>Human immuno-epidemiology | 7<br>Protective homologs | 8<br>Final Score |
| Grading | 0-5 | 0-5 | 0-4 | 0-4 | 0-2 | 0-3 | 0-2 | |
| ASP-2 | 2 | 3 | 1 | 3 | 2 | 3 | 2 | 16/25 (64%) |
| APR-1 | 2 | 3 | 3 | 3 | 2 | ND$^\dagger$ | 1 | 14/22 (64%) |
| CP-2 | 1 | 2 | 0 | 3 | 2 | ND | 1 | 9/22 (41%) |
| GST-1 | 2 | 3 | 0 | 1 | 2 | ND | 1 | 9/22 (41%) |

1 Reflects quintiles of reduction in worm burdens in dogs compared to controls
2 Reflects quintiles of reduction in worm burdens in hamsters compared to controls
3 Each grade reflects an increase of 0.5 g · dL − 1 hemoglobin above control group
4 Reflects tertiles of epg reduction compared to controls
5 Function or structure known in hookworm (grade of 2) or in a related helminth (grade of 1) - enables biochemical assay development
6 Association between antibody response and reduced epg in people (number = strength of association)
7 Protective homologs in other nematodes (grade of 2) or infectious agents (grade of 1)
8 Tally of scores from each category;
ND—deduct from final score
*EPG—eggs per gram of feces;
$^\S$B. Zhan, S. Xiao, J. Bethony, A. Loukas, P. Hotez, unpublished data using *N. americanus* in the hamster model;
$^\dagger$ND—Not Determined.

Based on this ranking system, recombinant antigens ASP-2, Ac-APR-1, GST and CP-2 were selected as a lead vaccine candidates for further process development, cGMP manufacture and clinical testing.

Evidence that ASP-2 is a protective antigen in dogs (Ac-ASP-2) and hamsters (Ay-ASP-2) was published by the inventors in Bethony et al (2005) and Gould et al (2004); Mendez et al (2005), respectively. Human immunoepidemiological evidence pointing to the protective effect of ASP-2 antibodies was published in Bethony et al (2005). Evidence that Na-ASP-2 is protective in hamsters is unpublished, while evidence that anti-Na-ASP-2 antibodies inhibit hookworm larval penetration in vitro was published by Goud et al (2005). Evidence that APR-1 is a protective antigen in dogs (Ac-APR-1) was published by the inventors in Loukas et al (2005). Evidence that Na-APR-1 is protective is also available, but unpublished. Evidence that GST is a protective antigen in dogs (Ac-GST-1) was published by the inventors in Zhan et al (2005). Evidence that CP-2 is a protective antigen (Ac-CP-2) was published by the inventors in Loukas et al (2004).

Example 2

Human Clinical Trial with Recombinant Na-ASP-2

A double-blind, placebo-controlled, randomized dose-escalation Phase 1 study was carried out to evaluate the safety, tolerability, and immunogenicity of three intramuscular administrations of the Na-ASP-2 hookworm vaccine in healthy adult volunteers. Thirty-six subjects between the ages of 18 and 45 were randomized to receive a 0.5 mL injection of either vaccine or saline placebo intramuscularly on study days 1, 56 (week 8), and 112 (week 16). Enrolled subjects were divided into three dose cohorts of twelve subjects each.

Within each dose cohort, three subjects were randomized to receive saline placebo and nine subjects were randomized to receive one of three doses of the Na-ASP-2 hookworm vaccine. Those randomized to receive vaccine were given 10, 50, or 100 μg of Na-ASP-2 in the first, second and third dose cohorts, respectively. Higher dose concentrations or additional (second or third) injections were not administered until the effects of the preceding dose concentration and injection had been evaluated. Subjects were evaluated for adverse events, vital signs, blood chemistries, hematology, and urinalysis.

The cumulative safety data from this trial has demonstrated that the vaccine is both safe and immunogenic in healthy, hookworm-uninfected adults, with mild to moderate injection-site tenderness, erythema, swelling and pruritus being the most commonly observed vaccine-related adverse events. Induration and warmth at the injection site occurred less frequently. All injection site reactions were considered mild or moderate in severity and were typical of those observed with aluminum-adjuvanted vaccines administered intramuscularly. The frequency of injection site reactions was not dose-dependent, and did not increase with successive vaccinations. Unusual injection site reactions were observed in one male participant in the 10 μg dose group and in three female subjects in the 50 μg dose group after the second injection. These reactions were delayed erythematous reactions ranging in size from 5 to 12 cm in diameter that started approximately 10 days after the injection and lasted for 1 to 4 days, resolving without incident. Several vaccinated individuals also experienced mild to moderate systemic adverse events including fever, headache and nausea. No vaccine-related serious adverse events occurred during the study, and no clinically-significant alternations in clinical laboratory parameters were observed.

The Na-ASP-2 hookworm vaccine induced a significant antigen-specific IgG antibody response in a dose-dependent manner (FIG. 10): there was a statistically significant difference between the placebo and vaccine groups starting as early as 14 days after the second injection which remained through the 8 month follow-up time point after the third injection. Isotyping revealed that the induced antibody response consisted primarily of IgG1, with a small component due to IgG4. No appreciable antigen-specific IgM, IgA or IgE responses were detected. Finally, significant antigen-specific cellular immune responses were also observed, with increasing responses seen after successive injections of vaccine (FIG. 11).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

Example 3

Comparative Immunogenicity of Na-ASP-2/Alhydrogel® with and without ODN 2006 in BALB/c Mice For each adjuvant tested, compatibility and stability studies were undertaken to ensure that all individual components (antigen, adjuvant 1, adjuvant 2, etc.) were compatible and that adequate stability was achieved upon formulation. For Alhydrogel® based vaccine formulations to which other adjuvants were added, this involved assays that test antigen binding, conformation, and integrity over various periods of time and at different temperatures.

With reference to FIGS. 13 A and B, Groups of 10 female BALB/c mice were given the indicated doses of Na-ASP-2/Alhydrogel® with or without 5 micrograms ODN 2006, as indicated. Total antigen-specific IgG was measured in the sera of each animal by indirect ELISA.

FIGS. 14 A and B show the geometric and arithmetic means, respectively, of the results. As can be seen, a comparative immunogenicity study of Na-ASP-2/Alhydrogel® with and without ODN 2006 in BALB/c mice was performed. The results showed the ODN2006 boosts the immune response in BALB/c mice over that achieved with Na-ASP-2/Alhydrogel® alone, as determined by indirect ELISA that measure total antigen specific IgG (antibody).

References for Background and Examples 1-3

Albonico M, Smith P G, Ercole E, Hall A, Chwaya H M, Alawi K S, Savioli L. 1995. Rate of reinfection with intestinal nematodes after treatment of children with mebendazole or albendazole in a highly endemic area. Trans R Soc Trop Med. Hyg. 89:538-41.

Albonico M, Bickle Q, Ramsan M, Montresor A, Savioli L, Taylor M. 2003. Efficacy of mebendazole and levamisole alone or in combination against intestinal nematode infections after repeated targeted mebendazole treatment in Zanzibar. Bull World Health Organ. 81:343-52.

Albonico M, Engels D, Savioli L. 2004. Monitoring drug efficacy and early detection of drug resistance in human soil-transmitted nematodes: a pressing public health agenda for helminth control. Int J. Parasitol. 34:1205-10.

Bethony J M, Loukas A, Smout M J, Mendez S, Wang Y, Bottazzi M E, Zhan B, Williamson A L, Lustigman S, Correa-Oliveira R, Xiao S H, Hotez P J. 2005. Antibodies against a secreted protein from hookworm larvae reduce the intensity of infection in humans and vaccinated laboratory animals. FASEB Journal 19: 1743-5.

Bethony J, Chen J, Lin S, et al. Emerging patterns of hookworm infection: influence of aging on the intensity of *Necator* infection in Hainan Province, People's Republic of China. Clin Infect Dis 2002; 35: 1336-44.

Bethony J, Brooker S, Albonico M, Geiger S, Loukas A, Diemert D, Hotez P J. 2006. Soil-transmitted helminth infections: *ascariasis*, trichuriasis, and hookworm. Lancet 367: 1521-32

Chan M S. 1997. The global burden of intestinal nematode infections—fifty years on. Parasitol Today 13:438-43.

Cooper P J, Chico M, Sandoval C, et al. Human infection with *Ascaris lumbricoides* is associated with suppression of the interleukin-2 response to recombinant cholera toxin B subunit following vaccination with the live oral cholera vaccine CVD 103-HgR. Infect Immun 2001; 69: 1574-80.

Cooper P J, Espinel I, Wieseman M, et al. Human onchocerciasis and tetanus vaccination: impact on the postvaccination antitetanus antibody response. Infect Immun 1999; 67: 5951-7.

DeSilva N, Brooker S, Hotez P, Montresor A, Engels D, Savioli L. 2003. Soil-transmitted helminth infections: updating the global picture. Trends in Parasitology 12: 547-51

Elliott A M, Namujju P B, Mawa P A, et al. A randomised controlled trial of the effects of albendazole in pregnancy on maternal responses to mycobacterial antigens and infant responses to bacille Calmette-Guerin (BCG) immunisation [ISRCTN32849447]. BMC Infect Dis 2005; 5: 115.

Goud G N, Zhan B, Ghosh K, Loukas A, Hawdon J, Dobardzic A, Deumic V, Liu S, Dobardzic R, Zook R C, Qun J, Liu Y Y, Hoffman L, Chung-Debose D, Patel R, Mendez S, Hotez P J. 2004. Cloning, yeast expression, isolation and vaccine testing of recombinant *Ancylostoma* secreted protein 1 (ASP-1) and ASP-2 from *Ancylostoma ceylanicum*. Journal of Infectious Diseases 189: 919-29.

Goud G N, Bottazzi M E, Zhan B, Mendez S, Deumic V, Pleiskatt J, Liu S, Wang Y, Bueno L, Fujiwara R, Samuel A, Ahn S Y, Solanki M, Asojo O, Wen J, Saul A, Bethony J M, Loukas A, Roy M, Hotez P J. 2005. Expression of the *Necator americanus* hookworm larval antigen Na-ASP-2 in *Pichia pastoris* and purification of the recombinant protein for use in human clinical trials. Vaccine 2005; 4754-64.

Hotez P J, Ferris M T. The antipoverty vaccines. Vaccine 2006; 24: 5787-99.

Hotez, P, Brooker S, Bethony J, Bottazzi M, Loukas A, Xiao S. 2004. Hookworm Infection. New England Journal of Medicine 351: 799-807.

Hotez P J, Bethony J, Bottazzi M E, Brooker S, Buss P. 2005. Hookworm—"the great infection of mankind." PLOS Medicine 2: e67 177-81.

Hotez P J, Bethony J, Bottazzi M E, Brooker S, Diemert D, Loukas A. 2006a. New technologies for the control of human hookworm infection. Trends in Parasitology 22: 327-31.

Hotez P J, Molyneux D H, Fenwick A, Ottesen E, Ehrlich Sachs S, Sachs J D. 2006b. Incorporating a rapid impact package for neglected tropical diseases with programs for HIV/AIDS, tuberculosis, and malaria. PLoS Medicine 3: e102.

Kremer M, Miguel E. The illusion of sustainability. Center for Global Development working paper, 2004.

Loukas A, Bethony J M, Williamson A L, Goud G N, Mendez S, Zhan B, Hawdon J M, Bottazzi M E, Brindley P J, Hotez P J. 2004. Vaccination of dogs with recombinant cysteine protease from the intestine of canine hookworms diminishes fecundity and growth of worms. Journal of Infectious Diseases 189: 1952-61.

Loukas A, Bethony J M, Mendez S, Fujiwara R T, Goud G N, Ranjit N, Zhan B, Jones B, Bottazzi M E, Hotez P J. 2005. Vaccination with recombinant aspartic hemoglobinase reduces parasite load and blood loss after hookworm infection. PLoS Medicine 2: e295.

Loukas A, Constant S L, Bethony J M. Immunobiology of hookworm infection. FEMS Immunol Med Microbiol 2005; 43: 115-24.

Malkin E M, Diemert D J, McArthur J H, Perreault J R, Miles A R, Giersing B K, Mullen G F, Orcutt A, Muratova O, Awkal M, Zhou H, Wang J, Stowers A, Long C A, Mahanty S, Miller L H, Saul A, Durbin A H. 2005a. Infect. Immun. 73: 3677-85.

Malkin E M, Durbin A P, Diemert D J, Sattabongkot J, Wu Y, Miura K, Long C A, Lambert L, Miles A P, Wang J, Stowers A, Miller L H, Saul A. 2005b. Phase I vaccine trial of Pvs 25H: a transmission blocking vaccine for *Plasmodium vivax* malaria. Vaccine 23: 3131-8.

Mendez S, Zhan B, Goud G, Ghosh K, Dobardzic A, Wu W H, Liu S, Deumic V, Dobardzic R, Liu Y Y, Bethony J, Hotez P J. 2005. Effect of combining the larval antigens *Ancylostoma* secreted protein 2 (ASP-2) and metalloprotease 1 (MTP-1) in protecting hamsters against hookworm infection and disease caused by *Ancylostoma ceylanicum*. Vaccine 23: 3123-30.

Su Z, Segura M, Morgan K, Loredo-Osti J C, Stevenson M M. Impairment of protective immunity to blood-stage malaria by concurrent nematode infection. Infect Immun 2005; 73: 3531-9.

World Health Organization. 2005. Deworming for Health and Development, Report of the third global meeting of the partners for parasite control, Geneva 29-30, November 2004.

Zhan B, Liu S, Perally S, Fujiwara R, Brophy P, Liu Y Y, Feng J J, Williamson A, Wang Y, Bueno L L, Mendez S, Goud G, Bethony J M, Hawdon J M, Loukas A, Jones K, Hotez P J. 2005. Biochemical characterization and vaccine potential of a heme binding glutathione S transferase (GST) from the adult hookworm *Ancylostoma caninum* Infection and Immunity 73: 6903-11.

Example 4

Hookworm Vaccine Antigens Screening with *Necator americanus*-hamster Model

1. Introduction

Among the three major soil-transmitted nematodes, *Ascaris lumbricoides*, *Ancylostoma duodenale/Necator americanus* (hookworms), and *Trichuris trichuria*, hookworms are the most pathogenic because of their blood feeding behavior that directly causes blood loss and iron deficiency anemia (de Silva et al, 2003; Bethony et al, 2006). More seriously for children and women who have low iron stores, hookworm infection can cause retardation of physical and intellectual development (Bundy et al 1995; Brooker et al, 1999; Hotez et al, 2006. 2004a).

More than 700 million people living in the developing countries of tropical and subtropical regions are estimated to be infected with hookworms. Hookworm infection causes more DALYs lost (1.8 million) than any other helminthiases with the exception of lymphatic filariasis (Hotez et al, 2006. 2004a, Bethony et al, 2006). Mass chemotherapy remains a mainstay of hookworm control strategies (WHO 2002; Allen et al, 2002; Hotez et al, 2002). Indeed, repeated chemotherapy at regular intervals in high-risk groups is useful to keep a low morbidity, and will frequently result in immediate improvement in child health and development (Bhargava et al, 2003; Stephenson et al, 1989) although continued used of anthelmintics is perhaps contributing to the development of anthelminthic resistance (Albonico et al, 2004). Unfortunately, the treated people, particularly, in highly endemic areas, soon become reinfected as early as 4-12 months after drug treatment. Therefore, preventive vaccine against hookworm infection becomes an attractive alternative for hookworm control.

The major obstacle for developing human hookworm vaccine is the absence of a suitable laboratory animal host to complete human hookworm's life cycle (Hotez et al, 2003a, b, 2004b). Several laboratories have tried to infect *N. americanus* in mice, dogs, guinea pigs, rabbits and hamsters (Timothy and Behnke, 1993, 1997; Nagahana et al, 1962; Yoshida et al, 1960; Yoshida and Fukutome 1967; Sen, 1970; Sen and Seth, 1970; Sen and Deb, 1973). However, the efforts were not successful either due to inconsistent maintenance of the organism within the laboratory animals, the requirement for cortisone-immuno-supression, or use of infant animals. However, great progress was made by Xue and her colleagues (Xue et al, 2003a, b) in the Institute of Parasitic Diseases (IPD), Chinese Center of Disease Control and Prevention (CCDCP) who successfully adapted *N. americanus* to the Chinese golden hamster *Mosocricetus auratus* without the requirement for exogenous steroids or other immunosuppression, or the requirement to infect infant hamsters. Infection with the human hookworm *N. americanus*, originally obtained from an infected patient living in Human Province, China, has been established in the golden hamster *Mosocricetus auratus* for more than 100 generations over a period of 26 years with no need of steroids (Xue et al, 2003). This model has been successfully used for testing anthelminthic drugs (Xue et al, 2005).

Several hookworm vaccine antigens have been tested with an *Ancylostoma caninum*-dog model or *Ancylostoma ceylanicum*-hamster model and some of them exhibited certain degrees of protection against *A. caninum* L3 challenge with reduction of either adult worm burden or blood loss (Hotez, et al, 2003a; Goud et al, 2004; Mendez et al, 2005; Loukas et al, 2005, Bethony et al, 2005, Fujiwara (in press)). Among the vaccines tested, Na-ASP-2 is a leading antigen (Bethony et al, 2005; Goud et al, 2005). However, these animal models are used to test vaccine antigens from animal hookworms such as *A. caninum* or *A. ceylanicum*. The effect of such vaccines can be used to deduce or mimic the effect of human hookworm homologues, but can not reflect completely the real pattern of human hookworm. The *Necator americanus*-hamster model currently is the only animal model for maintaining the species of human hookworms. This human hookworm model was thus used to test various hookworm vaccine candidates. The results showed that some of the antigens conferred protective against symptoms of hookworm infection.

2. Materials and Methods 2.1 Hamsters

Male Chinese golden hamsters *Mesocricetus auratus* with an age of 7-8 weeks were supplied by either Shanghai Institute of Biological Products of the Chinese Ministry of Health or Shanghai Animal Center, Chinese Academy of Sciences (SCXK (Hu) 2003-0003). The hamsters were housed in groups of 10 in plastic cages. All animals had free access to water and commercial rodent food purchased from Shanghai Shiling Biological and Scientific Technique Corporation.

2.2 Vaccine Antigen and Adjuvant

Ten recombinant hookworm proteins derived either from *N. americanus* or *A. caninum* were used to test vaccine effect with the *N. americanus*-hamster model performed in the IPD. CCDCP. Na-ASP-2, a major *Ancylostoma*-secreted protein-2 secreted by stimulated infective larvae of *N. americanus*, is a leading hookworm vaccine antigen. The recombinant Na-ASP-2 either with his-tag at C-terminal or without tag were expressed in the *Pichia pastoris* X-33 and purified with chromatography (Goud et al, 2005, Hawdon et al, 1999, Mendez et al, 2005). Na-ASP-1 is another *Ancylostoma*-secreted protein secreted by stimulated infective larvae of *N. americanus* (Hawdon et al, 1996, Goud et al, 2004). Ac-GST-1, a novel glutathione S-transferase produced by *A. caninum* adult worms, is a heme binding protein that is believed to be involved in the detoxification of heme derived from blood feeding (Zhan et al, 2005). Ac-CP-2 is a cathepsin-B cysteine protease from *A. caninum* involved in hemoglobin digestion of parasite (Harrop et al, 1995, Loukas et al, 2004). Na-CP-2 and Na-CP-4 are homologues of Ac-CP-2 cloned by screening cDNA library of *N. americanus* with partial Ac-cp-2 cDNA (unpublished). Ac-APR-1 is a cathepsin D-like aspartic protease from *A. caninum* (Williamson et al, 2002, 2003; Loukas et al, 2005). Ac-MTP is an astacin-like metalloprotease secreted by the stimulated infective larvae of *A. caninum* (Zhan et al, 2002, Williamson et al, 2006, Mendez et al, 2005). Na-CTL is a C-type Lectin of *N. americanus* (Daub et al, 2000). Na-SAA-1 is a *N. americanus* orthologue of Ac-SAA-1, an immunodominant surface-associated antigen from *A. caninum* (Zhan et al, 2004). All recombinant proteins were expressed in *Pichia pastoris* as soluble secretory proteins and purified with chromatography except for Na-SAA-1 and Na-CP-2 that were expressed in *E. coli*. Recombinant Na-SAA-1 was soluble and Na-CP-2 was insoluble and denatured in the 0.1% SDS.

The hookworm recombinant proteins were formulated with adjuvants of either Freund's, ASO3 or Alhydrogel®. Complete and incomplete Freund's adjuvants were obtained from Sigma (Saint Louis, Mo.). Twenty-five µg of recombinant protein was emulsified with 100 µl of complete Freund's for each hamster for the first immunization and with incomplete Freund's for the boost. ASO3 is a water-oil adjuvant (Stoute et al, 1997) kindly provided by GlaxoSmithKline (Rixensart, Belgium). Total volume of 100 µl of ASO3 was formulated with 25 µg of recombinant protein for each hamster by mixing for 30 minutes at room temperature. Formulation of antigen with Alhydrogel® was performed by mixing 25 µg of the recombinant protein with 25 µl of 2% Alhydrogel® in a total volume of 200 µl for each hamster.

2.3 Vaccination

The dose of each vaccine given to each hamster was 25 µg recombinant protein formulated with different adjuvants (Freund's, ASO3 and Alhydrogel®) in a total volume of 200 µl. The vaccine was administrated subcutaneously and booted twice with two weeks interval. Total of 10-26 hamsters were immunized with one vaccine, the same number of hamsters were injected with the same volume of adjuvant alone on the same immunization schedule as a control group. For Freund's adjuvant, complete Freund's adjuvant was used in the initial immunization, followed by two boosts with incomplete Freund's adjuvant.

2.4 Challenge with the Third-Stage Infective Larvae of *N. americanus*

The third stage infective larvae of *N. americanus* were collected from coprocultures of feces from hamsters infected with *N. americanus* larvae (Xue, 2003a, b). One week after the last immunization, the hamsters (vaccine and adjuvant control groups) were infected with fresh 150 infective larvae subcutaneously under the skin of central abdomen.

2.5. Necropsy and Evaluation of Vaccine Effect

Twenty-five to twenty-eight days post challenge, all hamsters with vaccinated or control groups were sacrificed and the hookworms located in the small intestine were collected and counted. The mean worm burden in each group was calculated. The differences between each vaccinated group and the control group were analyzed by using Student t-test.

3. Results 3.1 Protective Immunity of rNa-ASP-2

In the first trial, the ASO3 was used as adjuvant. In rNa-ASP-2 (with his-tag) group, 26 hamsters were used and the mean worm burden was $11.7 \pm 9.2$, while $20.0 \pm 15.0$ worms were found in the adjuvant control group. The difference between the two groups was statistically significant ($P<0.05$) (Table 2).

In the second trial, the protective effects of rNa-ASP-2 with his-tag and without his-tag were compared. However, the adjuvant was changed to Anhydrogel instead of SO3. In this trial, the mean worm burden of adjuvant group was $37.7 \pm 13.6$, while those of rNa-ASP-2 (with his-tag) and rNa-ASP-2 (without his-tag) were $26.4 \pm 17.2$ and $27.1 \pm 28.3$, respectively. The difference of mean worm burdens between the rNa-ASP-2 (with his-tag) group and control group was statistically significant with a worm reduction rate of 30.0%. No significant difference was seen in mean worm burdens between the rNa-ASP-2 without his-tag and control group because of large standard deviation appeared in the vaccine group (Table 2).

Overall, the mean worm reduction rate combining the three trials is 31.8%, a statistically significant result when compared with the adjuvant only group.

TABLE 2

Protective immunity elicited by immunizing recombinant rNa-ASP-2
in hamsters challenged with *N. americanus* L3

| Trial# | Vaccine antigen | Vaccine mean worm ± SD (hamster#) | Control mean worm ± SD (hamster#) | Worm reduction rate (%) | P value |
|---|---|---|---|---|---|
| 1 | rNa-ASP-2 (with his-tag) | 11.7 ± 9.2 (26) | 20.0 ± 15.0 (26) | 41.5 | <0.05 |
| 2 | rNa-ASP-2 (with his-tag) | 26.4 ± 17.2 (20) | 37.7 ± 13.6 (20) | 30.0 | <0.05 |
| 3 | rNa-ASP-2 (w/o his-tag) | 27.1 ± 28.3 (20) | 37.7 ± 13.6 (20) | 28.1 | >0.05 |
| Total | | 21.7 ± 18.2 (66) | 31.8 ± 14.0 (66) | 31.8 | <0.05 |

3.2 Protective Immunity of rAc-GST-1 rAc-GST-1, the glutathione S-transferase-1 of *A. caninum*, was formulated with the adjuvant Alhydrogel® for immunization of hamsters. The dosage of rAc-GST-1 used for immunization was 25 μg/hamster. In the first test, the mean worm burden in the rAc-GST-1 immunization group was 15.7±9.8 which was less than that of 33.9±15.0 in the Alhydrogel® group, with a worm reduction of 53.7%. In the second test, the mean worm burden in the rAc-GST-1 group was 16.7±6.6 which was similar to that of 20.2±8.1 in the adjuvant group, with a worm reduction rate of 17.3%. Therefore, a third test was performed. The mean worm burden in the rAc-GST-1 immunization group was significantly lower than that in the nonimmunized group with a worm reduction rate of 71.3%. When the results from the three tests were combined together for calculation, the mean worm burden in the immunization group was also lower than that of the adjuvant group, with a worm reduction rate of 48.4% (Table 3).

TABLE 3

Protective immunity elicited by immunizing recombinant rAc-GST-1
in hamsters challenged with *N. americanus* L3

| Trial# | Vaccine antigen | Vaccine mean worm ± SD (hamster#) | Control mean worm ± SD (hamster#) | Worm reduction rate (%) | P value |
|---|---|---|---|---|---|
| 1 | rAc-GST-1 | 15.7 ± 9.8 (18) | 33.9 ± 15.0 (20) | 53.7 | <0.05 |
| 2 | rAc-GST-1 | 16.7 ± 6.6 (19) | 20.2 ± 8.1 (19) | 17.3 | >0.05 |
| 3 | rAc-GST-1 | 7.1 ± 7.8 (20) | 24.6 ± 10.5 (21) | 71.3 | <0.01 |
| Total | | 13.0 ± 9.0 (57) | 25.2 ± 13.0 (60) | 48.4 | <0.01 |

3.3 Protective Immunity of rNa-CP-2

Na-CP-2, cysteine protease-2 of *N. americanus*, was cloned by screening *N. americanus* L3 cDNA library with Ac-CP-2. The recombinant protein was expressed in *E. coli*. In the first trial, the mean worm burden in hamsters immunized with rNa-CP-2 was significantly lower than that in adjuvant group with worm reduction rate of 42%. In the repeat test, the difference of mean worm burdens between rNa-CP-2 group and adjuvant group was not significant. When the results of the two tests were combined together, the mean worm burden in rNa-CP-2 group was significantly lower than that in the adjuvant group (Table 4)

TABLE 4

Protective immunity elicited by immunizing recombinant rNa-CP-2
in hamsters challenged with *N. americanus* L3

| Trial# | Vaccine antigen | Vaccine mean worm ± SD (hamster#) | Control mean worm ± SD (hamster#) | Worm reduction rate (%) | P value |
|---|---|---|---|---|---|
| 1 | rNa-CP-2 | 26.6 ± 23.1 (20) | 45.9 ± 27.9 (21) | 42.0 | <0.05 |
| 2 | rNa-CP-2 | 31.8 ± 15.0 (20) | 36.7 ± 25.6 (12) | 13.4 | >0.05 |
| Total | | 29.2 ± 19.1 (40) | 42.4 ± 26.7 (33) | 31.1 | <0.05 |

3.4 Protective Immunity of rAc-APR-1

Ac-APR-1, aspartic protease-1 secreted by *A. caninum* adult worm, is a hemoglobinase for worm to digest host blood hemoglobin as resource of nutrition, therefore a good target for developing vaccine. Each hamster was immunized with 25 ug of recombinant Ac-APR-1 precipitated with 25 ul of 2% Alhydrogel®. After being boosted twice with the same formulation of recombinant Ac-APR-1, hamsters of vaccine and adjuvant group were challenged with 150 *N. americanus* L3. The mean worm burden of vaccinated group is 20.4±11.4 that is significantly lower than that from adjuvant control group (36.7±25.6) (Table 5)

TABLE 5

Protective immunity elicited by immunizing recombinant rAc-APR-1
in hamsters challenged with *N. americanus* L3

| Vaccine antigen | Adjuvant | Vaccine mean worm ± SD (hamster#) | Adjuvant mean worm ± SD (hamster#) | Worm reduction rate (%) | P value |
|---|---|---|---|---|---|
| rAc-APR-1 | Alhydrogel ® | 20.4 ± 11.4 (16) | 36.7 ± 25.6 (12) | 44.4.0 | <0.05 |

Conclusion: These results show that vaccination with recombinant Ac-APR-1 resulted in a marked decrease in worm burden after L3 challenge. Ac-APR-1 thus affords protection against challenge with hookworm larvae to vaccinated hamsters.

3.5 Other Hookworm Vaccine Trials

Other 6 hookworm antigens (rNa-ASP-1, rAc-CP-2, rNa-CTL, rAc-MTP, rNa-CP-4, and rNa-SAA-1) were tested for their protective immunity in the *N. americanus*-hamster model. The result showed no protective effect for all antigens listed above for hamsters to resist infection with *N. americanus* L3 (Table 6).

TABLE 6

Hookworm recovery from hamsters after being immunized with different hookworm recombinant proteins.

| Vaccine antigen | Adjuvant | Vaccine mean worm SD (hamster#) | Adjuvant mean worm ± SD (hamster#) | Worm Reduction rate (%) | P value |
| --- | --- | --- | --- | --- | --- |
| rNa-ASP-1 | Freund's | 29.1 ± 13.3 (8) | 18.4 ± 14.5 (8) | 0 | — |
| rAc-CP-2 | Freund's | 35.7 ± 19.1 (9) | 18.4 ± 14.5 (8) | 0 | — |
| rNa-CTL | Freund's | 25.4 ± 15.5 (8) | 18.4 ± 14.5 (8) | 0 | — |
| rAc-MTP | Alhydrogel ® | 32.4 ± 24.4 (20) | 45.9 ± 27.9 (21) | 29.4 | >0.05 |
| rNa-CP-4 | Alhydrogel ® | 20.5 ± 11.9 | 17.4 ± 13 (20) | 0 | — |
| rNa-SAA-1 | Alhydrogel ® | 19.2 ± 15.2 | 17.4 ± 13 (20) | 0 | — |

References For Example 4 de Silva N R, Brooker S, Hotez P J, Montresor A, Engels D, et al. Soil-transmitted helminth infections: Updating the global picture. Trends Parasitol. 2003; 19:547-551

J. Bethony, S. Brooker, M. Albonico, S. Geiger, A. Loukas, D. Diemert, P. Hotez. Soil-transmitted helminth infections: ascariasis, trichuriasis, and hookworm. The Lancet, 2006; Volume 367, Issue 9521, Pages 1521-1532

Peter J Hotez, Jeff Bethony, Maria Elena Bottazzi, Simon Brooker, and Paulo Buss Hookworm: "The Great Infection of Mankind" PLoS Med. 2005 March; 2(3):e67.

Hotez P J, Brooker S, Bethony J M, Bottazzi M E, Loukas A, Xiao S H. Hookworm infection. N Engl J Med 2004a; 351:799-807

D. A. Bundy et al., Hookworm infection in pregnancy, Trans. R. Soc. Trop. Med. Hyg. 89 (1995), pp. 521-522

H. E. Allen et al., New policies for using anthelmintics in high risk groups, Trends Parasitol. 18 (2002), pp. 381-382

World Health Organization (2002) Prevention and Control Of Schistosomiasis and Soil-Transmitted Helminthiasis. Report of a WHO expert committee. WHO Technical Report Series 912, p. 35, World Health Organization.

S. Brooker et al., The epidemiology of hookworm infection and its contribution to anaemia among pre-school children on the Kenyan coast, Trans. R. Soc. Trop. Med. Hyg. 93 (1999), pp. 240-246

L. S. Stephenson et al., Treatment with a single dose of albendazole improves growth of Kenyan schoolchildren with hookworm, *Trichuris trichiura*, and *Ascaris lumbricoides* infections, Am. J. Trop. Med. Hyg. 41 (1989), pp. 78-87.

A. Bhargava et al., Anthelmintic treatment improves the hemoglobin and serum ferritin concentrations of Tanzanian schoolchildren, Food Nutr. Bull. 24 (2003), pp. 332-342.

P. J. Hotez et al., Progress in the development of a recombinant vaccine for human hookworm disease: the Human Hookworm Vaccine Initiative, Int. J. Parasitol. 33 (2003a), pp. 1245-1258

Hotez, P. J., de Silva, N., Brooker, S., Bethony, J., 2003b, Soil-transmitted helminth infections: the nature, causes and burden of the condition. Working Paper No. 3, Disease Control Priorities Project. Fogarty International Center, National Institute of Health, Bethesda, Md.

Hotez P J, Zhan B, Loukas A, Bethony J M, Ashcom J, Ghosh K, Hawdon J M, Brandt W, Russell P K. Vaccines against human hookworm disease (Chapter 77). In: NEW GENERATION VACCINES THIRD EDITION, REVISED AND EXPANDED (eds. Levine M M, Kaper J B, Rappuoli R, Liu M, Good M). New York: Marcel Dekker 2004b; pp. 937-51.

Hawdon J. M., Jones B. F., Hoffman D. R., Hotez P. J., 1996. Cloning and characterization of *Ancylostoma* secreted protein: a novel protein associated with the transition to parasitism by infective hookworm larvae. J Biol Chem 271: 6672-8.

Hawdon J. M., Narasimhan S., Hotez P. J., 1999. *Ancylostoma* secreted protein 2: cloning and characterization of a second member of a family of nematode secreted proteins from *Ancylostoma caninum*. Mol Biochem Parasitol 99: 149-65

J. Bethony et al., Antibodies against a secreted protein from hookworm larvae reduce the intensity of hookworm infection in humans and vaccinated laboratory animals, FASEB J. 19 (2005), pp. 1743-1745

P. J. Hotez, China's hookworms, China Q. 172 (2002), pp. 1029-1041

M. Albonico et al., Monitoring drug efficacy and early detection of drug resistance in human soil-transmitted nematodes: a pressing public health agenda for helminth control, Int. J. Parasitol. 34 (2004), pp. 1205-1210.

Goud G N, Bottazzi M E, Zhan B, Mendez S, Deumic V, Plieskatt J, Liu S, Wang Y, Bueno L, Fujiwara R, Samuel A, Ahn S Y, Solanki M, Asojo O A, Wang J, Bethony J M, Loukas A, Roy M, Hotez P J. Expression of the *Necator americanus* hookworm larval antigen Na-ASP-2 in *Pichia pastoris* and purification of the recombinant protein for use in human clinical trials. Vaccine 2005; 23:4754-4764

G. N. Goud et al., Cloning, yeast expression, isolation, and vaccine testing of recombinant *Ancylostoma* secreted protein (ASP)-1 and ASP-2 from *Ancylostoma ceylanicum*, J. Infect. Dis. 189 (2004), pp. 919-929

Alex Loukas, Jeffrey M. Bethony, Angela L. Williamson, Gaddam N. Goud, Susana Mendez, Bin Zhan, John M. Hawdon, Maria Elena Bottazzi, Paul J. Brindley, and Peter J. Hotez. Vaccination of Dogs with a Recombinant Cysteine Protease from the Intestine of Canine Hookworms Diminishes the Fecundity and Growth of Worms The Journal of Infectious Diseases 2004; 189:1952-1961

Loukas A, Bethony J M, Mendez S, Fujiwara R T, Goud G N, Ranjit N, Zhan B, Jones K, Bottazzi M E, Hotez P J.

Vaccination with recombinant aspartic hemoglobinase reduces parasite load and blood loss after hookworm infection in dogs. PLoS Med. 2005; 2(10):e295.

Ricardo T. Fujiwara, Bin Zhan, Susana Mendez, Alex Loukas, Lilian L. Bueno, Yan Wang, Jordan Plieskatt, Yelena Oksov, Sara Lustigman, Maria Elena Bottazzi, Peter Hotez and Jeffrey M. Bethony. Reduction of worm fecundity and anemia by vaccination with recombinant Ac-16, an antigen expressed across all developmental stages of hookworm, JID (in press)

Xue Jian, Xiao Shu-Hua, Qiang Hui-qing, Liu Sen, Peter Hotez, Shen Bing-Gui, Xue Hai-Chou, Li Tie-Hua and Zhan Bin. Necator americanus: maintenance through one hundred generations in golden hamsters (Mesocricetus auratus). II. Morphological development of the adult and its comparison with humans. Exp. Parasitol. 2003a; 105(3-4): 192-200.

Xue, J., Liu, S., Qiang, H. Q., Ren, H. N., Li, T. H., Xue, H. C., Hotez, P. J. and Xiao, S. H., 2003b. Necator americanus: maintenance through one hundred generations in golden hamsters (Mesocricetus auratus). I. Host sex-associated differences in hookworm burden and fecundity. Experimental Parasitology 104, pp. 62-66.

Jian Xue, Hui-Qing Quang, Jun-Ming Yao, Ricardo Fujiwara, Bin Zhan, Peter Hotez and Shu-Hua Xiao. Necator americanus: Optimization of the golden hamster model for testing anthelmintic drugs. Experimental Parasitology. 2005; 111(4):219-23.

Timothy, L. M. and Behnke, J. M., 1993. Necator americanus in inbred mice: a re-evaluation of primary infection kinetics. Parasitology 107, pp. 425-431.

Timothy, L. M. and Behnke, J. M., 1997. Necator americanus in inbred mice: evidence in support of genetically determined differences in the cellular immune response to a primary infection. Parasitology 114, pp. 53-63.

Yoshida, Y. K. and Fukutome, S., 1967. Experimental infection of rabbits with the human hookworm Necator americanus. Journal of Parasitology 53, pp. 1067-1073

Yoshida, Y. K., Okamoto, K., Higo, A. and Ima, K., 1960. Studies on the development of Necator americanus in young dogs. Japanese Journal of Parasitology 9, pp. 735-743.

Sen, H. G., 1972. Necator americanus: behaviour in hamsters. Experimental Parasitology 32, pp. 26-32.

Sen, H. G. and Seth, D., 1970. Development of Necator americanus in golden hamsters Mesocricetus auratus. Indian Journal Medicine Research 58, pp. 1356-1360.

Sen, H. G. and Deb, B. N., 1973. Effect of cortisone upon serial passage with the human hookworm, Necator americanus in golden hamsters, Mesocricetus auratus. Indian Journal of Medicine Research 61, pp. 486-494.

Nagahana, M., Yoshida, Y., Tanabe, K., Komdo, K., Pkawoto, K., Okada, S., Sato, K., Ito, S., Fukutome, S., Ishikawa, M., 1962. Experimental studies on the oral infection of Necator americanus I. Per stomach infection of puppies and guinea pigs with N. americanus larvae. Japanese Journal of Parasitology 11, 454-460

Bin Zhan, Peter J Hotez, Yan Wang and John M Hawdon. A developmentally regulated metalloprotease secreted by host-stimulated Ancylostoma caninum third-stage infective larvae is a member of the astacin family of protease. Mol. Biochem. Parasitol. 2002; 120:291-296

Williamson A L, Lustigman S, Oksov Y, Deumic V, Plieskatt J, Mendez S, Zhan B, Bottazzi M E, Hotez P J, Loukas A. Ancylostoma caninum MTP-1, an astacin-like metalloprotease secreted by infective hookworm larvae, is involved in tissue migration. Infect Immun. 2006, 74(2):961-7.

Bin Zhan, Yan Wang, Yueyuan Liu, Angela Williamson, Alex Loukas, John M. Hawdon, Xue Hae-chou, Xiao Shu-hua, and Peter J. Hotez. Ac-SAA-1, an immunodominant 16 kDa surface-associated antigen of infective larvae and adults of Ancylostoma caninum. Int. J. Parasitol. 2004; 34:1037-45

Zhan B, Liu S, Perally S, Xue J, Fujiwara R, Brophy P, Xiao S, Liu Y, Feng J, Williamson A, Wang Y, Bueno L L, Mendez S, Goud G, Bethony J M, Hawdon J M, Loukas A, Jones K, Hotez P J. Biochemical characterization and vaccine potential of a heme binding glutathione transferase (GST) from the adult hookworm Ancylostoma caninum. Infection and Immunity 2005; 73(10):6903-11

Susana Mendez, Bin Zhan, Gaddam Goud, Kashinath Ghosh, Azra Dobardzic, Wenhui Wu, Sen Liu, Vehid Deumic, Reshad Dobardzic, Yueyuan Liu, Jeff Bethony and Peter J. Hotez Effect of combining the larval antigens Ancylostoma Secreted Protein 2 (ASP-2) and metalloprotease 1 (MTP-1) in protecting hamsters against hookworm infection and disease caused by Ancylostoma ceylanicum. Vaccine. 2005; 23:3123-30

Harrop S A, Sawangjaroen N, Prociv P, Brindley P J. Characterization and localization of cathepsin B proteinases expressed by adult Ancylostoma caninum hookworms. Mol Biochem Parasitol 1995; 71:163 71

Williamson A L, Lecchi P, Turk B E, Choe Y, Hotez P J, et al. A multi-enzyme cascade of hemoglobin proteolysis in the intestine of blood-feeding hookworms. J Biol. Chem. 2004; 279:35950-35957.

Williamson A L, Brindley P J, Abbenante G, Prociv P, Berry C, et al. Cleavage of hemoglobin by hookworm cathepsin D aspartic proteases and its potential contribution to host specificity. FASEB J. 2002; 16:1458-1460

Daub J, Loukas A, Pritchard D I, Blaxter M A survey of genes expressed in adults of the human hookworm, Necator americanus. Parasitology. 2000 February; 120 (Pt 2):171-84.

Stoute J A, Slaoui M, Heppner D G, Momin P, Kester K E, et al. A preliminary evaluation of a recombinant circumsporozoite protein vaccine against Plasmodium falciparum malaria. RTS, S Malaria Vaccine Evaluation Group. N Engl J. Med. 1997; 336:86-91.

Example 5

Further Evaluations

An innovative scoring system has been used to select larval antigens for use in the practice of the invention. The criteria were based on five criteria including an evaluation of the antigen in preclinical studies to 1) reduce host worm burdens, 2) reduce host blood loss, 3) reduce fecal egg counts, and 4) for antibody to inhibit larval invasion in vitro. The fifth criterion was 5) whether there are known orthologues that protect in veterinary vaccines and the sixth criterion was 6) the feasibility and ease of expression, yield and stability. Other factors under consideration included a known function and mechanism of action, association with reductions in risk of acquiring heavy hookworm infection in endemic setting, and immunoepidemiology. The results are presented in tabular form in FIGS. 20 and 21. By these rankings, ASP-2 (a L3 secreted antigen) and SAA-2 (a L3 surface antigen) emerged as the two lead candidate larval antigens and APR-1 and GST-1 emerged as the lead candidate adult antigens, with CP-2/3 (cysteine protease) and Cys (cystatin) as viable backup antigens.

We claim:

1. An immunogenic composition, comprising:
isolated substantially purified recombinant hookworm antigens *Necator americanus* aspartic protease 1 (Na-APR-1) and *Necator americanus* glutathione S transferase 1 (Na-GST-1), wherein
said Na-APR-1 hookworm antigen has the amino acid sequence as set forth in SEQ ID NO: 4 or SEQ ID NO: 6 or SEQ NO: 10 or SEQ NO: 12 or SEQ ID NO: 14 or SEQ ID NO: 16, and said Na-GST-1 hookworm antigen has the amino acid sequence as set forth in SEQ ID NO: 18.

* * * * *

SEQUENCE LISTING

<160> NUMBER OF SEQ ID NOS: 34

<210> SEQ ID NO 1
<211> LENGTH: 753
<212> TYPE: DNA
<213> ORGANISM: Necator americanus

<400> SEQUENCE: 1

```
gaaaatcaca atgatgtctt ctatcacatg tttggttctt ctctcgattg cagcgtactc      60
caaagccggt tgtcctgaca atggaatgtc agaggaagca cggcaaaaat tccttgaatt     120
gcacaattcg ttgagaagtt cggttgcatt gggacaggcc aaggatggag ctggtggaaa     180
tgccccgaaa gctgctaaga tgaagacgat ggcatacgat tgcgaagttg aaaagactgc     240
aatgaataac gcgaaacaat gtgtattcaa gcactcgcaa cctaaccaaa ggaaaggatt     300
gggagagaat atatttatgt cttcggatag cggtatggac aaagcaaagg ctgctgagca     360
ggctagcaaa gcttggttcg gcgaacttgc agaaaaagga gttggacaga atcttaagct     420
tacaggaggc ttgttcagca gaggagtcgg gcactataca cagatggtat ggcaagaaac     480
cgttaagctt ggatgctatg tggaagcgtg ctcaaatatg tgttatgtgg tgtgccagta     540
cggtcctgct ggaaatatga tgggcaagga tatctacgag aaaggagaac cgtgttcgaa     600
atgtgagaat tgcgacaagg agaagggact ctgcagtgct tgattagttg tgttcagtga     660
agctcattac gctcacatac tttaacaaat cgtagtgatc tgtagttgct ttaatattca     720
aataaacatg atgccagcaa aaaaaaaaaa aaa                                   753
```

<210> SEQ ID NO 2
<211> LENGTH: 207
<212> TYPE: PRT
<213> ORGANISM: Necator americanus

<400> SEQUENCE: 2

```
Met Ser Ser Ile Thr Cys Leu Val Leu Leu Ser Ile Ala Ala Tyr Ser
1               5                   10                  15

Lys Ala Gly Cys Pro Asp Asn Gly Met Ser Glu Glu Ala Arg Gln Lys
            20                  25                  30

Phe Leu Glu Leu His Asn Ser Leu Arg Ser Ser Val Ala Leu Gly Gln
        35                  40                  45

Ala Lys Asp Gly Ala Gly Gly Asn Ala Pro Lys Ala Ala Lys Met Lys
    50                  55                  60

Thr Met Ala Tyr Asp Cys Glu Val Glu Lys Thr Ala Met Asn Asn Ala
65                  70                  75                  80

Lys Gln Cys Val Phe Lys His Ser Gln Pro Asn Gln Arg Lys Gly Leu
                85                  90                  95

Gly Glu Asn Ile Phe Met Ser Ser Asp Ser Gly Lys Ala Lys Ala Ala
            100                 105                 110

Glu Gln Ala Ser Lys Ala Trp Phe Gly Glu Leu Ala Glu Lys Gly Val
        115                 120                 125

Gly Gln Asn Leu Lys Leu Thr Gly Gly Leu Phe Ser Arg Gly Val Gly
    130                 135                 140

His Tyr Thr Gln Met Val Trp Gln Glu Thr Val Lys Leu Gly Cys Tyr
145                 150                 155                 160

Val Glu Ala Cys Ser Asn Met Cys Tyr Val Val Cys Gln Tyr Gly Pro
                165                 170                 175

Ala Gly Asn Met Met Gly Lys Asp Ile Tyr Glu Lys Gly Glu Pro Cys
```

```
            180                 185                 190
Ser Lys Cys Glu Asn Cys Asp Lys Glu Lys Gly Leu Cys Ser Ala
        195                 200                 205

<210> SEQ ID NO 3
<211> LENGTH: 1293
<212> TYPE: DNA
<213> ORGANISM: Necator americanus

<400> SEQUENCE: 3
agcgttcatc gacgactctt tcatcaagct cgtcgtcatg tgacatcggt atcgctttcg      60
cgtcagccaa cacttcgtga acgactgatc gcaagtggca gttgggagga ttaccagaaa     120
caacgctacc attatcaaaa gaaaattcta gcaaaatatg ctgctaacaa agcgtcaaag     180
ttacaatctg caaacgagat cgatgaattg ctccggaact atatggatgc acaatactat     240
ggtgtcatcc aaattgggac tccagctcag aatttcactg tgatcttcga cacgggttcc     300
tcaaatctat gggtaccgtc aagaaagtgt ccattctatg acattgcatg tatgcttcat     360
catcgttatg actccggagc ctcgtcaacc tgcaaggaag atgggcgcaa gatggctatt     420
cagtatggaa ctggatctat gaaggattca tttctaagg atattgtttg tattgctgga     480
atttgcgctg aagaacaacc tttcgcggag ctacaagtg aacctggtct acatttatc      540 gctgctaagt tgatggaat ccttggaatg cattcccgg aaattgctgt ctcggtgta       600 actcctgtct ccatacgtt cattgaacag aagaaagttc ctagccctgt gtttgctttc     660
tggccgaata ggaatccaga gtcggaaatt ggaggagaga ttacctttgg tggtgtggat     720
acccgacgtt atgttgaacc aattacatgg acaccagtga cacgtcgtgg atattggcaa     780
ttcaaaatgg atatggtaca aggtggttca tcgtccattg cgtgtccgaa tggatgccaa     840
gctatcgctg atactggcac ttctcttatt gctggaccga aggcacaggt tgaggcaatc     900
cagaaatata tcggagcaga gccgcttatg aaaggagaat acatgattcc ttgcgacaaa     960
gtaccatccc ttcctgatgt ttcgttcatc atcgatggca agacgtttac actcaaaggg    1020
gaagattacg ttctaaccgt gaaagccgct ggtaaatcaa tctgtttgtc tggcttcatg    1080
ggaatggact tcccagagaa gatcggcgaa ttgtggatcc ttggagatgt tttcattgga    1140
aaatactaca ccgtcttcga tgttggtcag gcacgtgttg gatttgctca agcaaagtca    1200
gaagatggat tccctgttgg gaccccgtt cgaacattca gacagcttca ggaagacagc    1260
gatagcgacg aggacgatgt atttactttt taa                                 1293

<210> SEQ ID NO 4
<211> LENGTH: 430
<212> TYPE: PRT
<213> ORGANISM: Necator americanus

<400> SEQUENCE: 4

Ser Val His Arg Arg Leu Phe His Gln Ala Arg Arg His Val Thr Ser
1               5                   10                  15

Val Ser Leu Ser Arg Gln Pro Thr Leu Arg Glu Arg Leu Ile Ala Ser
            20                  25                  30

Gly Ser Trp Glu Asp Tyr Gln Lys Gln Arg Tyr His Tyr Gln Lys Lys
        35                  40                  45

Ile Leu Ala Lys Tyr Ala Ala Asn Lys Ala Ser Lys Leu Gln Ser Ala
    50                  55                  60

Asn Glu Ile Asp Glu Leu Leu Arg Asn Tyr Met Asp Ala Gln Tyr Tyr
65                  70                  75                  80
```

Gly Val Ile Gln Ile Gly Thr Pro Ala Gln Asn Phe Thr Val Ile Phe
            85                  90                  95

Asp Thr Gly Ser Ser Asn Leu Trp Val Pro Ser Arg Lys Cys Pro Phe
            100                 105                 110

Tyr Asp Ile Ala Cys Met Leu His His Arg Tyr Asp Ser Gly Ala Ser
            115                 120                 125

Ser Thr Cys Lys Glu Asp Gly Arg Lys Met Ala Ile Gln Tyr Gly Thr
            130                 135                 140

Gly Ser Met Lys Gly Phe Ile Ser Lys Asp Ile Val Cys Ile Ala Gly
145                 150                 155                 160

Ile Cys Ala Glu Glu Gln Pro Phe Ala Glu Ala Thr Ser Glu Pro Gly
            165                 170                 175

Leu Thr Phe Ile Ala Ala Lys Phe Asp Gly Ile Leu Gly Met Ala Phe
            180                 185                 190

Pro Glu Ile Ala Val Leu Gly Val Thr Pro Val Phe His Thr Phe Ile
            195                 200                 205

Glu Gln Lys Lys Val Pro Ser Pro Val Phe Ala Phe Trp Pro Asn Arg
            210                 215                 220

Asn Pro Glu Ser Glu Ile Gly Gly Ile Thr Phe Gly Gly Val Asp
225                 230                 235                 240

Thr Arg Arg Tyr Val Glu Pro Ile Thr Trp Thr Pro Val Thr Arg Arg
            245                 250                 255

Gly Tyr Trp Gln Phe Lys Met Asp Met Val Gln Gly Ser Ser Ser
            260                 265                 270

Ile Ala Cys Pro Asn Gly Cys Gln Ala Ile Ala Asp Thr Gly Thr Ser
            275                 280                 285

Leu Ile Ala Gly Pro Lys Ala Gln Val Glu Ala Ile Gln Lys Tyr Ile
            290                 295                 300

Gly Ala Glu Pro Leu Met Lys Gly Glu Tyr Met Ile Pro Cys Asp Lys
305                 310                 315                 320

Val Pro Ser Leu Pro Asp Val Ser Phe Ile Ile Asp Gly Lys Thr Phe
            325                 330                 335

Thr Leu Lys Gly Glu Asp Tyr Val Leu Thr Val Lys Ala Ala Gly Lys
            340                 345                 350

Ser Ile Cys Leu Ser Gly Phe Met Gly Met Asp Phe Pro Glu Lys Ile
            355                 360                 365

Gly Glu Leu Trp Ile Leu Gly Asp Val Phe Ile Gly Lys Tyr Tyr Thr
            370                 375                 380

Val Phe Asp Val Gly Gln Ala Arg Val Gly Phe Ala Gln Ala Lys Ser
385                 390                 395                 400

Glu Asp Gly Phe Pro Val Gly Thr Pro Val Arg Thr Phe Arg Gln Leu
            405                 410                 415

Gln Glu Asp Ser Asp Ser Asp Glu Asp Asp Val Phe Thr Phe
            420                 425                 430

<210> SEQ ID NO 5
<211> LENGTH: 1441
<212> TYPE: DNA
<213> ORGANISM: Necator americanus

<400> SEQUENCE: 5
ggcacgaggg gagatggctc gacttgtatt cctactcgta ctatgtactc tggctgcaca      60
agcgttcatc gacgactctt tcatcaagct cgtcgtcatg tgacatcggt atcgctttcg     120
cgtcagccaa cacttcgtga acgactgatc gcaagtggca gttgggagga ttaccagaaa     180

```
caacgctacc attatcgaaa gaaaattcta gcaaaatatg ctgctaacaa agcgtcaaag    240
ttacaatctg caaacgagat cgatgaattg ctccggaact atatggatgc acaatactat    300
ggtgtcatcc aaattgggac tccagctcag aatttcactg tgatcttcga cacgggttcc    360
tcaaatctat gggtaccgtc aagaaagtgt ccattctatg acattgcatg tatgcttcat    420
catcgttatg actccggagc tcgtcaacc tacaaggaag atgggcgcaa gatggctatt     480
cagtatggaa ctggatctat gaaggattc atttctaagg atattgtttg tattgctgga     540
atttgcgctg aagaacaacc tttcgcggag ctacaagtg aacctggtct acatttatc     600
gctgctaagt ttgatggaat ccttggaatg cattcccgg aaattgctgt ctcggtgta     660
actcctgtct tccatacgtt cattgaacag aagaaagttc ctagccctgt gtttgctttc    720
tggctgaata ggaatccaga gtcggaaatt ggaggagaga ttacctttgg tggtgtggat    780
acccgacgtt atgttgaacc aattacatgg acaccagtga cacgtcgtgg atattggcaa    840
ttcaaaatgg atatggtaca aggtggttca tcgtccattg cgtgtccgaa tggatgccaa    900
gctatcgctg atactggcac ttctcttatt gctggaccga aggcacaggt tgaggcaatc    960
cagaaatata tcggagcaga gccgcttatg aaaggagaat acatgattcc ttgcgacaaa   1020
gtaccatccc ttcctgatgt ttcgttcatc atcgatggca agacgtttac actcaaaggg   1080
gaagattacg ttctaaccgt gaaagccgct ggtaaatcaa tctgtttgtc tggcttcatg   1140
ggaatggact cccagagaa gatcggcgaa ttgtggatcc ttggagatgt tttcattgga   1200
aaatactaca ccgtcttcga tgttggtcag gcacgtgttg gatttgctca agcaaagtca   1260
gaagatggat tccctgttgg cacccccgtt cgaacattca gacagcttca ggaagacagc   1320
gatagcgacg aggacgatgt atttacttt taagtagtgt taacatctcc aacgtgctct    1380
gttacttcta cgtgtaccat gtttcacgtg tttgctcatt tgataaatta ttatcttccc   1440
t                                                                  1441

<210> SEQ ID NO 6
<211> LENGTH: 446
<212> TYPE: PRT
<213> ORGANISM: Necator americanus

<400> SEQUENCE: 6

Met Ala Arg Leu Val Phe Leu Leu Val Leu Cys Thr Leu Ala Ala Ala
1               5                   10                  15

Ser Val His Arg Arg Leu Phe His Gln Ala Arg Arg His Val Thr Ser
            20                  25                  30

Val Ser Leu Ser Arg Gln Pro Thr Leu Arg Glu Arg Leu Ile Ala Ser
        35                  40                  45

Gly Ser Trp Glu Asp Tyr Gln Lys Gln Arg Tyr His Tyr Arg Lys Lys
    50                  55                  60

Ile Leu Ala Lys Tyr Ala Ala Asn Lys Ala Ser Lys Leu Gln Ser Ala
65                  70                  75                  80

Asn Glu Ile Asp Glu Leu Leu Arg Asn Tyr Met Asp Ala Gln Tyr Tyr
                85                  90                  95

Gly Val Ile Gln Ile Gly Thr Pro Ala Gln Asn Phe Thr Val Ile Phe
            100                 105                 110

Asp Thr Gly Ser Ser Asn Leu Trp Val Pro Ser Arg Lys Cys Pro Phe
        115                 120                 125

Tyr Asp Ile Ala Cys Met Leu His His Arg Tyr Asp Ser Gly Ala Ser
    130                 135                 140

Ser Thr Tyr Lys Glu Asp Gly Arg Lys Met Ala Ile Gln Tyr Gly Thr
```

```
                145                 150                 155                 160
Gly Ser Met Lys Gly Phe Ile Ser Lys Asp Ile Val Cys Ile Ala Gly
                    165                 170                 175

Ile Cys Ala Glu Glu Gln Pro Phe Ala Glu Ala Thr Ser Glu Pro Gly
                180                 185                 190

Leu Thr Phe Ile Ala Ala Lys Phe Asp Gly Ile Leu Gly Met Ala Phe
                195                 200                 205

Pro Glu Ile Ala Val Leu Gly Val Thr Pro Val Phe His Thr Phe Ile
            210                 215                 220

Glu Gln Lys Lys Val Pro Ser Pro Val Phe Ala Phe Trp Leu Asn Arg
225                 230                 235                 240

Asn Pro Glu Ser Glu Ile Gly Gly Glu Ile Thr Phe Gly Gly Val Asp
                    245                 250                 255

Thr Arg Arg Tyr Val Glu Pro Ile Thr Trp Thr Pro Val Thr Arg Arg
                260                 265                 270

Gly Tyr Trp Gln Phe Lys Met Asp Met Val Gln Gly Ser Ser Ser
                275                 280                 285

Ile Ala Cys Pro Asn Gly Cys Gln Ala Ile Ala Asp Thr Gly Thr Ser
            290                 295                 300

Leu Ile Ala Gly Pro Lys Ala Gln Val Glu Ala Ile Gln Lys Tyr Ile
305                 310                 315                 320

Gly Ala Glu Pro Leu Met Lys Gly Glu Tyr Met Ile Pro Cys Asp Lys
                    325                 330                 335

Val Pro Ser Leu Pro Asp Val Ser Phe Ile Ile Asp Gly Lys Thr Phe
                340                 345                 350

Thr Leu Lys Gly Glu Asp Tyr Val Leu Thr Val Lys Ala Ala Gly Lys
                355                 360                 365

Ser Ile Cys Leu Ser Gly Phe Met Gly Met Asp Phe Pro Glu Lys Ile
            370                 375                 380

Gly Glu Leu Trp Ile Leu Gly Asp Val Phe Ile Gly Lys Tyr Tyr Thr
385                 390                 395                 400

Val Phe Asp Val Gly Gln Ala Arg Val Gly Phe Ala Gln Ala Lys Ser
                    405                 410                 415

Glu Asp Gly Phe Pro Val Gly Thr Pro Val Arg Thr Phe Arg Gln Leu
                420                 425                 430

Gln Glu Asp Ser Asp Ser Asp Glu Asp Val Phe Thr Phe
                435                 440                 445

<210> SEQ ID NO 7
<211> LENGTH: 430
<212> TYPE: PRT
<213> ORGANISM: Necator americanus

<400> SEQUENCE: 7

Ser Val His Arg Arg Leu Phe His Gln Ala Arg Arg His Val Thr Ser
1               5                   10                  15

Val Ser Leu Ser Arg Gln Pro Thr Leu Arg Glu Arg Leu Ile Ala Ser
                20                  25                  30

Gly Ser Trp Glu Asp Tyr Gln Lys Gln Arg Tyr His Tyr Arg Lys Lys
            35                  40                  45

Ile Leu Ala Lys Tyr Ala Ala Asn Lys Ala Ser Lys Leu Gln Ser Ala
        50                  55                  60

Asn Glu Ile Asp Glu Leu Leu Arg Asn Tyr Met Asp Ala Gln Tyr Tyr
65                  70                  75                  80

Gly Val Ile Gln Ile Gly Thr Pro Ala Gln Asn Phe Thr Val Ile Phe
```

```
                    85                  90                  95
Asp Thr Gly Ser Ser Asn Leu Trp Val Pro Ser Arg Lys Cys Pro Phe
                100                 105                 110

Tyr Asp Ile Ala Cys Met Leu His His Arg Tyr Asp Ser Gly Ala Ser
            115                 120                 125

Ser Thr Tyr Lys Glu Asp Gly Arg Lys Met Ala Ile Gln Tyr Gly Thr
        130                 135                 140

Gly Ser Met Lys Gly Phe Ile Ser Lys Asp Ile Val Cys Ile Ala Gly
145                 150                 155                 160

Ile Cys Ala Glu Glu Gln Pro Phe Ala Glu Ala Thr Ser Glu Pro Gly
                165                 170                 175

Leu Thr Phe Ile Ala Ala Lys Phe Asp Gly Ile Leu Gly Met Ala Phe
            180                 185                 190

Pro Glu Ile Ala Val Leu Gly Val Thr Pro Val Phe His Thr Phe Ile
        195                 200                 205

Glu Gln Lys Lys Val Pro Ser Pro Val Phe Ala Phe Trp Leu Asn Arg
    210                 215                 220

Asn Pro Glu Ser Glu Ile Gly Gly Glu Ile Thr Phe Gly Gly Val Asp
225                 230                 235                 240

Thr Arg Arg Tyr Val Glu Pro Ile Thr Trp Thr Pro Val Thr Arg Arg
                245                 250                 255

Gly Tyr Trp Gln Phe Lys Met Asp Met Val Gln Gly Ser Ser
            260                 265                 270

Ile Ala Cys Pro Asn Gly Cys Gln Ala Ile Ala Asp Thr Gly Thr Ser
        275                 280                 285

Leu Ile Ala Gly Pro Lys Ala Gln Val Glu Ala Ile Gln Lys Tyr Ile
    290                 295                 300

Gly Ala Glu Pro Leu Met Lys Gly Glu Tyr Met Ile Pro Cys Asp Lys
305                 310                 315                 320

Val Pro Ser Leu Pro Asp Val Ser Phe Ile Asp Gly Lys Thr Phe
                325                 330                 335

Thr Leu Lys Gly Glu Asp Tyr Val Leu Thr Val Lys Ala Ala Gly Lys
            340                 345                 350

Ser Ile Cys Leu Ser Gly Phe Met Gly Met Asp Phe Pro Glu Lys Ile
        355                 360                 365

Gly Glu Leu Trp Ile Leu Gly Asp Val Phe Ile Gly Lys Tyr Tyr Thr
    370                 375                 380

Val Phe Asp Val Gly Gln Ala Arg Val Gly Phe Ala Gln Ala Lys Ser
385                 390                 395                 400

Glu Asp Gly Phe Pro Val Gly Thr Pro Val Arg Thr Phe Arg Gln Leu
                405                 410                 415

Gln Glu Asp Ser Asp Ser Asp Glu Asp Val Phe Thr Phe
            420                 425                 430

<210> SEQ ID NO 8
<211> LENGTH: 430
<212> TYPE: PRT
<213> ORGANISM: Necator americanus

<400> SEQUENCE: 8

Ser Val His Arg Arg Leu Phe His Gln Ala Arg His Val Thr Ser
1               5                  10                  15

Val Ser Leu Ser Arg Gln Pro Thr Leu Arg Glu Arg Leu Ile Ala Ser
            20                  25                  30

Gly Ser Trp Glu Asp Tyr Gln Lys Gln Arg Tyr His Tyr Gln Lys Lys
```

```
                35                  40                  45
Ile Leu Ala Lys Tyr Ala Ala Asn Lys Ala Ser Lys Leu Gln Ser Ala
 50                  55                  60

Asn Glu Ile Asp Glu Leu Leu Arg Asn Tyr Met Asp Ala Gln Tyr Tyr
 65                  70                  75                  80

Gly Val Ile Gln Ile Gly Thr Pro Ala Gln Asn Phe Thr Val Ile Phe
                 85                  90                  95

Asp Thr Gly Ser Ser Asn Leu Trp Val Pro Ser Arg Lys Cys Pro Phe
                100                 105                 110

Tyr Asp Ile Ala Cys Met Leu His His Arg Tyr Asp Ser Gly Ala Ser
                115                 120                 125

Ser Thr Cys Lys Glu Asp Gly Arg Lys Met Ala Ile Gln Tyr Gly Thr
                130                 135                 140

Gly Ser Met Lys Gly Phe Ile Ser Lys Asp Ile Val Cys Ile Ala Gly
145                 150                 155                 160

Ile Cys Ala Glu Glu Gln Pro Phe Ala Glu Ala Thr Ser Glu Pro Gly
                165                 170                 175

Leu Thr Phe Ile Ala Ala Lys Phe Asp Gly Ile Leu Gly Met Ala Phe
                180                 185                 190

Pro Glu Ile Ala Val Leu Gly Val Thr Pro Val Phe His Thr Phe Ile
                195                 200                 205

Glu Gln Lys Lys Val Pro Ser Pro Val Phe Ala Phe Trp Pro Asn Arg
                210                 215                 220

Asn Pro Glu Ser Glu Ile Gly Gly Ile Thr Phe Gly Gly Val Asp
225                 230                 235                 240

Thr Arg Arg Tyr Val Glu Pro Ile Thr Trp Thr Pro Val Thr Arg Arg
                245                 250                 255

Gly Tyr Trp Gln Phe Lys Met Asp Met Val Gln Gly Ser Ser Ser
                260                 265                 270

Ile Ala Cys Pro Asn Gly Cys Gln Ala Ile Ala Asp Thr Gly Thr Ser
                275                 280                 285

Leu Ile Ala Gly Pro Lys Ala Gln Val Glu Ala Ile Gln Lys Tyr Ile
290                 295                 300

Gly Ala Glu Pro Leu Met Lys Gly Glu Tyr Met Ile Pro Cys Asp Lys
305                 310                 315                 320

Val Pro Ser Leu Pro Asp Val Ser Phe Ile Ile Asp Gly Lys Thr Phe
                325                 330                 335

Thr Leu Lys Gly Glu Asp Tyr Val Leu Thr Val Lys Ala Ala Gly Lys
                340                 345                 350

Ser Ile Cys Leu Ser Gly Phe Met Gly Met Asp Phe Pro Glu Lys Ile
                355                 360                 365

Gly Glu Leu Trp Ile Leu Gly Asp Val Phe Ile Gly Lys Tyr Tyr Thr
                370                 375                 380

Val Phe Asp Val Gly Gln Ala Arg Val Gly Phe Ala Gln Ala Lys Ser
385                 390                 395                 400

Glu Asp Gly Phe Pro Val Gly Thr Pro Val Arg Thr Phe Arg Gln Leu
                405                 410                 415

Gln Glu Asp Ser Asp Ser Asp Glu Asp Asp Val Phe Thr Phe
                420                 425                 430

<210> SEQ ID NO 9
<211> LENGTH: 1290
<212> TYPE: DNA
<213> ORGANISM: Necator americanus
```

<400> SEQUENCE: 9

```
tctgttcaca gaagattgtt tcatcaagct agaagacacg ttacttcagt ttccttgtcc        60
agacaaccaa ctttgagaga gagattgatt gcttcaggtt catgggaaga ctaccaaaaa       120
caaagatatc attacagaaa gaagattttg gctaagtacg ctgctaataa ggcttctaag       180
ttgcaatctg ctaacgagat tgatgaattg ttgagaaatt atatggatgc tcaatattat       240
ggagttattc aaattggaac accagctcaa aattttactg ttattttcga cactggatcc       300
tcaaacttgt gggttccttc aagaaaatgt ccttctatg acattgcttg tatgttgcac        360
cacagatacg actctggagc ttcctccaca tacaaagaag atggaagaaa gatggctatt       420
caatatggta caggatccat gaaaggtttc atttccaaag acattgtttg tattgctgga       480
atttgtgctg aggaacaacc ttttgctgag gctacttcag agccaggatt gactttcatt       540
gctgctaagt ttgatggaat tttgggaatg gctttccctg aaattgctgt tttgggagtt       600
acacctgttt tccacacttt tattgagcaa aagaaggttc catcaccagt ttttgctttt       660
tggttgaata gaaatcctga gtctgagatt ggaggagaaa ttacttttgg tggagttgat       720
actagaagat atgttgaacc tattacttgg acacctgtta caagaagagg ttattggcaa       780
ttcaaaatgg atatggttca aggtggatct tcttctattg cttgtcctaa cggttgtcaa       840
gctattgctg acactggaac ttccttgatt gctggtccaa aggctcaagt tgaagctatt       900
caaaagtata ttggtgctga gccattgatg aaaggtgaat acatgattcc atgtgataaa       960
gttccttctt tgccagacgt ttcctttatt attgacggaa aaactttac tttgaaagga      1020
gaggactacg ttttgactgt taaagctgct ggaaagtcta tttgtttgtc tggttttatg      1080
ggtatggatt ttccagaaaa gattggagaa ttgtggattt tgggagatgt tttcattggt      1140
aaatactata ctgtttttga tgttggtcaa gctagagttg gtttcgctca agctaaatct      1200
gaggatggtt tcccagttgg aactccagtt agaactttta gacaattgca agaagattct      1260
gattcagacg aagatgacgt ttttactttt                                       1290
```

<210> SEQ ID NO 10
<211> LENGTH: 429
<212> TYPE: PRT
<213> ORGANISM: Necator americanus

<400> SEQUENCE: 10

```
Ser Val His Arg Arg Leu Phe His Gln Ala Arg Arg His Val Thr Ser
1               5                   10                  15
Val Ser Leu Ser Arg Gln Pro Thr Leu Arg Glu Arg Leu Ile Ala Ser
            20                  25                  30
Gly Ser Trp Glu Asp Tyr Gln Lys Gln Arg Tyr His Tyr Arg Lys Lys
        35                  40                  45
Ile Leu Ala Lys Tyr Ala Ala Asn Lys Ala Ser Lys Leu Gln Ser Ala
    50                  55                  60
Asn Glu Ile Asp Glu Leu Leu Arg Asn Tyr Met Asp Ala Gln Tyr Tyr
65                  70                  75                  80
Gly Val Ile Gln Ile Gly Thr Pro Ala Gln Asn Phe Thr Val Ile Phe
                85                  90                  95
Asp Thr Gly Ser Ser Asn Leu Trp Val Pro Ser Arg Lys Cys Pro Phe
            100                 105                 110
Tyr Asp Ile Ala Cys Met Leu His His Arg Tyr Asp Ser Gly Ala Ser
        115                 120                 125
Ser Thr Tyr Lys Glu Asp Gly Arg Lys Met Ala Ile Gln Tyr Gly Thr
    130                 135                 140
```

Gly Ser Met Lys Gly Phe Ile Ser Lys Asp Ile Val Cys Ile Ala Gly
145                 150                 155                 160

Ile Cys Ala Glu Glu Gln Pro Phe Ala Glu Ala Thr Ser Glu Pro Gly
            165                 170                 175

Leu Thr Phe Ile Ala Ala Lys Phe Asp Gly Ile Leu Gly Met Ala Phe
        180                 185                 190

Pro Glu Ile Ala Val Leu Gly Val Thr Pro Val Phe His Thr Phe Ile
    195                 200                 205

Glu Gln Lys Lys Val Pro Ser Pro Val Phe Ala Phe Trp Leu Asn Arg
210                 215                 220

Asn Pro Glu Ser Glu Ile Gly Gly Glu Ile Thr Phe Gly Gly Val Asp
225                 230                 235                 240

Thr Arg Arg Tyr Val Glu Pro Ile Thr Trp Thr Pro Val Thr Arg Arg
                245                 250                 255

Gly Tyr Trp Gln Phe Lys Met Asp Met Val Gln Gly Gly Ser Ser Ser
            260                 265                 270

Ile Ala Cys Pro Asn Gly Cys Gln Ala Ile Ala Asp Thr Gly Thr Ser
        275                 280                 285

Leu Ile Ala Gly Pro Lys Ala Gln Val Glu Ala Ile Gln Lys Tyr Ile
    290                 295                 300

Gly Ala Glu Pro Leu Met Lys Gly Glu Tyr Met Ile Pro Cys Asp Lys
305                 310                 315                 320

Val Pro Ser Leu Pro Asp Val Ser Phe Ile Ile Asp Gly Lys Thr Phe
                325                 330                 335

Thr Leu Lys Gly Glu Asp Tyr Val Leu Thr Val Lys Ala Ala Gly Lys
            340                 345                 350

Ser Ile Cys Leu Ser Gly Phe Met Gly Met Asp Phe Pro Glu Lys Ile
        355                 360                 365

Gly Glu Leu Trp Ile Leu Gly Asp Val Phe Ile Gly Lys Tyr Tyr Thr
    370                 375                 380

Val Phe Asp Val Gly Gln Ala Arg Val Gly Phe Ala Gln Ala Lys Ser
385                 390                 395                 400

Glu Asp Gly Phe Pro Val Gly Thr Pro Val Arg Thr Phe Arg Gln Leu
                405                 410                 415

Gln Glu Asp Ser Asp Ser Asp Glu Asp Asp Val Phe Thr
            420                 425

<210> SEQ ID NO 11
<211> LENGTH: 1290
<212> TYPE: DNA
<213> ORGANISM: Necator americanus

<400> SEQUENCE: 11
tctgttcaca gaagattgtt tcatcaagct agaagacacg ttacttcagt ttccttgtcc    60
agacaaccaa ctttgagaga gagattgatt gcttcaggtt catgggaaga ctaccaaaaa   120
caaagatatc attacagaaa gaagattttg gctaagtacg ctgctaataa ggcttctaag   180
ttgcaatctg ctaacgagat tgatgaattg ttgagaaatt atatgatgc tcaatattat    240 ggagttattc aaattggaac accagctcaa aatttactg ttattttcgc cactggatcc    300
tcaaacttgt gggttccttc aagaaaatgt cctttctatg acattgcttg tatgttgcac   360
cacagatacg actctggagc ttcctccaca tacaagaag atggaagaaa gatggctatt    420
caatatggta caggatccat gaaaggtttc atttccaaag acattgtttg tattgctgga   480
atttgtgctg aggaacaacc ttttgctgag gctacttcag agccaggatt gactttcatt   540

```
gctgctaagt tgatggaat tttgggaatg gctttccctg aaattgctgt tttgggagtt    600
acacctgttt tccacacttt tattgagcaa aagaaggttc catcaccagt ttttgctttt    660
tggttgaata gaaatcctga gtctgagatt ggaggagaaa ttacttttgg tggagttgat    720
actagaagat atgttgaacc tattacttgg acacctgtta caagaagagg ttattggcaa    780
ttcaaaatgg atatggttca aggtggatct tcttctattg cttgtcctaa cggttgtcaa    840
gctattgctg acactggaac ttccttgatt gctggtccaa aggctcaagt tgaagctatt    900
caaaagtata ttggtgctga gccattgatg aaaggtgaat acatgattcc atgtgataaa    960
gttccttctt tgccagacgt ttcctttatt attgacggaa aaacttttac tttgaaagga   1020
gaggactacg ttttgactgt taaagctgct ggaaagtcta tttgtttgtc tggttttatg   1080
ggtatggatt ttccagaaaa gattggagaa ttgtggattt gggagatgt tttcattggt    1140 aaatactata ctgttttga tgttggtcaa gctagagttg gtttcgctca agctaaatct    1200
gaggatggtt tcccagttgg aactccagtt agaacttta gacaattgca agaagattct    1260
gattcagacg aagatgacgt tttacttttt                                    1290

<210> SEQ ID NO 12
<211> LENGTH: 428
<212> TYPE: PRT
<213> ORGANISM: Necator americanus

<400> SEQUENCE: 12

Ser Val His Arg Arg Leu Phe His Gln Ala Arg Arg His Val Thr Ser
1               5                   10                  15

Val Ser Leu Ser Arg Gln Pro Thr Leu Arg Glu Arg Leu Ile Ala Ser
            20                  25                  30

Gly Ser Trp Glu Asp Tyr Gln Lys Gln Arg Tyr His Tyr Arg Lys Lys
        35                  40                  45

Ile Leu Ala Lys Tyr Ala Ala Asn Lys Ala Ser Lys Leu Gln Ser Ala
    50                  55                  60

Asn Glu Ile Asp Glu Leu Leu Arg Asn Tyr Met Asp Ala Gln Tyr Tyr
65                  70                  75                  80

Gly Val Ile Gln Ile Gly Thr Pro Ala Gln Asn Phe Thr Val Ile Phe
                85                  90                  95

Ala Thr Gly Ser Ser Asn Leu Trp Val Pro Ser Arg Lys Cys Pro Phe
            100                 105                 110

Tyr Asp Ile Ala Cys Leu His His Arg Tyr Asp Ser Gly Ala Ser Ser
        115                 120                 125

Thr Tyr Lys Glu Asp Gly Arg Lys Met Ala Ile Gln Tyr Gly Thr Gly
    130                 135                 140

Ser Met Lys Gly Phe Ile Ser Lys Asp Ile Val Cys Ile Ala Gly Ile
145                 150                 155                 160

Cys Ala Glu Glu Gln Pro Phe Ala Glu Ala Thr Ser Glu Pro Gly Leu
                165                 170                 175

Thr Phe Ile Ala Ala Lys Phe Asp Gly Ile Leu Gly Met Ala Phe Pro
            180                 185                 190

Glu Ile Ala Val Leu Gly Val Thr Pro Val Phe His Thr Phe Ile Glu
        195                 200                 205

Gln Lys Lys Val Pro Ser Pro Val Phe Ala Phe Trp Leu Asn Arg Asn
    210                 215                 220

Pro Glu Ser Glu Ile Gly Gly Glu Ile Thr Phe Gly Gly Val Asp Thr
225                 230                 235                 240
```

```
Arg Arg Tyr Val Glu Pro Ile Thr Trp Thr Pro Val Thr Arg Arg Gly
                245                 250                 255

Tyr Trp Gln Phe Lys Met Asp Met Val Gln Gly Gly Ser Ser Ile
            260                 265                 270

Ala Cys Pro Asn Gly Cys Gln Ala Ile Ala Asp Thr Gly Thr Ser Leu
        275                 280                 285

Ile Ala Gly Pro Lys Ala Gln Val Glu Ala Ile Gln Lys Tyr Ile Gly
        290                 295                 300

Ala Glu Pro Leu Met Lys Gly Glu Tyr Met Ile Pro Cys Asp Lys Val
305                 310                 315                 320

Pro Ser Leu Pro Asp Val Ser Phe Ile Ile Asp Gly Lys Thr Phe Thr
                325                 330                 335

Leu Lys Gly Glu Asp Tyr Val Leu Thr Val Lys Ala Ala Gly Lys Ser
                340                 345                 350

Ile Cys Leu Ser Gly Phe Met Gly Met Asp Phe Pro Glu Lys Ile Gly
            355                 360                 365

Glu Leu Trp Ile Leu Gly Asp Val Phe Ile Gly Lys Tyr Tyr Thr Val
            370                 375                 380

Phe Asp Val Gly Gln Ala Arg Val Gly Phe Ala Gln Ala Lys Ser Glu
385                 390                 395                 400

Asp Gly Phe Pro Val Gly Thr Pro Val Arg Thr Phe Arg Gln Leu Gln
                405                 410                 415

Glu Asp Ser Asp Ser Asp Glu Asp Val Phe Thr
                420                 425

<210> SEQ ID NO 13
<211> LENGTH: 1290
<212> TYPE: DNA
<213> ORGANISM: Necator americanus

<400> SEQUENCE: 13
tctgttcaca gaagattgtt tcatcaagct agaagacacg ttacttcagt ttccttgtcc      60
agacaaccaa cttttgagaga gagattgatt gcttcaggtt catgggaaga ctaccaaaaa    120
caaagatatc attacagaaa gaagattttg gctaagtacg ctgctaataa ggcttctaag     180
ttgcaatctg ctaacgagat tgatgaattg ttgagaaatt atatggatgc tcaatattat     240
ggagttattc aaaattggaa ccagctcaa aattttactg ttattttcga cactggatcc     300
tcaaacttgt gggttccttc aagaaaatgt cctttctatg acattgcttg tatgttgcac    360
cacagatacg actctggagc ttcctccaca tacaaagaag atggaagaaa gatggctatt    420
caatatggta caggatccat gaaaggtttc atttccaaag acattgtttg tattgctgga    480
atttgtgctg aggaacaacc ttttgctgag gctacttcag agccaggatt gactttcatt    540
gctgctaagt tgatggaat tttgggaatg gctttccctg aaattgctgt tttgggagtt    600
acacctgttt tccacacttt tattgagcaa aagaaggttc catcaccagt ttttgctttt    660
tggttgaata gaaatcctga gtctgagatt ggaggagaaa ttacttttgg tggagttgat    720
actagaagat atgttgaacc tattacttgg acacctgtta caagaagagg ttattggcaa    780
ttcaaaatgg atatggttca aggtggatct tcttctattg cttgtcctaa cggttgtcaa    840
gctattgctg ccactggaac ttccttgatt gctggtccaa aggctcaagt tgaagctatt    900
caaaagtata ttggtgctga gccattgatg aaaggtgaat acatgattcc atgtgataaa    960
gttccttctt tgccagacgt ttccttatt attgacggaa aaacttttac ttgaaagga    1020 gaggactacg ttttgactgt taagctgct ggaaagtcta tttgtttgtc tggttttatg    1080
```

```
ggtatggatt ttccagaaaa gattggagaa ttgtggattt tgggagatgt tttcattggt   1140
aaatactata ctgtttttga tgttggtcaa gctagagttg gtttcgctca agctaaatct   1200
gaggatggtt tcccagttgg aactccagtt agaacttta gacaattgca agaagattct   1260
gattcagacg aagatgacgt ttttactttt                                    1290

<210> SEQ ID NO 14
<211> LENGTH: 429
<212> TYPE: PRT
<213> ORGANISM: Necator americanus

<400> SEQUENCE: 14

Ser Val His Arg Arg Leu Phe His Gln Ala Arg His Val Thr Ser
1               5                   10                  15

Val Ser Leu Ser Arg Gln Pro Thr Leu Arg Glu Arg Leu Ile Ala Ser
            20                  25                  30

Gly Ser Trp Glu Asp Tyr Gln Lys Gln Arg Tyr His Tyr Arg Lys Lys
        35                  40                  45

Ile Leu Ala Lys Tyr Ala Ala Asn Lys Ala Ser Lys Leu Gln Ser Ala
    50                  55                  60

Asn Glu Ile Asp Glu Leu Leu Arg Asn Tyr Met Asp Ala Gln Tyr Tyr
65                  70                  75                  80

Gly Val Ile Gln Ile Gly Thr Pro Ala Gln Asn Phe Thr Val Ile Phe
                85                  90                  95

Asp Thr Gly Ser Ser Asn Leu Trp Val Pro Ser Arg Lys Cys Pro Phe
            100                 105                 110

Tyr Asp Ile Ala Cys Met Leu His His Arg Tyr Asp Ser Gly Ala Ser
        115                 120                 125

Ser Thr Tyr Lys Glu Asp Gly Arg Lys Met Ala Ile Gln Tyr Gly Thr
    130                 135                 140

Gly Ser Met Lys Gly Phe Ile Ser Lys Asp Ile Val Cys Ile Ala Gly
145                 150                 155                 160

Ile Cys Ala Glu Glu Gln Pro Phe Ala Glu Ala Thr Ser Glu Pro Gly
                165                 170                 175

Leu Thr Phe Ile Ala Ala Lys Phe Asp Gly Ile Leu Gly Met Ala Phe
            180                 185                 190

Pro Glu Ile Ala Val Leu Gly Val Thr Pro Val Phe His Thr Phe Ile
        195                 200                 205

Glu Gln Lys Lys Val Pro Ser Pro Val Phe Ala Phe Trp Leu Asn Arg
    210                 215                 220

Asn Pro Glu Ser Glu Ile Gly Gly Glu Ile Thr Phe Gly Gly Val Asp
225                 230                 235                 240

Thr Arg Arg Tyr Val Glu Pro Ile Thr Trp Thr Pro Val Thr Arg Arg
                245                 250                 255

Gly Tyr Trp Gln Phe Lys Met Asp Met Val Gln Gly Gly Ser Ser Ser
            260                 265                 270

Ile Ala Cys Pro Asn Gly Cys Gln Ala Ile Ala Ala Thr Gly Thr Ser
        275                 280                 285

Leu Ile Ala Gly Pro Lys Ala Gln Val Glu Ala Ile Gln Lys Tyr Ile
    290                 295                 300

Gly Ala Glu Pro Leu Met Lys Gly Glu Tyr Met Ile Pro Cys Asp Lys
305                 310                 315                 320

Val Pro Ser Leu Pro Asp Val Ser Phe Ile Ile Asp Gly Lys Thr Phe
                325                 330                 335

Thr Leu Lys Gly Glu Asp Tyr Val Leu Thr Val Lys Ala Ala Gly Lys
```

```
              340             345             350
Ser Ile Cys Leu Ser Gly Phe Met Gly Met Asp Phe Pro Glu Lys Ile
            355                 360                 365

Gly Glu Leu Trp Ile Leu Gly Asp Val Phe Ile Gly Lys Tyr Tyr Thr
            370                 375                 380

Val Phe Asp Val Gly Gln Ala Arg Val Gly Phe Ala Gln Ala Lys Ser
385                 390                 395                 400

Glu Asp Gly Phe Pro Val Gly Thr Pro Val Arg Thr Phe Arg Gln Leu
                405                 410                 415

Gln Glu Asp Ser Asp Ser Asp Glu Asp Asp Val Phe Thr
            420                 425
```

<210> SEQ ID NO 15
<211> LENGTH: 1290
<212> TYPE: DNA
<213> ORGANISM: Necator americanus

<400> SEQUENCE: 15

```
tctgttcaca gaagattgtt tcatcaagct agaagacacg ttacttcagt ttccttgtcc      60
agacaaccaa ctttgagaga gagattgatt gcttcaggtt catgggaaga ctaccaaaaa     120
caaagatatc attacagaaa gaagattttg gctaagtacg ctgctaataa ggcttctaag     180
ttgcaatctg ctaacgagat tgatgaattg ttgagaaatt atatggatgc tcaatattat     240
ggagttattc aaattggaac accagctcaa aattttactg ttattttcgc cactggatcc     300
tcaaacttgt gggttccttc aagaaaatgt cctttctatg acattgcttg tatgttgcac     360
cacagatacg actctggagc ttcctccaca tacaaagaag atggaagaaa gatggctatt     420
caatatggta caggatccat gaaaggtttc atttccaaag acattgtttg tattgctgga     480
atttgtgctg aggaacaacc ttttgctgag gctacttcag agccaggatt gactttcatt     540
gctgctaagt ttgatggaat tttgggaatg gcttttccctg aaattgctgt tttgggagtt     600
acacctgttt tccacacttt tattgagcaa aagaaggttc atcaccagt ttttgctttt     660
tggttgaata gaaatcctga gtctgagatt ggaggagaaa ttactttttgg tggagttgat     720
actagaagat atgttgaacc tattacttgg acacctgtta caagaagagg ttattggcaa     780
ttcaaaatgg atatggttca aggtggatct tcttctattg cttgtcctaa cggttgtcaa     840
gctattgctg ccactggaac ttccttgatt gctggtccaa aggctcaagt tgaagctatt     900
caaaagtata ttggtgctga gccattgatg aaaggtgaat acatgattcc atgtgataaa     960
gttccttctt tgccagacgt ttcctttatt attgacggaa aaactttta ctttgaaagga    1020
gaggactacg ttttgactgt taaagctgct ggaaagtcta tttgtttgtc tggttttatg    1080
ggtatggatt tccagaaaaa gattggagaa ttgtggattt gggagatgt tttcattggt    1140
aaatactata ctgttttttga tgttggtcaa gctagagttg gtttcgctca agctaaatct    1200
gaggatggtt tcccagttgg aactccagtt agaactttta gacaattgca agaagattct    1260
gattcagacg aagatgacgt ttttactttt                                       1290
```

<210> SEQ ID NO 16
<211> LENGTH: 429
<212> TYPE: PRT
<213> ORGANISM: Necator americanus

<400> SEQUENCE: 16

```
Ser Val His Arg Arg Leu Phe His Gln Ala Arg Arg His Val Thr Ser
1               5                   10                  15
```

Val Ser Leu Ser Arg Gln Pro Thr Leu Arg Glu Arg Leu Ile Ala Ser
         20                  25                  30

Gly Ser Trp Glu Asp Tyr Gln Lys Gln Arg Tyr His Tyr Arg Lys Lys
             35                  40                  45

Ile Leu Ala Lys Tyr Ala Ala Asn Lys Ala Ser Lys Leu Gln Ser Ala
 50                  55                  60

Asn Glu Ile Asp Glu Leu Leu Arg Asn Tyr Met Asp Ala Gln Tyr Tyr
 65                  70                  75                  80

Gly Val Ile Gln Ile Gly Thr Pro Ala Gln Asn Phe Thr Val Ile Phe
                 85                  90                  95

Ala Thr Gly Ser Ser Asn Leu Trp Val Pro Ser Arg Lys Cys Pro Phe
                100                 105                 110

Tyr Asp Ile Ala Cys Met Leu His His Arg Tyr Asp Ser Gly Ala Ser
            115                 120                 125

Ser Thr Tyr Lys Glu Asp Gly Arg Lys Met Ala Ile Gln Tyr Gly Thr
        130                 135                 140

Gly Ser Met Lys Gly Phe Ile Ser Lys Asp Ile Val Cys Ile Ala Gly
145                 150                 155                 160

Ile Cys Ala Glu Glu Gln Pro Phe Ala Glu Ala Thr Ser Glu Pro Gly
                165                 170                 175

Leu Thr Phe Ile Ala Ala Lys Phe Asp Gly Ile Leu Gly Met Ala Phe
            180                 185                 190

Pro Glu Ile Ala Val Leu Gly Val Thr Pro Val Phe His Thr Phe Ile
        195                 200                 205

Glu Gln Lys Lys Val Pro Ser Pro Val Phe Ala Phe Trp Leu Asn Arg
    210                 215                 220

Asn Pro Glu Ser Glu Ile Gly Gly Ile Thr Phe Gly Gly Val Asp
225                 230                 235                 240

Thr Arg Arg Tyr Val Glu Pro Ile Thr Trp Thr Pro Val Thr Arg Arg
                245                 250                 255

Gly Tyr Trp Gln Phe Lys Met Asp Met Val Gln Gly Gly Ser Ser Ser
            260                 265                 270

Ile Ala Cys Pro Asn Gly Cys Gln Ala Ile Ala Ala Thr Gly Thr Ser
        275                 280                 285

Leu Ile Ala Gly Pro Lys Ala Gln Val Glu Ala Ile Gln Lys Tyr Ile
    290                 295                 300

Gly Ala Glu Pro Leu Met Lys Gly Glu Tyr Met Ile Pro Cys Asp Lys
305                 310                 315                 320

Val Pro Ser Leu Pro Asp Val Ser Phe Ile Ile Asp Gly Lys Thr Phe
                325                 330                 335

Thr Leu Lys Gly Glu Asp Tyr Val Leu Thr Val Lys Ala Ala Gly Lys
            340                 345                 350

Ser Ile Cys Leu Ser Gly Phe Met Gly Met Asp Phe Pro Glu Lys Ile
        355                 360                 365

Gly Glu Leu Trp Ile Leu Gly Asp Val Phe Ile Gly Lys Tyr Tyr Thr
    370                 375                 380

Val Phe Asp Val Gly Gln Ala Arg Val Gly Phe Ala Gln Ala Lys Ser
385                 390                 395                 400

Glu Asp Gly Phe Pro Val Gly Thr Pro Val Arg Thr Phe Arg Gln Leu
                405                 410                 415

Gln Glu Asp Ser Asp Ser Asp Glu Asp Val Phe Thr
            420                 425

<210> SEQ ID NO 17

```
<211> LENGTH: 789
<212> TYPE: DNA
<213> ORGANISM: Necator americanus

<400> SEQUENCE: 17
aagtgatggt tcattacaag ttaacctact tcgctatacg tggagccgga gaatgtgcaa        60
gacagatctt cgcacttgcc gatcaggaat tcgaggatgt ccgtttagac aaagagcagt       120
tcgcaaaagt gaagcctgat ttgcctttcg gacaggttcc agtccttgaa gtcgatggca       180
agcaactggc tcaatccctt gcgatttgcc gctatctggc caggcagttc ggtttcgcag       240
gcaaatcaac gttcgatgaa gccgtagtcg actctttagc agaccagtat tctgactatc       300
gcgtcgagat caagtcgttc ttctacactg tcattggaat gcgagaaggt gatgtggagc       360
aactcaaaaa agaagtgtta cttcctgctc gcgataaatt cttcggattc atcactaaat       420
tccttaagaa aagcccttct ggtttccttg tcggtgactc actgacgtgg gtggacctct       480
tggtctcgga gcacaatgct acaatgctta cgtttgtacc agagttcctt gaaggctatc       540
ctgaagtaaa agagcacatg gaaaagatac gagcgattcc gaaactgaag aaatggatcg       600
aaacccgacc agagacattg ttctaatttg tagtgatgtt atcctacttg ttctgatcta       660
tttgagttat cttcattgtc aacagaaatt cattattggc ttgcagtaat aaccgttatt       720
caggcacttg aaatccacta gttatttctt tccataagct acattctcag atgtatgtat       780
gaggataaa                                                                789

<210> SEQ ID NO 18
<211> LENGTH: 206
<212> TYPE: PRT
<213> ORGANISM: Necator americanus

<400> SEQUENCE: 18

Met Val His Tyr Lys Leu Thr Tyr Phe Ala Ile Arg Gly Ala Gly Glu
1               5                   10                  15

Cys Ala Arg Gln Ile Phe Ala Leu Ala Asp Gln Glu Phe Glu Asp Val
            20                  25                  30

Arg Leu Asp Lys Glu Gln Phe Ala Lys Val Lys Pro Asp Leu Pro Phe
        35                  40                  45

Gly Gln Val Pro Val Leu Glu Val Asp Gly Lys Gln Leu Ala Gln Ser
    50                  55                  60

Leu Ala Ile Cys Arg Tyr Leu Ala Arg Gln Phe Gly Phe Ala Gly Lys
65                  70                  75                  80

Ser Thr Phe Asp Glu Ala Val Val Asp Ser Leu Ala Asp Gln Tyr Ser
                85                  90                  95

Asp Tyr Arg Val Glu Ile Lys Ser Phe Phe Tyr Thr Val Ile Gly Met
            100                 105                 110

Arg Glu Gly Asp Val Glu Gln Leu Lys Lys Glu Val Leu Leu Pro Ala
        115                 120                 125

Arg Asp Lys Phe Phe Gly Phe Ile Thr Lys Phe Leu Lys Lys Ser Pro
    130                 135                 140

Ser Gly Phe Leu Val Gly Asp Ser Leu Thr Trp Val Asp Leu Leu Val
145                 150                 155                 160

Ser Glu His Asn Ala Thr Met Leu Thr Phe Val Pro Glu Phe Leu Glu
                165                 170                 175

Gly Tyr Pro Glu Val Lys Glu His Met Glu Lys Ile Arg Ala Ile Pro
            180                 185                 190

Lys Leu Lys Lys Trp Ile Glu Thr Arg Pro Glu Thr Leu Phe
        195                 200                 205
```

<210> SEQ ID NO 19
<211> LENGTH: 733
<212> TYPE: DNA
<213> ORGANISM: Necator americanus

<400> SEQUENCE: 19

```
gatggtccat tacaagctca cttacttcgc aggccgtgga cttgctgaac ctattcgcca      60
gattttcgcc cttgctggtc aaaaatatga agatgttcgt tataccttc aggaatggcc     120
caaacacaag gatgaaatgc catttggtca ataccagtg ttggaagagg atggtaaaca     180
actagcgcaa tcattcgcta tcgctcgtta cctttccaga aaattcggtt ttgccggaaa    240
aactcctttc gaagaagcct tagtcgactc ggttgctgac caatacaagg actacatcaa    300
tgagatccgt ccatacctca gggtcgttgc aggagtcgat cagggagatc cggagaagct    360
tttcaaggaa ctgctccttc cagctcgtga gaaattcttc ggtttcatga aaaaattcct    420
tgagaagagc aaatctggtt acctcgttgg tgattcggtg acatacgctg acttgtgctt    480
agccgagcac acatctggta tcgctgcgaa gttccccagt atctatgatg gtttccctga    540
gatcaaagct catgccgaaa aggttcgatc gataccggct ctgaaaaaat ggattgaaac    600
tcgacctgag actaaattct aatttttccc gagttgttta catatcagtt caagagggta    660
taaaataaag gtgttttct tttaaaaaaa aatggtcctt ctctcgattg cagcgtactt    720
caaagccggt tgt                                                       733
```

<210> SEQ ID NO 20
<211> LENGTH: 206
<212> TYPE: PRT
<213> ORGANISM: Necator americanus

<400> SEQUENCE: 20

```
Met Val His Tyr Lys Leu Thr Tyr Phe Ala Gly Arg Gly Leu Ala Glu
1               5                   10                  15

Pro Ile Arg Gln Ile Phe Ala Leu Ala Gly Gln Lys Tyr Glu Asp Val
            20                  25                  30

Arg Tyr Thr Phe Gln Glu Trp Pro Lys His Lys Asp Glu Met Pro Phe
        35                  40                  45

Gly Gln Ile Pro Val Leu Glu Glu Asp Gly Lys Gln Leu Ala Gln Ser
    50                  55                  60

Phe Ala Ile Ala Arg Tyr Leu Ser Arg Lys Phe Gly Phe Ala Gly Lys
65                  70                  75                  80

Thr Pro Phe Glu Glu Ala Leu Val Asp Ser Val Ala Asp Gln Tyr Lys
                85                  90                  95

Asp Tyr Ile Asn Glu Ile Arg Pro Tyr Leu Arg Val Val Ala Gly Val
            100                 105                 110

Asp Gln Gly Asp Pro Glu Lys Leu Phe Lys Glu Leu Leu Leu Pro Ala
        115                 120                 125

Arg Glu Lys Phe Phe Gly Phe Met Lys Lys Phe Leu Glu Lys Ser Lys
    130                 135                 140

Ser Gly Tyr Leu Val Gly Asp Ser Val Thr Tyr Ala Asp Leu Cys Leu
145                 150                 155                 160

Ala Glu His Thr Ser Gly Ile Ala Ala Lys Phe Pro Ser Ile Tyr Asp
                165                 170                 175

Gly Phe Pro Glu Ile Lys Ala His Ala Glu Lys Val Arg Ser Ile Pro
            180                 185                 190

Ala Leu Lys Lys Trp Ile Glu Thr Arg Pro Glu Thr Lys Phe
```

-continued

```
          195              200              205
```

<210> SEQ ID NO 21
<211> LENGTH: 724
<212> TYPE: DNA
<213> ORGANISM: Necator americanus

<400> SEQUENCE: 21

```
gaaaggttta attacccaag tttgagaatg gttcactaca agctaaccta cttcgacgga     60
cgcggtgccg ctgaaattat tcgtcagatt tttgtccttg ctggtcaaga atacgaggat    120
atccgtctta gtcacgacga atggcccaag tacaagaacg aaatgccatt cggtcaattg    180
ccagtgttgg aagtcgacgg caaaaagctt gcacaatctt tcgctatcgc ccgcttcgtg    240
gccaaaaaat tcgggtttgc tggaaagtgt ccgtttgaag aggctctggt tgactcgatc    300
accgatcaat acaaggactt catcaatgag atccgcccat tcttacgagt tgctatgggt    360
ttcgcagagg gagatctgga gaagctcagc aacgaagtct tcttgccagc tcgtgaaaag    420
ttcttcggat tcatgacaaa cttcctcaag gagagcaagt ctggttatct cgttggtgat    480
tcattgacgt tcgcagacct gtacctagct gaatgcgcat ctgaattcgc taagaaaact    540
ccgacaatct tcgacggatt cccagaaatc aaagcccatg ccgaaaaagt tcgctcgaac    600
ccagctctca gaaatggat tgaaacccga ccagaaacta aattctaaat cctcgcaact    660
acttggttat ttccatcgat tcccgtgaat aaaattattg ctctcaaaaa aaaaaaaaaa    720
aaaa                                                                 724
```

<210> SEQ ID NO 22
<211> LENGTH: 206
<212> TYPE: PRT
<213> ORGANISM: Necator americanus

<400> SEQUENCE: 22

Met Val His Tyr Lys Leu Thr Tyr Phe Asp Gly Arg Gly Ala Ala Glu
1               5                   10                  15

Ile Ile Arg Gln Ile Phe Val Leu Ala Gly Gln Glu Tyr Glu Asp Ile
            20                  25                  30

Arg Leu Ser His Asp Glu Trp Pro Lys Tyr Lys Asn Glu Met Pro Phe
        35                  40                  45

Gly Gln Leu Pro Val Leu Glu Val Asp Gly Lys Lys Leu Ala Gln Ser
    50                  55                  60

Phe Ala Ile Ala Arg Phe Val Ala Lys Lys Phe Gly Phe Ala Gly Lys
65                  70                  75                  80

Cys Pro Phe Glu Glu Ala Leu Val Asp Ser Ile Thr Asp Gln Tyr Lys
                85                  90                  95

Asp Phe Ile Asn Glu Ile Arg Pro Phe Leu Arg Val Ala Met Gly Phe
            100                 105                 110

Ala Glu Gly Asp Leu Glu Lys Leu Ser Asn Glu Val Phe Leu Pro Ala
        115                 120                 125

Arg Glu Lys Phe Phe Gly Phe Met Thr Asn Phe Leu Lys Glu Ser Lys
    130                 135                 140

Ser Gly Tyr Leu Val Gly Asp Ser Leu Thr Phe Ala Asp Leu Tyr Leu
145                 150                 155                 160

Ala Glu Cys Ala Ser Glu Phe Ala Lys Lys Thr Pro Thr Ile Phe Asp
                165                 170                 175

Gly Phe Pro Glu Ile Lys Ala His Ala Glu Lys Val Arg Ser Asn Pro
            180                 185                 190

```
Ala Leu Lys Lys Trp Ile Glu Thr Arg Pro Glu Thr Lys Phe
    195                 200                 205
```

<210> SEQ ID NO 23
<211> LENGTH: 1134
<212> TYPE: DNA
<213> ORGANISM: Necator americanus

<400> SEQUENCE: 23

```
gttaaagccg tgtaagcaac agggttctttt gtgatgttaa ctctcgctgc acttctgatt     60
tctgtttcgc tggttgagcc gacaggcata ggtgagtttc ttgctcaacc agcacctgca    120
tatgctagaa gactcacagg gcaggccctt gttgactacg tcaattcgca ccactcattg    180
tacaaggcca atattcacc agatgctcaa gaacgcatga atctagaat tatggatttg    240
agtttcatgg ttgatgcgga agtcatgatg gaagaaatgg accagcagga ggatatagat    300
ctcgctgttt ctttacctga agtttcgac gctcgtgaaa aatggccaga atgtccttca    360
ataggattaa tccgtgatca gtccgccggt ggaggatgtt gggcagtatc ctcagcagag    420
gtgatgaccg acaggatctg tatacaatca aatggaacaa agcaggtgta tgtttccgaa    480
acggatatct tatcatgctg tggacaacgt tgcggtagcg ggtgtacctc aggtgtgcca    540
cgtcaagctt tcaactatgc aattcgtaaa ggtgtttgca gtggaggacc atatggaacg    600
aagggtgttt gcaaacccta tcctttctat ccatgcggct atcatgctca tctgccatat    660
tatggaccat gtccagatgg tatgtggcct acgccaacat gcgaaaaggc atgtcaatcc    720
gactatactg ttccgtacaa cgatgacagg atcttcggca gcaaaactat tgtcttgacg    780
ggagaggaaa aaattaagcg agagattttc aataacggac cattggtagc cacgtataca    840
gtttacgaag atttcgctta ttacaagaat ggaatttaca tgactggtct cggtagagcg    900
acaggcgcac atgcagtcaa aattattggc tggggtgaag aaaatggagt caagtattgg    960
ttgattgcaa actcgtggaa cactgattgg ggagagaatg gcttcttccg catgcttcgt   1020
ggaacaaacc tttgcgatat tgaactaagc gcgactggag gaacgttcaa ggtgtgaacg   1080
tgatcgaaaa gaacgatttt gaacaaaaat cttcccgtat tgtcatcaaa aaaa          1134
```

<210> SEQ ID NO 24
<211> LENGTH: 347
<212> TYPE: PRT
<213> ORGANISM: Necator americanus

<400> SEQUENCE: 24

```
Met Leu Thr Leu Ala Ala Leu Leu Ile Ser Val Ser Leu Val Glu Pro
1               5                   10                  15

Thr Gly Ile Gly Glu Phe Leu Ala Gln Pro Ala Pro Ala Tyr Ala Arg
            20                  25                  30

Arg Leu Thr Gly Gln Ala Leu Val Asp Tyr Val Asn Ser His His Ser
        35                  40                  45

Leu Tyr Lys Ala Lys Tyr Ser Pro Asp Ala Gln Glu Arg Met Lys Ser
    50                  55                  60

Arg Ile Met Asp Leu Ser Phe Met Val Asp Ala Glu Val Met Met Glu
65                  70                  75                  80

Glu Met Asp Gln Gln Glu Asp Ile Asp Leu Ala Val Ser Leu Pro Glu
                85                  90                  95

Ser Phe Asp Ala Arg Glu Lys Trp Pro Glu Cys Pro Ser Ile Gly Leu
            100                 105                 110

Ile Arg Asp Gln Ser Ala Gly Gly Gly Cys Trp Ala Val Ser Ser Ala
        115                 120                 125
```

```
Glu Val Met Thr Asp Arg Ile Cys Ile Gln Ser Asn Gly Thr Lys Gln
    130                 135                 140
Val Tyr Val Ser Glu Thr Asp Ile Leu Ser Cys Cys Gly Gln Arg Cys
145                 150                 155                 160
Gly Ser Gly Cys Thr Ser Gly Val Pro Arg Gln Ala Phe Asn Tyr Ala
                165                 170                 175
Ile Arg Lys Gly Val Cys Ser Gly Gly Pro Tyr Gly Thr Lys Gly Val
            180                 185                 190
Cys Lys Pro Tyr Pro Phe Tyr Pro Cys Gly Tyr His Ala His Leu Pro
        195                 200                 205
Tyr Tyr Gly Pro Cys Pro Asp Gly Met Trp Pro Thr Pro Thr Cys Glu
    210                 215                 220
Lys Ala Cys Gln Ser Asp Tyr Thr Val Pro Tyr Asn Asp Asp Arg Ile
225                 230                 235                 240
Phe Gly Ser Lys Thr Ile Val Leu Thr Gly Glu Glu Lys Ile Lys Arg
                245                 250                 255
Glu Ile Phe Asn Asn Gly Pro Leu Val Ala Thr Tyr Thr Val Tyr Glu
            260                 265                 270
Asp Phe Ala Tyr Tyr Lys Asn Gly Ile Tyr Met Thr Gly Leu Gly Arg
        275                 280                 285
Ala Thr Gly Ala His Ala Val Lys Ile Ile Gly Trp Gly Glu Glu Asn
    290                 295                 300
Gly Val Lys Tyr Trp Leu Ile Ala Asn Ser Trp Asn Thr Asp Trp Gly
305                 310                 315                 320
Glu Asn Gly Phe Phe Arg Met Leu Arg Gly Thr Asn Leu Cys Asp Ile
                325                 330                 335
Glu Leu Ser Ala Thr Gly Gly Thr Phe Lys Val
            340                 345

<210> SEQ ID NO 25
<211> LENGTH: 1177
<212> TYPE: DNA
<213> ORGANISM: Necator americanus

<400> SEQUENCE: 25
ttaattctta ttgctctggt ggtgacggcg ttggctcaac agccgctttc actaaaggag     60
tatctggaac agccgatacc agaggaggca gagaatcttt ccggagaagc gtttgcggag    120
tttctgaaca acgacaatc gttttttcacg gctaagtaca cgccaaatgc tttaaacatt    180
cttaaaatgc gtgtgatgga atcgagattc ctggacaatg aagaaggtga atgctaaaa    240
gaggaggaca tggatttcag tgaagaaatt cctgttagtt ttgatgctcg agacaaatgg    300
cccaaatgca cctccatagg atttatccgt gatcaatcac actgtggttc atgctgggca    360
gtatcgtcag cagaaacgat gtcagatcga ctctgcgtgc aatcaaacgg tacaattaag    420
gtacttctat ccgatacgga catccttgcc tgttgcccga attgtggtgc tggatgtgga    480
ggaggccaca caattcgagc gtgggaatat tttaagaaca caggcgtttg cactggcgga    540
ctatatggaa caaaggattc ctgcaaacca tacgctttct atccatgtaa agacgaaagt    600
tacggaaagt gccccaagga ttcttttcca acaccaaaat gtcgaaaaat tgtcagtat    660
aaatacagta agagtacgc cgacgacaaa tactacgcga attccgcata tcgaattcca    720
cagaatgaga cgtggatcaa attggagatc atgagaaacg ggcctgtgac agcatcattc    780
aggatttatc cggattttgg ttttacgaa aaggagtttt atgtgacttc aggcggaagg    840
gaactaggtg ggcacgcgat taaaatcatt ggatgggaa cggaaaaagt aaacggaact    900
```

```
gacctacctt actggttgat tgctaactct tggggtactg actggggaga gaataacggc    960
tatttccgca tacttcgcgg acaaaatcac tgccaaatag aacagaaagt tatcgccggt   1020
atgataaaag taccacaacc gaaatccgcc ggtccaccac ttcaacccaa tccttcaagc   1080
tgaaccaagt tgtagtattg tccccatcaa tccaagcatt tcttggggtg atacttttac   1140
gaataaaaac tacattataa aaaaaaaaaa aaaaaa                             1177
```

<210> SEQ ID NO 26
<211> LENGTH: 360
<212> TYPE: PRT
<213> ORGANISM: Necator americanus

<400> SEQUENCE: 26

```
Leu Ile Leu Ile Ala Leu Val Val Thr Ala Leu Ala Gln Gln Pro Leu
1               5                   10                  15

Ser Leu Lys Glu Tyr Leu Glu Gln Pro Ile Pro Glu Glu Ala Glu Asn
            20                  25                  30

Leu Ser Gly Glu Ala Phe Ala Glu Phe Leu Asn Lys Arg Gln Ser Phe
        35                  40                  45

Phe Thr Ala Lys Tyr Thr Pro Asn Ala Leu Asn Ile Leu Lys Met Arg
    50                  55                  60

Val Met Glu Ser Arg Phe Leu Asp Asn Glu Glu Gly Glu Met Leu Lys
65                  70                  75                  80

Glu Glu Asp Met Asp Phe Ser Glu Glu Ile Pro Val Ser Phe Asp Ala
                85                  90                  95

Arg Asp Lys Trp Pro Lys Cys Thr Ser Ile Gly Phe Ile Arg Asp Gln
            100                 105                 110

Ser His Cys Gly Ser Cys Trp Ala Val Ser Ser Ala Glu Thr Met Ser
        115                 120                 125

Asp Arg Leu Cys Val Gln Ser Asn Gly Thr Ile Lys Val Leu Leu Ser
    130                 135                 140

Asp Thr Asp Ile Leu Ala Cys Cys Pro Asn Cys Gly Ala Gly Cys Gly
145                 150                 155                 160

Gly Gly His Thr Ile Arg Ala Trp Glu Tyr Phe Lys Asn Thr Gly Val
                165                 170                 175

Cys Thr Gly Gly Leu Tyr Gly Thr Lys Asp Ser Cys Lys Pro Tyr Ala
            180                 185                 190

Phe Tyr Pro Cys Lys Asp Glu Ser Tyr Gly Lys Cys Pro Lys Asp Ser
        195                 200                 205

Phe Pro Thr Pro Lys Cys Arg Lys Ile Cys Gln Tyr Lys Tyr Ser Lys
    210                 215                 220

Lys Tyr Ala Asp Asp Lys Tyr Tyr Ala Asn Ser Ala Tyr Arg Ile Pro
225                 230                 235                 240

Gln Asn Glu Thr Trp Ile Lys Leu Glu Ile Met Arg Asn Gly Pro Val
                245                 250                 255

Thr Ala Ser Phe Arg Ile Tyr Pro Asp Phe Gly Phe Tyr Glu Lys Gly
            260                 265                 270

Val Tyr Val Thr Ser Gly Gly Arg Glu Leu Gly Gly His Ala Ile Lys
        275                 280                 285

Ile Ile Gly Trp Gly Thr Glu Lys Val Asn Gly Thr Asp Leu Pro Tyr
    290                 295                 300

Trp Leu Ile Ala Asn Ser Trp Gly Thr Asp Trp Gly Glu Asn Gly
305                 310                 315                 320

Tyr Phe Arg Ile Leu Arg Gly Gln Asn His Cys Gln Ile Glu Gln Lys
```

```
                    325                 330                 335
Val Ile Ala Gly Met Ile Lys Val Pro Gln Pro Lys Ser Ala Gly Pro
        340                 345                 350

Pro Leu Gln Pro Asn Pro Ser Ser
        355                 360
```

<210> SEQ ID NO 27
<211> LENGTH: 1181
<212> TYPE: DNA
<213> ORGANISM: Necator americanus

<400> SEQUENCE: 27

```
tcgttgaggc gttatttcaa gcttctctcg cctcgatttc agattctcca attgtttcag      60
tgaatcgtgg aacagtcaat ctcactttg tgagatccaa tgaaagctaa ttttgcgttg     120
gtcgtcgtcc ttctggcaat aaaccagtta tatgcagatg agctgcttca caacaagag     180
tccgaacacg gacttagtgg ccaagcgctc gttgactacg ttaattcgca ccaatcactt     240
ttcaaaacag aatattcgcc aaccaatgaa caattcgtta aagcccgtat aatggacata     300
aagtatatga ctgaggctag ccacaaatat ccaagaaagg cattaatct gaacgttgaa      360
ctccctgaaa ggtttgacgc acgtgaaaaa tggccacatt gcgcctccat cggtctcatt     420
cgcgatcact ctgcttgcgg atcgtgttgg gctgtatcgg cagcgtcggt tatgtcagat     480
cgactctgta tccagacgaa cggcacaaac cagaagatcc tttcgtcggc ggacatcctt     540
gcgtgttgtg gagaagactg tggctcagga tgcgaaggcg ttatccgat tcaggcgtac       600
ttctacctgg aaaatactgg agtatgtagt ggaggagagt atcgagaaaa gaatgtatgc     660
aaaccatatc ccttttatcc gtgtgacgga aactatggac catgcccccaa ggagggtgcg    720
ttcgacactc caaagtgtcg gaaaatatgt cagttccgat atcctgttcc atacgaagaa     780
gataaagtgt ttggaaaaaa ttcacacatc cttctgcaag acaacgaggc aagaatcaga    840
caggaaattt tcataaacgg accagtggga gctaatttt acgttttcga agactttata     900
cactacaagg aagggatta taagcagaca tatgggaaat ggataggagt acatgcaatc     960
aaacttattg gttgggcac agaaaatgga acagattatt ggttggttgc taactcgtac    1020
aactacgact ggggagagaa tggcaccttc cgcattcttc gtggaactaa tcactgtttg     1080
atagaatcac aagtgatcgc aacggagatg attgtatgaa tgtctaatga acgattggtc     1140
gcatgccgat ctctgaagta aaatgtgtta atcaaaaaaa a                         1181
```

<210> SEQ ID NO 28
<211> LENGTH: 339
<212> TYPE: PRT
<213> ORGANISM: Necator americanus

<400> SEQUENCE: 28

```
Met Lys Ala Asn Phe Ala Leu Val Val Leu Leu Ala Ile Asn Gln
1               5                   10                  15

Leu Tyr Ala Asp Glu Leu Leu His Lys Gln Glu Ser Glu His Gly Leu
            20                  25                  30

Ser Gly Gln Ala Leu Val Asp Tyr Val Asn Ser His Gln Ser Leu Phe
        35                  40                  45

Lys Thr Glu Tyr Ser Pro Thr Asn Glu Gln Phe Val Lys Ala Arg Ile
    50                  55                  60

Met Asp Ile Lys Tyr Met Thr Glu Ala Ser His Lys Tyr Pro Arg Lys
65                  70                  75                  80

Gly Ile Asn Leu Asn Val Glu Leu Pro Glu Arg Phe Asp Ala Arg Glu
```

```
                    85                  90                  95
Lys Trp Pro His Cys Ala Ser Ile Gly Leu Ile Arg Asp His Ser Ala
            100                 105                 110

Cys Gly Ser Cys Trp Ala Val Ser Ala Ala Ser Val Met Ser Asp Arg
        115                 120                 125

Leu Cys Ile Gln Thr Asn Gly Thr Asn Gln Lys Ile Leu Ser Ser Ala
    130                 135                 140

Asp Ile Leu Ala Cys Cys Gly Glu Asp Cys Ser Gly Cys Glu Gly Gly
145                 150                 155                 160

Gly Tyr Pro Ile Gln Ala Tyr Phe Tyr Leu Glu Asn Thr Gly Val Cys
                165                 170                 175

Ser Gly Gly Glu Tyr Arg Glu Lys Asn Val Cys Lys Pro Tyr Pro Phe
            180                 185                 190

Tyr Pro Cys Asp Gly Asn Tyr Gly Pro Cys Pro Lys Glu Gly Ala Phe
        195                 200                 205

Asp Thr Pro Lys Cys Arg Lys Ile Cys Gln Phe Arg Tyr Pro Val Pro
    210                 215                 220

Tyr Glu Glu Asp Lys Val Phe Gly Lys Asn Ser His Ile Leu Leu Gln
225                 230                 235                 240

Asp Asn Glu Ala Arg Ile Arg Gln Glu Ile Phe Ile Asn Gly Pro Val
                245                 250                 255

Gly Ala Asn Phe Tyr Val Phe Glu Asp Phe Ile His Tyr Lys Glu Gly
            260                 265                 270

Ile Tyr Lys Gln Thr Tyr Gly Lys Trp Ile Gly Val His Ala Ile Lys
        275                 280                 285

Leu Ile Gly Trp Gly Thr Glu Asn Gly Thr Asp Tyr Trp Leu Val Ala
    290                 295                 300

Asn Ser Tyr Asn Tyr Asp Trp Gly Glu Asn Gly Thr Phe Arg Ile Leu
305                 310                 315                 320

Arg Gly Thr Asn His Cys Leu Ile Glu Ser Gln Val Ile Ala Thr Glu
                325                 330                 335

Met Ile Val

<210> SEQ ID NO 29
<211> LENGTH: 1236
<212> TYPE: DNA
<213> ORGANISM: Necator americanus

<400> SEQUENCE: 29
tagataataa tcttttgca cgtcagagaa tttctttgat aaaaccacaa ttaaacaatc     60
tcagcgctgt aaacacgtgc aaaactactc gttcatttct cttcactttc cctccaaaac    120
caaacattca agagaagcat gataaccatc attaccctat tgcttatcgc ttctacagtg    180
aagtcactaa cagtggagga gtacttggcc cgaccagtgc cggaatatgc cacaaaactg    240
acaggacaag cctacgttga ctatgttaat cagcatcaat cattctacaa ggctgaatat    300
tccccgctgg ttgaacagta tgccaaagct gtgatgagat ctgagtttat gacgaagccg    360
aaccaaaatt atgtggtgaa ggacgtagat ctaaacatca atcttccaga aaccttcgac    420
gcaagggaaa aatggccaaa ctgcacatca ataaggacaa ttcgcgatca gtccaattgt    480
ggatcatgtt gggcagtatc agcggcgtcg gtaatgtcag atcgtttatg catacagtcg    540
aacggcacaa tacagtcatg ggcttctgat acggatattc tatcatgttg ctggaattgc    600
ggaatgggat gcgatggagg tagaccgttt gcggcgttct ttttcgcgat agacaatggt    660
gtatgcactg gaggaccttt cagagagcca aacgtgtgca aaccatacgc tttctatcca    720
```

```
tgcggtcgcc accaaaacca gaaatacttc ggaccttgtc caaaagagct ctggcccact    780
ccaaaatgtc ggaaaatgtg tcaactaaaa tataatgtgg cctacaaaga cgataaaatt    840
tacgggaatg atgcatacag tctccctaac aatgagacac gaatcatgca agaaattttc    900
acaaatggac ctgtagtggg atcattcagc gtgtttgctg actttgcaat ttataagaaa    960
ggagtatatg tgagtaatgg aattcagcag aatgggctc atgcagtcaa aattattggt    1020
tggggtgtgc aggatggact aaaatattgg ttgattgcta attcctggaa caatgactgg    1080
ggagacgaag ctatgtccg gttccttcgt ggagataacc actgtggaat tgaatcaagg    1140
gtggtgacag gaactatgaa agtgtaaaac aataattagt cttttcctga cgatttcaaa    1200
taaaatcttt gccactaaaa aaaaaaaaaa aaaaaa                              1236
```

<210> SEQ ID NO 30
<211> LENGTH: 342
<212> TYPE: PRT
<213> ORGANISM: Necator americanus

<400> SEQUENCE: 30

```
Met Ile Thr Ile Ile Thr Leu Leu Leu Ile Ala Ser Thr Val Lys Ser
1               5                   10                  15

Leu Thr Val Glu Glu Tyr Leu Ala Arg Pro Val Pro Glu Tyr Ala Thr
            20                  25                  30

Lys Leu Thr Gly Gln Ala Tyr Val Asp Tyr Val Asn Gln His Gln Ser
        35                  40                  45

Phe Tyr Lys Ala Glu Tyr Ser Pro Leu Val Glu Gln Tyr Ala Lys Ala
    50                  55                  60

Val Met Arg Ser Glu Phe Met Thr Lys Pro Asn Gln Asn Tyr Val Val
65                  70                  75                  80

Lys Asp Val Asp Leu Asn Ile Asn Leu Pro Glu Thr Phe Asp Ala Arg
                85                  90                  95

Glu Lys Trp Pro Asn Cys Thr Ser Ile Arg Thr Ile Arg Asp Gln Ser
            100                 105                 110

Asn Cys Gly Ser Cys Trp Ala Val Ser Ala Ala Ser Val Met Ser Asp
        115                 120                 125

Arg Leu Cys Ile Gln Ser Asn Gly Thr Ile Gln Ser Trp Ala Ser Asp
    130                 135                 140

Thr Asp Ile Leu Ser Cys Cys Trp Asn Cys Gly Met Gly Cys Asp Gly
145                 150                 155                 160

Gly Arg Pro Phe Ala Ala Phe Phe Ala Ile Asp Asn Gly Val Cys
                165                 170                 175

Thr Gly Gly Pro Phe Arg Glu Pro Asn Val Cys Lys Pro Tyr Ala Phe
            180                 185                 190

Tyr Pro Cys Gly Arg His Gln Asn Gln Lys Tyr Phe Gly Pro Cys Pro
        195                 200                 205

Lys Glu Leu Trp Pro Thr Pro Lys Cys Arg Lys Met Cys Gln Leu Lys
    210                 215                 220

Tyr Asn Val Ala Tyr Lys Asp Asp Lys Ile Tyr Gly Asn Asp Ala Tyr
225                 230                 235                 240

Ser Leu Pro Asn Asn Glu Thr Arg Ile Met Gln Glu Ile Phe Thr Asn
                245                 250                 255

Gly Pro Val Val Gly Ser Phe Ser Val Phe Ala Asp Phe Ala Ile Tyr
            260                 265                 270

Lys Lys Gly Val Tyr Val Ser Asn Gly Ile Gln Gln Asn Gly Ala His
        275                 280                 285
```

Ala Val Lys Ile Ile Gly Trp Gly Val Gln Asp Gly Leu Lys Tyr Trp
        290                 295                 300

Leu Ile Ala Asn Ser Trp Asn Asn Asp Trp Gly Asp Glu Gly Tyr Val
305                 310                 315                 320

Arg Phe Leu Arg Gly Asp Asn His Cys Gly Ile Glu Ser Arg Val Val
                325                 330                 335

Thr Gly Thr Met Lys Val
            340

<210> SEQ ID NO 31
<211> LENGTH: 759
<212> TYPE: DNA
<213> ORGANISM: Necator americanus

<400> SEQUENCE: 31
acttcaagcg atgttccgtc ctgctactgc cgtccttcta ttgttggccg cgtccagcac      60
atttgctgga ttttcgatg atgttggagg cttacccagt ggtgtgggag attttttcac     120
aaagcagttc aacaatgtga aggatctttt tgctaaagat caagatactc ttgagaagaa     180
tatcaatctg gtaaaggatc tattgattgc cattaaggag aaggctaaga tgctggaacc     240
gatggccaac gaggctcaga agaagacatt agggcaggtg acaactatc tcaatgaagt      300
tcaacagttc ggcgatcagg tagccaagga gggttctacg aaatttgagg agaacaaagg     360
gaaatggcag caaatgttga acgatatctt cgagaaaggt ggactggaca gcgtgatgaa     420
gttgctcaat ctgaagtccg gcggtcgctg cacgttagcc gctgcactcg tcgctcccgt     480
tgtgctcgcg ctcatccgct aattcacttc taccgccgcc gactactgta gtttaccctg     540
tgcctgtgtg tgatatgtgg attgtgcat gatgtgtatc tatgatttgt gatttatttt     600
tctcttgtac ttccatgaat tcagctctgg tattctgaga cggaccaaca tctccgcagt     660
actttttgt attgttatca tcaccgtaat cctgtgactg gcgtaaaatg tttagttttc      720
cgataaaata catttcgaaa aaaaaaaaa aaaaaaaa                               759

<210> SEQ ID NO 32
<211> LENGTH: 163
<212> TYPE: PRT
<213> ORGANISM: Necator americanus

<400> SEQUENCE: 32

Met Phe Arg Pro Ala Thr Ala Val Leu Leu Leu Leu Ala Ala Ser Ser
1               5                   10                  15

Thr Phe Ala Gly Phe Phe Asp Asp Val Gly Gly Leu Pro Ser Gly Val
            20                  25                  30

Gly Asp Phe Phe Thr Lys Gln Phe Asn Asn Val Lys Asp Leu Phe Ala
        35                  40                  45

Lys Asp Gln Asp Thr Leu Glu Lys Asn Ile Asn Leu Val Lys Asp Leu
    50                  55                  60

Leu Ile Ala Ile Lys Glu Lys Ala Lys Met Leu Glu Pro Met Ala Asn
65                  70                  75                  80

Glu Ala Gln Lys Lys Thr Leu Gly Gln Val Asp Asn Tyr Leu Asn Glu
                85                  90                  95

Val Gln Gln Phe Gly Asp Gln Val Ala Lys Glu Gly Ser Thr Lys Phe
            100                 105                 110

Glu Glu Asn Lys Gly Lys Trp Gln Gln Met Leu Asn Asp Ile Phe Glu
        115                 120                 125

Lys Gly Gly Leu Asp Ser Val Met Lys Leu Leu Asn Leu Lys Ser Gly

```
                130                 135                 140
Gly Arg Cys Thr Leu Ala Ala Ala Leu Val Ala Pro Val Val Leu Ala
145                 150                 155                 160

Leu Ile Arg
```

<210> SEQ ID NO 33
<211> LENGTH: 527
<212> TYPE: DNA
<213> ORGANISM: Necator americanus

<400> SEQUENCE: 33

```
aaaagcctcc atagtcatgc tcaagctcgt tgcactcgtt tgcctggttg caatctgctt      60
cgctcaggga ccacaaggac cccctccgtt cctgcaaagt gctccagcgg ctgttcaaca     120
agacttcgac aagctcttcg tcaatgctgg ctccaagact gatgcagaaa tcgacaaaat     180
ggtccaagat tgggttggca acaagatgc atccatcaag accgcattcg atgcgttcgt      240
gaaggaagtg aaagccgctc aagcgcaagg tgaagctgcc catcaggctg ctatcgccaa     300
gttcagcgca gaggccaaag cggctgatgc caagctgagc gcaattgcga acgacaggtc     360
gaagacaaac gcgcaaaagg gagctgagat cgactcggta ctcaagggac ttcctccaaa     420
tgtccgcaca gagatcgaaa acgccatgaa aggataagaa gtctctattt tgtatatatg     480
aaccgataaa tatgcacaat aaaaaaaaaa aaaaaaaaa aaaaaa                     527
```

<210> SEQ ID NO 34
<211> LENGTH: 146
<212> TYPE: PRT
<213> ORGANISM: Necator americanus

<400> SEQUENCE: 34

```
Met Leu Lys Leu Val Ala Leu Val Cys Leu Val Ala Ile Cys Phe Ala
1               5                   10                  15

Gln Gly Pro Gln Gly Pro Pro Phe Leu Gln Ser Ala Pro Ala Ala
            20                  25                  30

Val Gln Gln Asp Phe Asp Lys Leu Phe Val Asn Ala Gly Ser Lys Thr
        35                  40                  45

Asp Ala Glu Ile Asp Lys Met Val Gln Asp Trp Val Gly Lys Gln Asp
    50                  55                  60

Ala Ser Ile Lys Thr Ala Phe Asp Ala Phe Val Lys Glu Val Lys Ala
65                  70                  75                  80

Ala Gln Ala Gln Gly Glu Ala Ala His Gln Ala Ala Ile Ala Lys Phe
                85                  90                  95

Ser Ala Glu Ala Lys Ala Ala Asp Ala Lys Leu Ser Ala Ile Ala Asn
            100                 105                 110

Asp Arg Ser Lys Thr Asn Ala Gln Lys Gly Ala Glu Ile Asp Ser Val
        115                 120                 125

Leu Lys Gly Leu Pro Pro Asn Val Arg Thr Glu Ile Glu Asn Ala Met
    130                 135                 140

Lys Gly
145
```